United States Patent [19]

Leatherman

[11] Patent Number: 5,544,044
[45] Date of Patent: Aug. 6, 1996

[54] METHOD FOR EVALUATION OF HEALTH CARE QUALITY

[75] Inventor: Sheila Leatherman, Minneapolis, Minn.

[73] Assignee: United Healthcare Corporation, Minneapolis, Minn.

[21] Appl. No.: 739,629

[22] Filed: Aug. 2, 1991

[51] Int. Cl.$^6$ .............................. G06F 159/00
[52] U.S. Cl. .......................... 364/401; 128/696
[58] Field of Search .................. 364/413.01–413.04, 364/413.02, 414.415, 413.01, 413.02; 128/696

[56] References Cited

U.S. PATENT DOCUMENTS

| | | | |
|---|---|---|---|
| 3,872,448 | 3/1975 | Mitchell | 340/172.01 |
| 4,667,292 | 5/1987 | Molhenbrock et al. | 364/413.01 |
| 4,737,912 | 4/1988 | Ichikawa | 364/413 |
| 4,878,175 | 10/1989 | Norden-Paul et al. | 364/413.01 |
| 5,018,067 | 5/1991 | Molhenbrock et al. | 364/413.01 |

OTHER PUBLICATIONS

"ULTICARE™, a bedside patient care information system", pp. 1–9, Oct., 1984, Health Date Sciences Corporation, 348 W. Hospitality Ln., San Bernadino, CA 92408.

John R. Weitzel, Kenneth R. Andrews, "A Company/University Joint Venture to Build a Knowledge–Based System," pp. 23–34, Mar. 1988, MIS Quarterly.

Jun-ichi Sugiara, Yasuichi Kaku, Kazukiyo Kawanobe, "Shared Hospital Information System–Electronic Data Processing in Hospital," pp. 53–61, Jan. 1980.

Japan Telecommunications Review, vol. 22, No. 1 Paul Beard, "Blue Cross develops insurance claim ES," p. 3, Apr. 1, 1989, AI Week.

Malcolm Gladwell, "Computer Firm Find the Link for Health Care," pp. 5–6, Dec. 5, 1988, Washington Business.

J. P. Weiner, et al., "Applying insurance claims data to assess quality of care: A compilation of potential indicators," 16:424–438, 1990, QRB.

Michael Gray, "Appraising Managed Healthcare's Quality," pp. 8, 9 and 12, Summer 1991, Managed Care Insights.

Linda J. Collins, "Managed Care May Improve Quality," pp. 3–5, Feb. 1990, Business Insurance.

D. Berwick, "Toward an Applied Technology for Quality Measurement in Health Care", Medical Decision–Making, vol. 8, No. 4 (Oct.–Dec. 1988).

K. Lohr, "Use of Insurance Claims Data in Measuring Quality of Care", International Journal of Technology Assessment in Health Care 6: 263–271 (1990).

Sweet et al., "Infectious Diseases of the Female Genital Track", 2nd Edition, 1990, ISBN 0-683-08039-3 pp. 109–119 pp. 35–37, Mar./Apr. 1987.

(List continued on next page.)

Primary Examiner—Gail O. Hayes
Assistant Examiner—Frantzy Poinvil
Attorney, Agent, or Firm—Dorsey & Whitney LLP

[57] ABSTRACT

A software-based medical information system performs a method of analyzing health care claims records for an enrolled population (e.g., HMO, Medicaid) to assess and report on quality of care based on conformance to nationally recognized medical practice guidelines or quality indicators. The system analyzes health care received by enrollees having a specified health care condition by: providing to the system health care claims records for a selected enrollee population; defining at least one health care condition in terms of health care events reportable in health care claims records; identifying in the health care claims records those enrollees meeting the definition for that health care condition; defining health care quality criteria for that health care condition in terms of health care events reportable in health care claims records; comparing the health care quality criteria for the at least one health care condition to the health care claims records for at least a portion of those enrollees meeting the definition for that health care condition; and developing and outputting from the system a health care quality report based on the comparison and formulating action recommendations to improve care. The system provides an efficient means to supplement claims data with data from patient medical records.

23 Claims, 10 Drawing Sheets

OTHER PUBLICATIONS

"Quality of Care", Quality Progress V20n5, pp. 22–24, May 1987.

Weiner et al., "Applying Insurance claims data to assess quality of care", Department of Health & Policy and Management, School of Hygiene and Public Health, Johns Hopkins University, Baltimore, Md, QRB Qual Rev Bull, 12, 1990.

Pizzi, "Service Guarantee, EDI Key to Total Quality Management at Delta", Group Practice Managed Healthcare, v. 10 No. 6 p. 22B (4), Jun. 1994.

Wieners, "Quality measurement & Sererity systems—an overview", Computers in Healtcare vol +v9, Issue:N10, p. 27(4), Oct. 1988.

"The Computerized Severity Index: A new Sophisticated Tool to measure hospital quality of care", Health care Forum v30 No. 2.

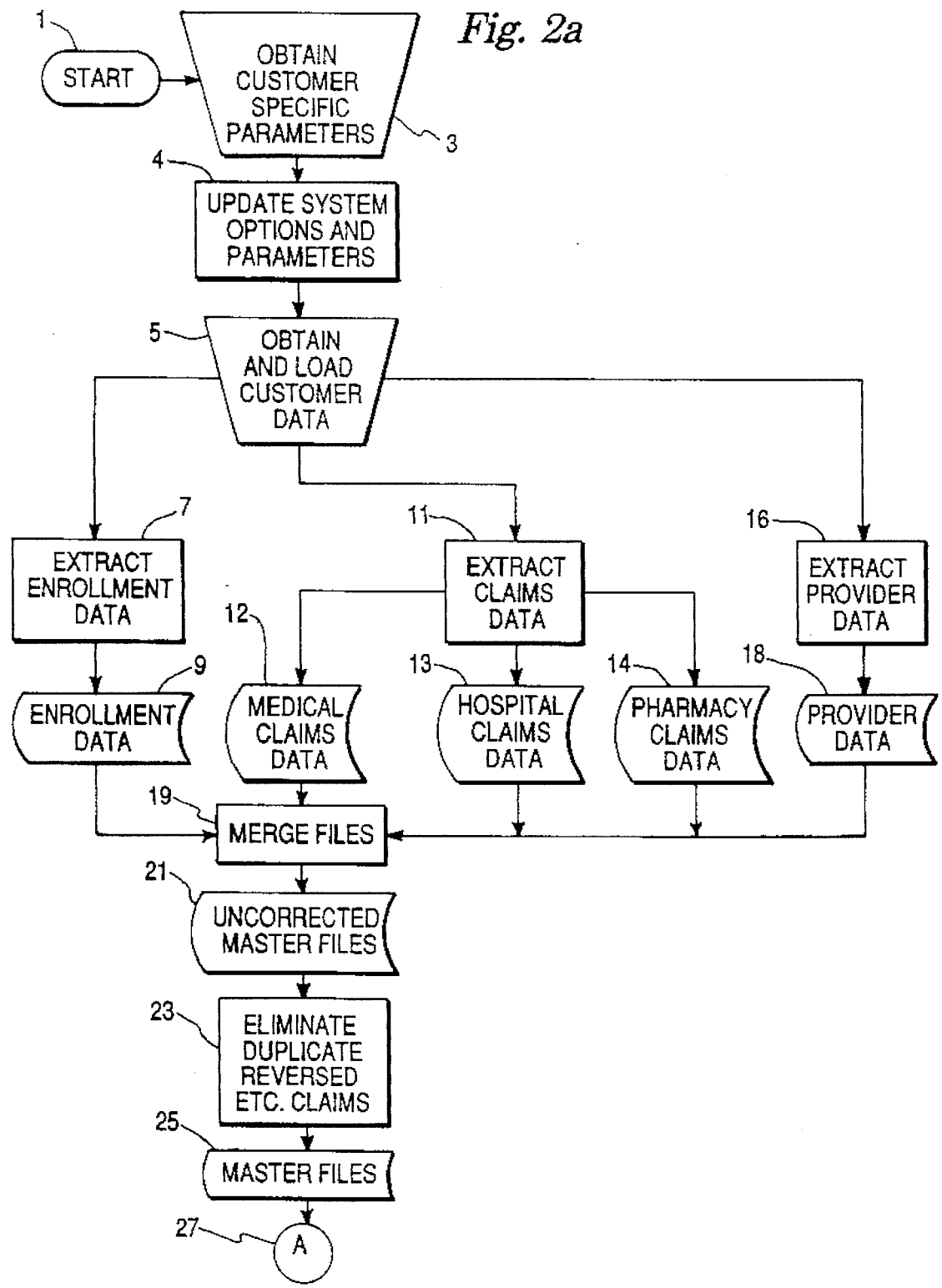

METHOD FOR EVALUATION OF HEALTH CARE QUALITY

TECHNICAL FIELD

The present invention relates to a data processing method and system for analyzing health care records and generating information in the form of statistical charts and graphs, evaluations and recommendations suggesting changes for improving the quality of health care services received by a patient population through a health care benefit organization. In particular, the present invention relates to a quality screening and management system for organizing, describing, analyzing, evaluating and reporting on the quality of health care services received by an enrolled or defined population of health care beneficiaries.

BACKGROUND OF THE INVENTION

The system of medical health care delivery in the United States is facing a critical point in its evolution. The escalating cost of health care, marked variation in the practice patterns of physicians, the increasing number of uninsured or under-insured individuals and the dissatisfaction of the public with the current health care system in this country have all contributed to the crisis currently faced by health care benefit providers. The root of the current crisis is best analyzed from an historical perspective.

The structure of organizations responsible for providing medical insurance benefits has shifted over the course of time from local providers to more complex managed health care systems of providers. The administrative structure developed to support health care providers has also grown more complex and has assumed oversight responsibilities. One of these responsibilities is the quality assessment of health care services.

Previously, if health care providers assessed the quality of health care services received by patients, they generally did so by "incident reporting" in which quality problems were identified by isolated report or individual case inquiry. Quality assessment with respect to medical practice patterns of physicians was based on the traditional method of peer review of medical records. These methods, however, are labor-intensive and inefficient. As health care organizations grew, new avenues for evaluating quality of care were explored.

More sophisticated data systems were developed to assist health care organizations, but these focused predominantly on the collection of financial data. These systems were designed to track the cost of health care by reporting actual cost incurred. While these prior art systems performed adequately for these simpler accounting and administrative functions, they became increasingly inadequate to meet the needs of the more complex managed health care systems.

The prior art health care management systems lacked organized health care data bases and evaluation methods, which permit evaluation of comprehensive health care delivery. Purchasers, providers and administrators have lacked the ability to measure and identify quality of care problems with efficiency and inclusive of whole populations receiving services. In prior art health care management systems, quality issues were generally revealed by inference in conducting utilization reviews, case management or financial analysis or in restricted areas, such as inpatient care only. This is in contrast to the direct study of quality and/or access, two factors that are presently considered crucial to the proper evaluation of health care delivery systems, and in distinction to evaluating comprehensive health care spanning inpatient and outpatient services. Management that is cost-effective, whether performed by physicians in direct patient care or administrators of managed health care systems, necessitates the collection and integration of information on the health care process, appropriateness of the medical intervention, and effectiveness, viewed in terms of outcomes. To maximize the availability and use of such information for large scale health care evaluation, it should be collected from standardized data. Through the use of such data, comparisons between actual clinical practice and authoritative practice guidelines can be made to identify opportunities to improve health care delivery and health outcomes.

Current practices of quality of care assessment depend primarily on the review and evaluation of medical records, which is costly, intrusive and not conducive to the evaluation and reporting of care delivered to large patient populations, except on a sampling basis. Medical records also may not include full pertinent information on utilization of vital services, such as laboratory or pharmacy services. In addition, current practice often focuses on placing blame on the provider, which fosters resistance by physicians to quality of care assessments, and neglects the need to consider the role of patients, purchasers and health care organizations in quality of health care. Further, current practices concentrate on merely monitoring performance without giving sufficient attention to concrete steps for improving the quality of care received by patients.

The existence of managed health care systems providing reimbursement for health care services to medical professionals, hospitals and pharmacies has led to the building of large collections of data reflecting the payment (and in some cases, the denial of payment) of claims made by individuals who are members of a managed health care plan. However, because these data are collected for financial purposes, they have not been organized or coded in a fashion that permits them to be used readily for purposes other than cost analysis. In particular, these data have not usually been used as a source of information for evaluating the quality of health care provided. Yet these data are frequently maintained on computers and, for health care systems that have several years of experience with significant participant populations, these data report, on a relatively reliable basis, the occurrence of a large number of health care services transactions for a wide variety of medical conditions, including inpatient, outpatient and pharmacy transactions.

A quality of health care screening system designed for complex managed health care systems, using the significant historical databases of claims records for the evaluation of and reporting on appropriate delivery and receipt of health care services would be a decided improvement over the prior art.

SUMMARY OF THE INVENTION

The problems outlined above are in large measure solved by the quality screening and evaluation system in accordance with the present invention. The quality screening method in accordance with the present invention uses clinically meaningful indicators to define standards for and monitor the quality of health care received by a defined population. By analysis of computerized data, the method identifies areas with quality improvement potential for appropriate follow-up actions.

The quality screening and evaluation system in accordance with present invention defines a health care condition in terms of a set of predetermined condition criteria; uses the condition criteria to analyze a health care claims data base linking inpatient and outpatient, pharmacy and health plan enrollee records and identify a population of individuals who meet the predetermined condition criteria; defines quality of care criteria for the specific medical condition; compares the quality of care criteria against the health care claims data base for the identified population; and develops a set of prescriptive and descriptive reports based on that comparison for improving health care delivery. The claims data base for the identified population can be supplemented by data obtained from medical records to provide a more detailed evaluation.

BRIEF DESCRIPTION OF THE DRAWINGS

FIGS. 2A–2D are a flow chart depicting the overall operation of the method of the present invention.

DETAILED DESCRIPTION OF THE DRAWINGS

Figure 1:
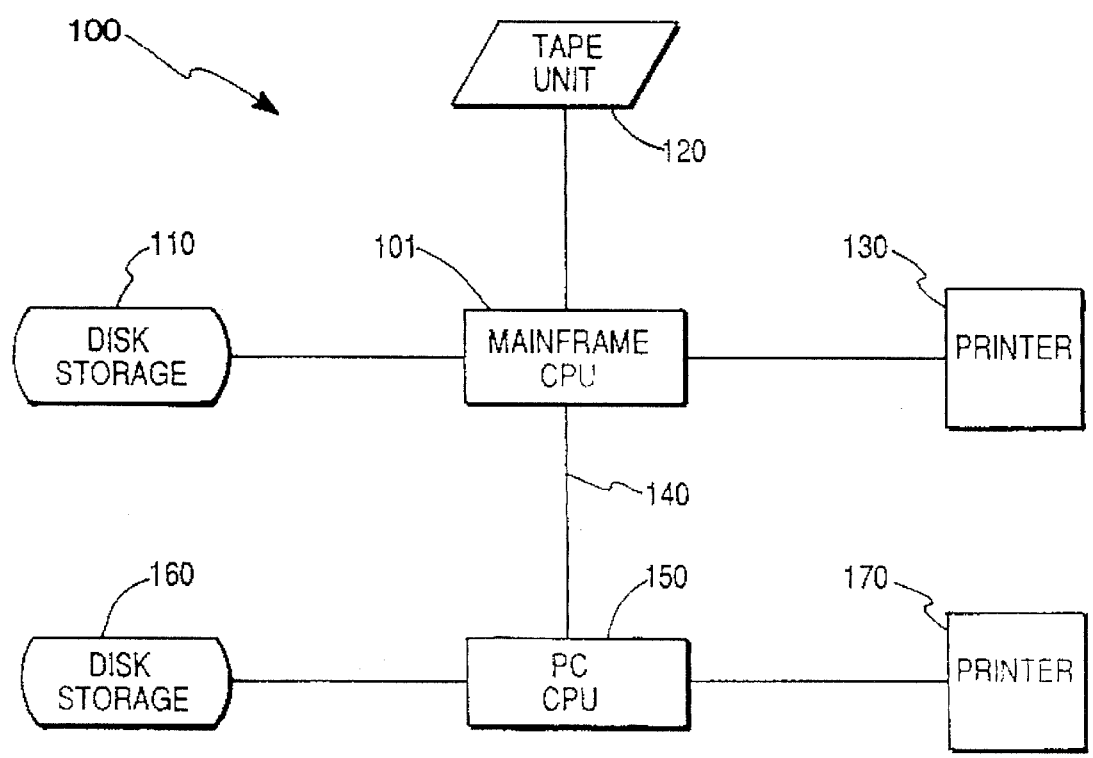
FIG. 1 is a block diagram schematically illustrating a data processing system in accordance with the present invention.

Referring to FIG. 1, a data processing system 100 for evaluating the quality of health care received by a defined population is shown in block diagram form. A mainframe central processing unit (CPU) 101 is connected to a magnetic disk memory storage unit 110 and a secondary memory device 120, such as a magnetic tape drive, used to input data to the system 100 for eventual storage on the magnetic disk unit 110. Also connected to the CPU 101 is a printer 130 for producing hard copy reports reflecting the analysis performed by the system 100. A personal computer processing unit 150 is connected to the mainframe CPU 101 via a data communications line 140 for the purpose of entering data, such as medical records, performing analysis on the medical records or other data and for formatting reports. Connected to the personal computer 150 is a magnetic disk storage unit 160 for storing medical records or other data entered and a printer 170 for producing hard copy reports and graphics reporting the results of the analysis performed by the system 100 for delivery to customers.

Stored in the magnetic disk memory units 110 and 160 are software instructions that serve as the operating systems and the application software. These together direct the operations of the CPU 101 and the personal computer 150 on the data in the disk memory units 110 and 160. The application software contains the computer language instructions that cause the system to perform the methods of the present invention.

Figure 2B:
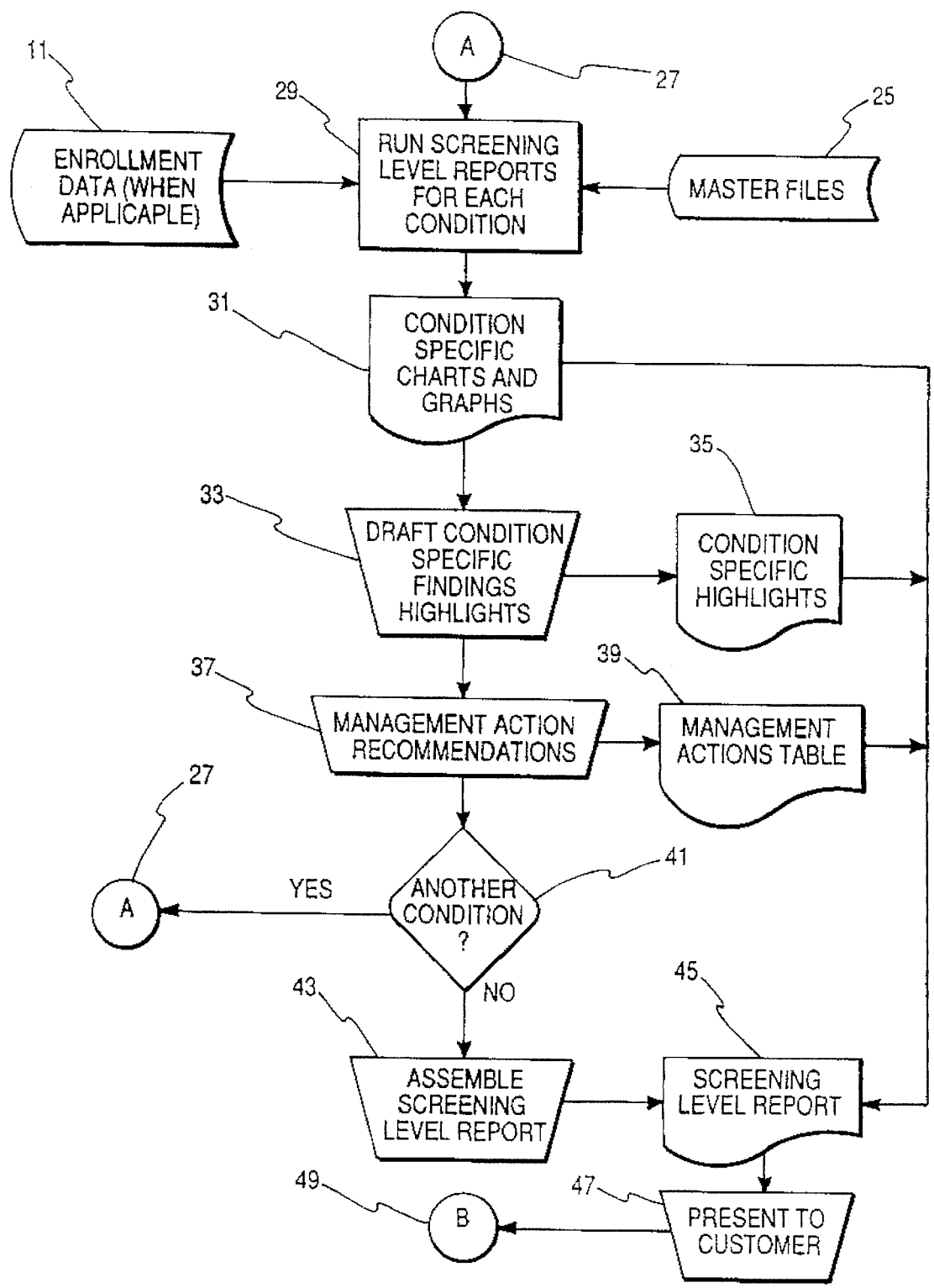
Figure 2C:
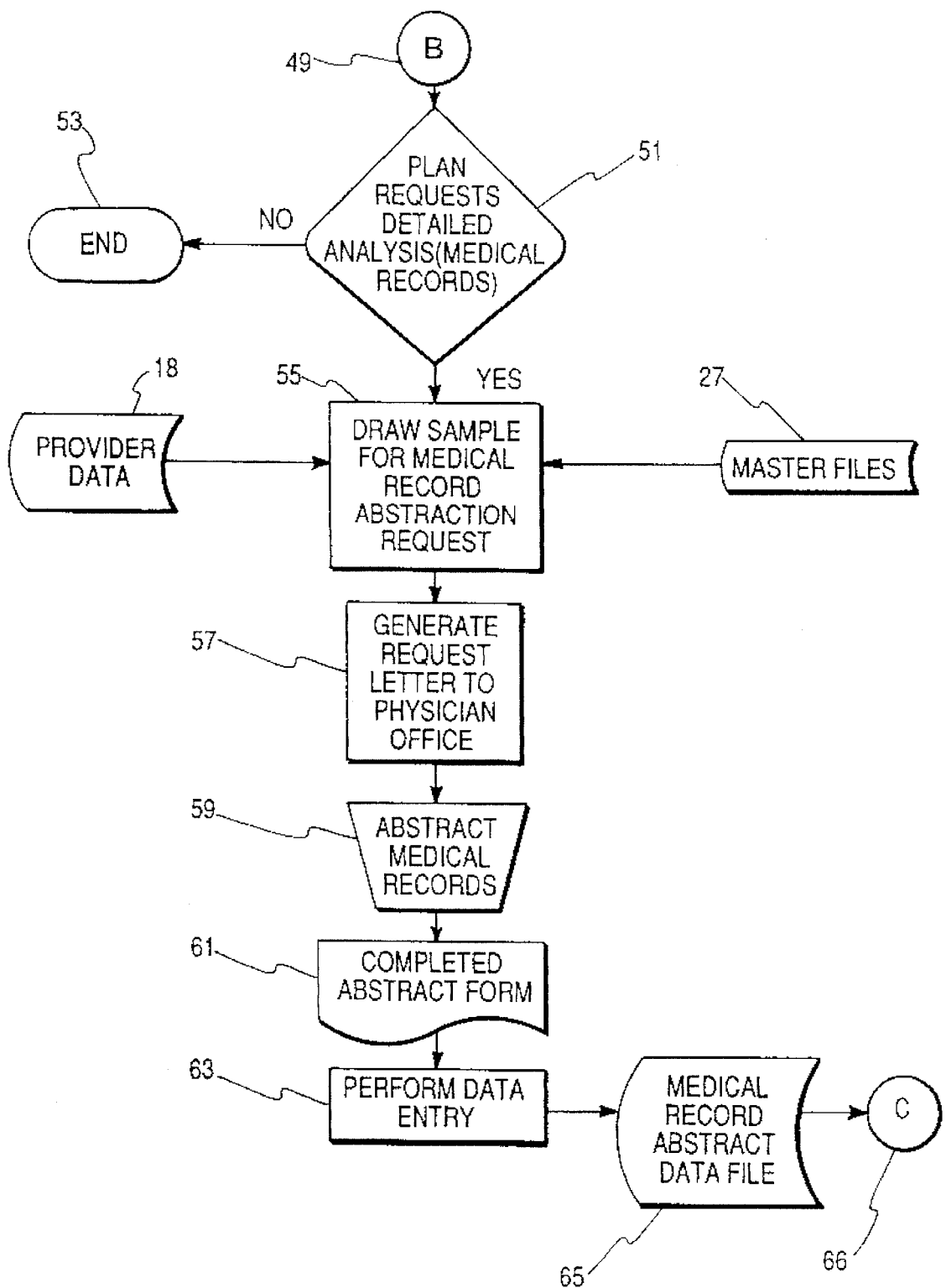
Figure 3A:
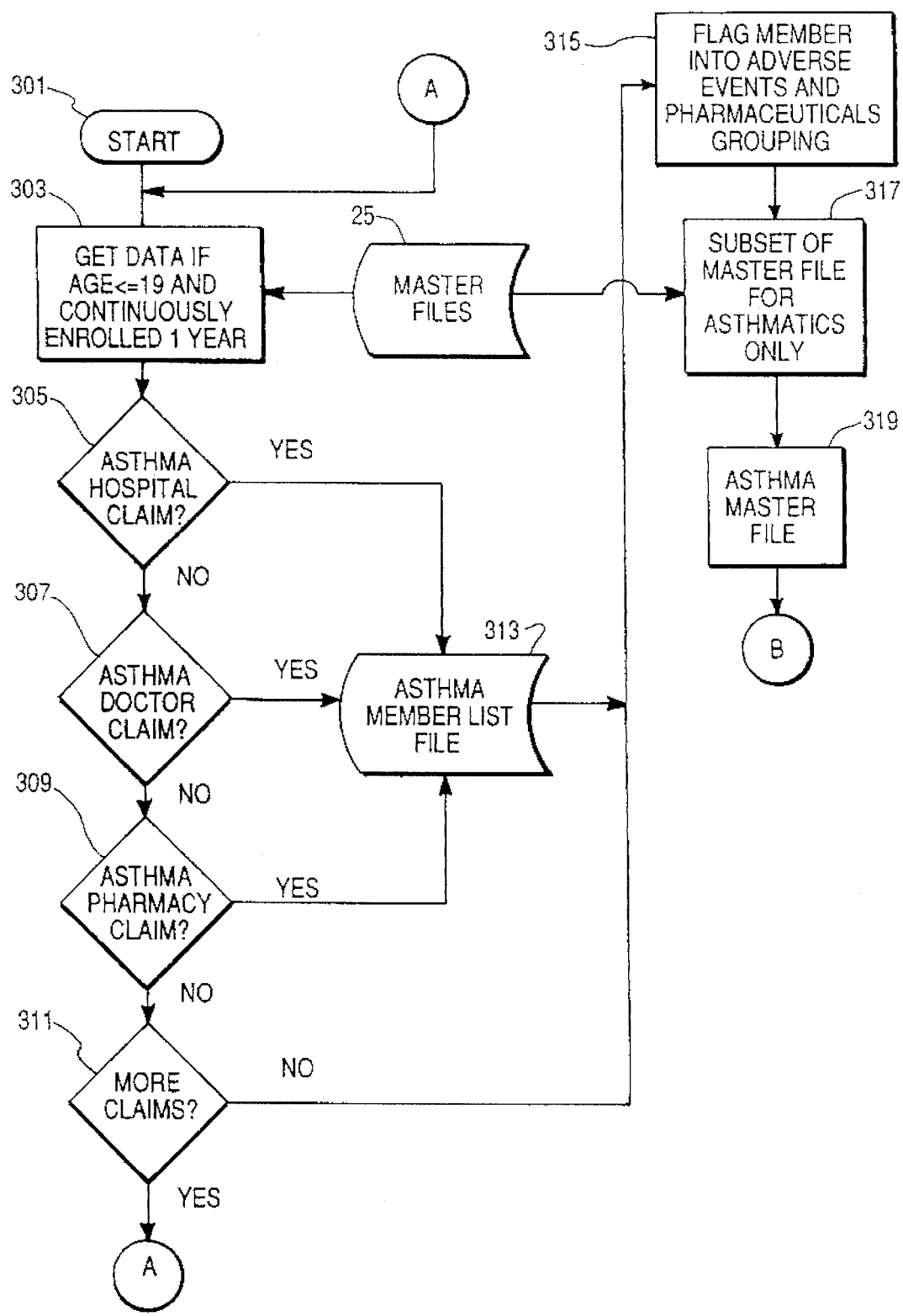
FIGS. 3A–3C are a flow chart depicting the data analysis details of the present invention with respect to a specific health care condition in the nature of a disease or organic dysfunction.
Figure 3B:
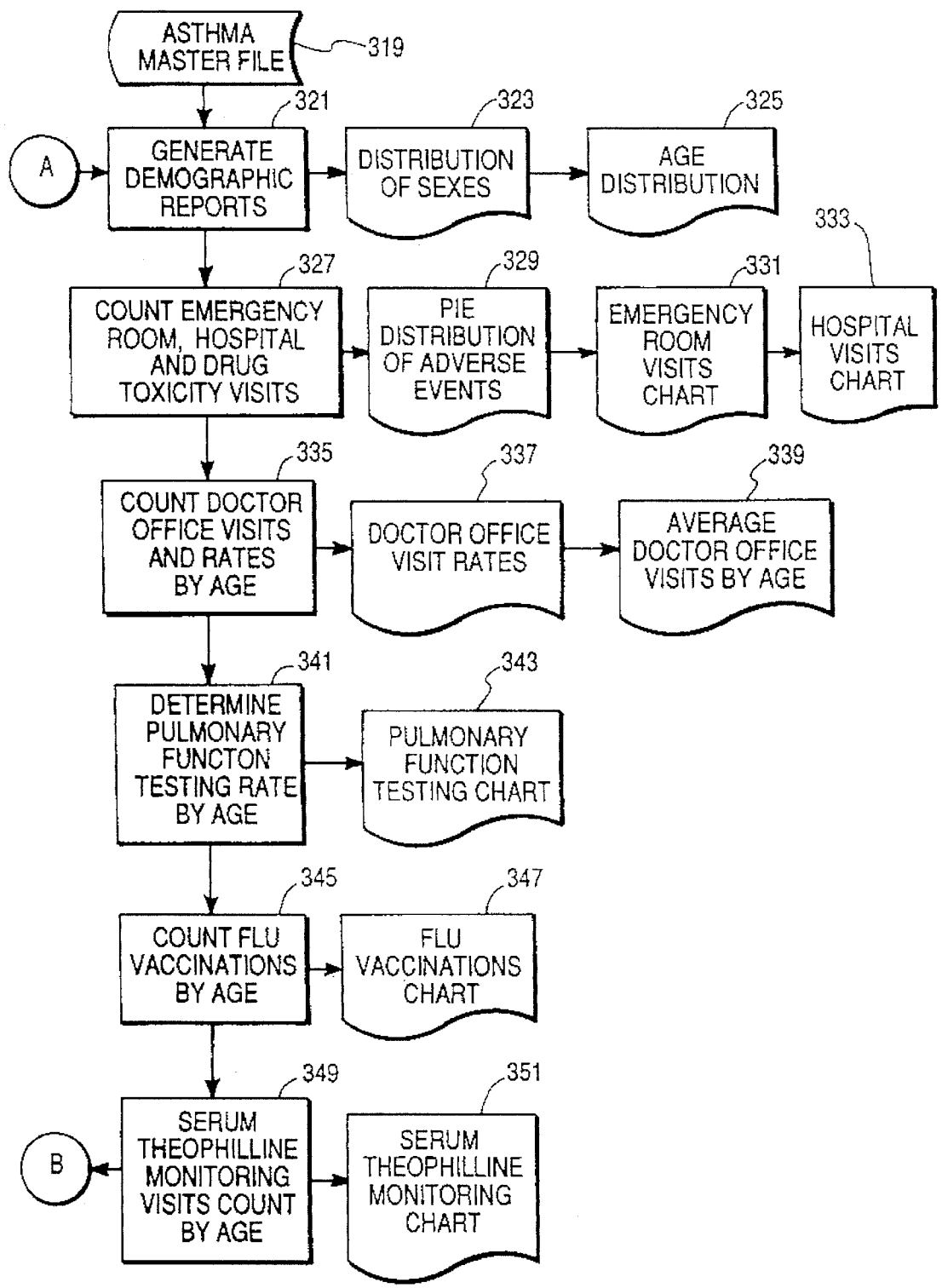
Figure 3C:
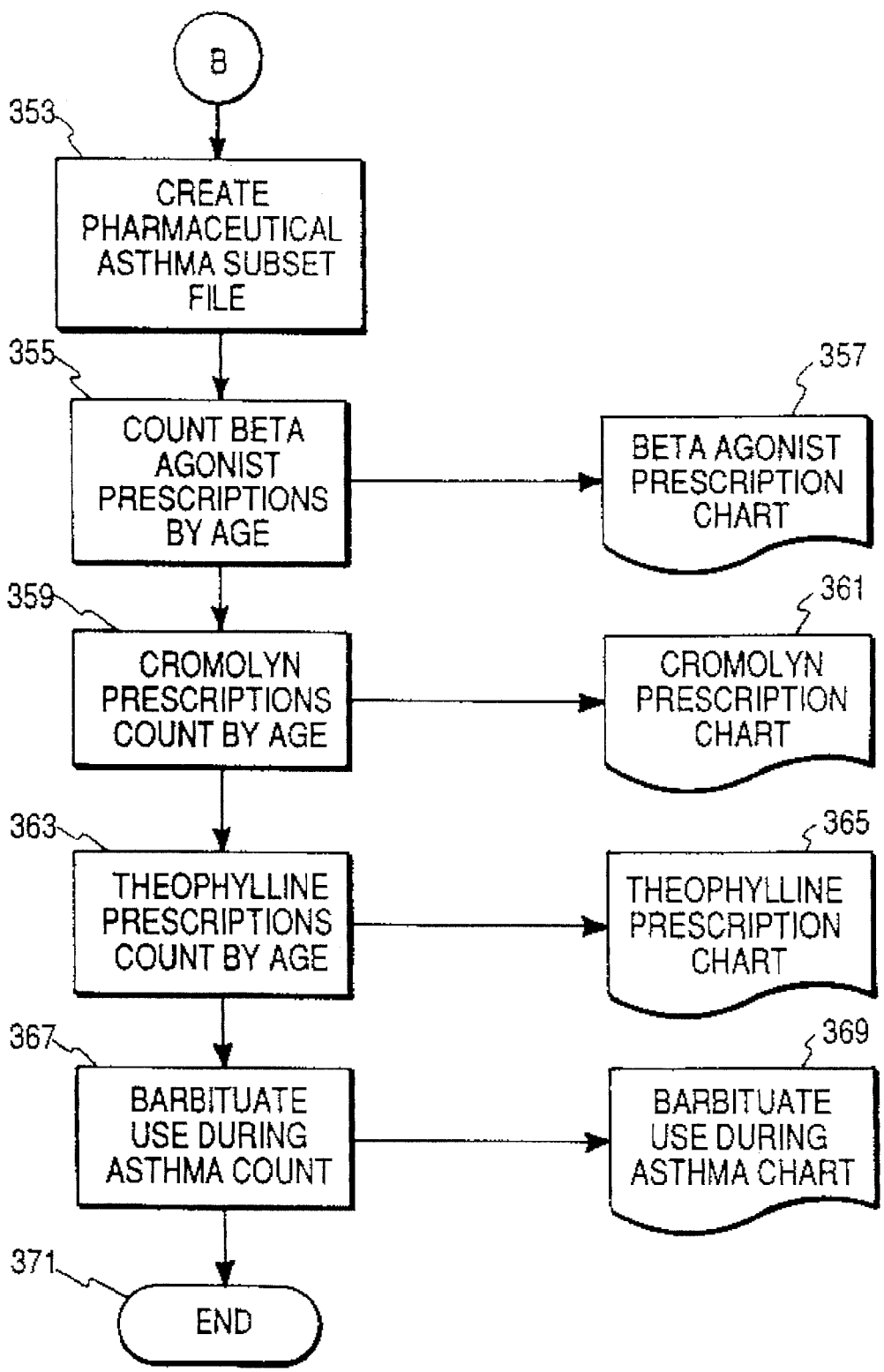
Figure 4A:
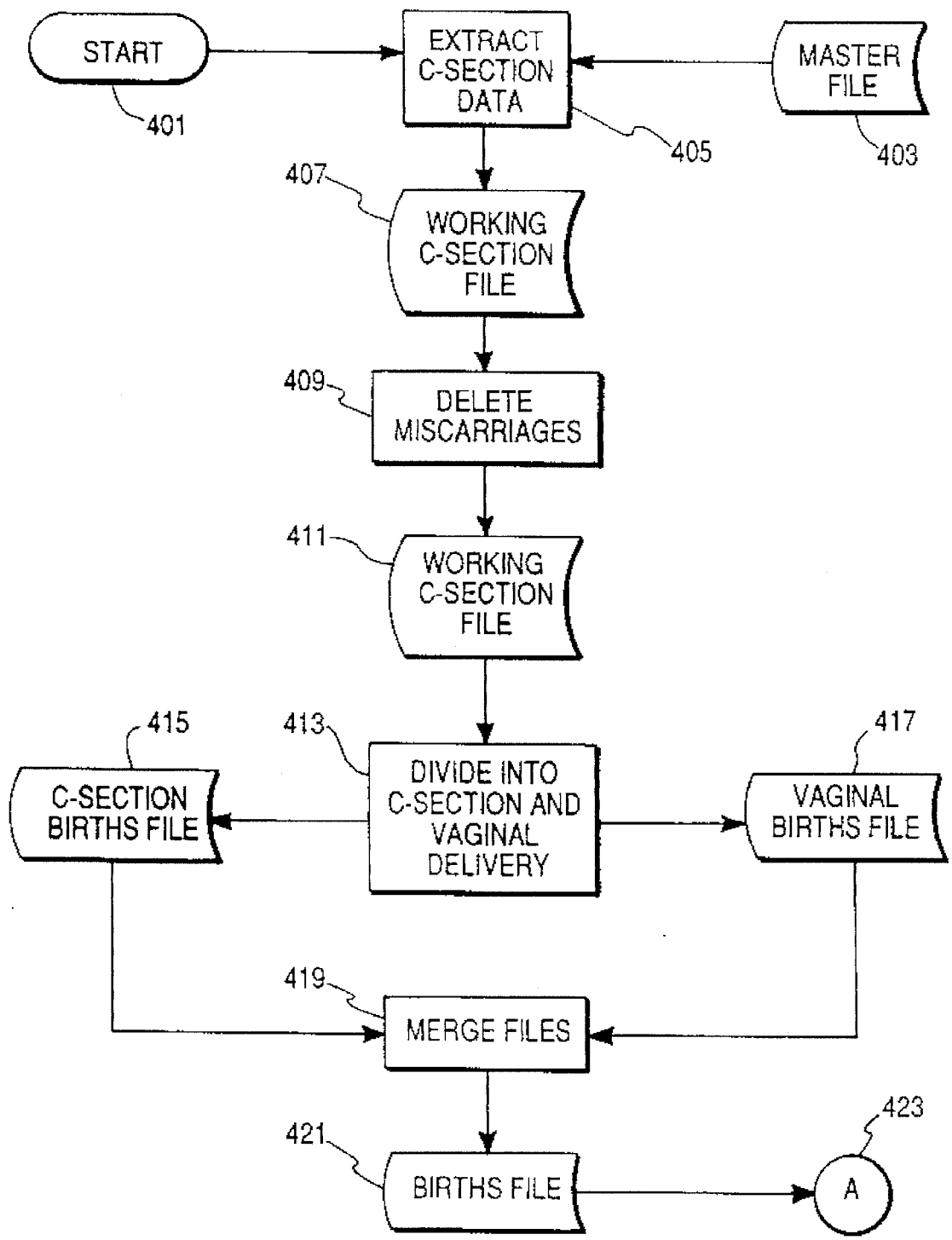
FIGS. 4A–4B are a flow chart depicting the data analysis details of the present invention with respect to a specific health care condition not in the nature of a disease or organic dysfunction.
Figure 4B:
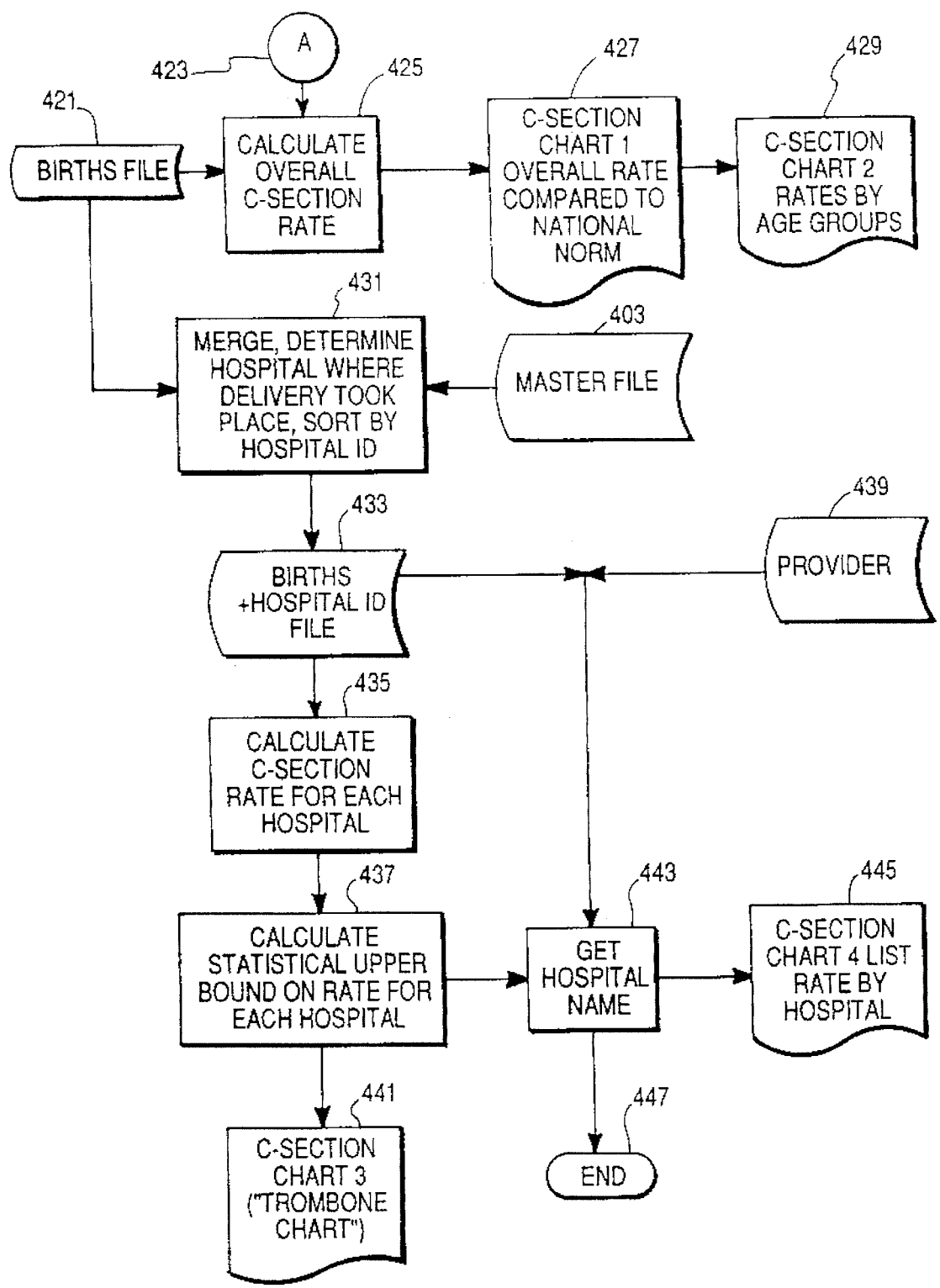

In the preferred embodiment, the application software is written primarily in a language called SAS, Version 6.06. Certain data entry functions are, however, implemented in dBase IV language. The CPU 101 is preferably an IBM mainframe utilizing the VM/CMS operating system. The personal computer 150 is preferably an IBM PS/2 utilizing the OS/2 operating system. The structure of the application software and the methods of the present invention are depicted most readily in flow chart form. FIGS. 2A–2D show a flow chart depicting the overall operation of the method of the present invention. FIGS. 3A–3C are a flow chart depicting the data analysis details of the present invention with respect to a specific health care condition in the nature of a disease or organic dysfunction. For purposes of illustration, FIGS. 3A–3C show a flow chart for the method of the present invention as applied to pediatric asthma FIGS. 4A–4B a flow chart depicting the data analysis details of the present invention with respect to a specific health care condition not in the nature of a disease or organic dysfunction. For purposes of illustration, FIGS. 4A–4B show a flow chart for the method of the present invention as applied to caesarian sections. The particular health care conditions discussed in FIGS. 3A–3C and 4A–4B are illustrative examples only and, as will become clearer in the discussion below, the method of the present invention can be used to address many other health care conditions in a similar manner.

The flow charts of FIGS. 2A–4B have the following symbols:

circle—connector (null operation)
ellipse—start or stop terminator
rectangle—computer process
trapezoid—manual process
diamond—decision or-test
rectangle with curved bottom—document output
rectangle with curved sides—disk file Overall Process Logic Flow a. Initial Screening Analysis Turning now to FIG. 2A, the overall process of the present invention can be explained. The process will typically be performed at the request of a customer that is a health maintenance organization, indemnity insurer (e.g., Blue Cross), a large, self-insured employer group or a government program (e.g., Medicaid). Such customers administrate one or more health care benefit plans servicing individuals who are enrolled in a plan. At the start 1, the first step 3 is to obtain the customer specific parameters, such as what time period the customer wishes to analyze or whether the customer wants to have some data broken down by particular providers or other grouping variables. The next step is to update the system options and parameters using the customer specifications. Thereafter, the system 100 obtains and loads 5 the customer data, usually consisting of the customer's already-computerized health care claims data for a specified period, together with enrollment data and health care provider data. Typically this information can be provided on magnetic tape and is easily placed in the magnetic disk unit 110 of the system 100 by means of a magnetic tape drive 120.

The enrollment data is extracted 7 so as to identify the enrollees served by the customer that meet a predefined enrollment criterion, such as that each enrollee has been enrolled in the health plan for a specified period. The resulting enrollment data 9 contains one record per enrollee. Next, the relevant claims data are extracted 11 from the complete customer data base and are configured through linkages to produce the necessary health records. This involves selecting only the claims data for the time period being examined. It should be noted that the claims data usually includes a code identifying a defined health care procedure or service. The claims data will include claims records for medical professional services 12 (outpatient records), claims records for hospital services 13 (inpatient records) and claims records for pharmacy purchases 14 (pharmacy records). (A particularly focused analysis may not have data of all three types.)

Ideally, the customer's data base will contain all of the following data fields:

| Enrollment/Membership Data | | |
|---|---|---|
| 1.R | Unique Member Identifier | |
| 2.R | Enrollment Date | |
| 3.R | Expiration Date | |
| 4.R | Birth Date | |
| 5.R | Gender | |
| 6. | Patient Name (only if a medical record review is requested) | |
| 7. | Medicare Membership Indicator | |
| 8. | Medicaid Membership Indicator | |
| 9. | Zip code | |
| Medical Professional Claims Data | | |
| 1.R | Unique Member Identifier | |
| 2.R | Date of Service | |
| 3.R | Provider Type Code (for physicians this must indicate medical specialty) | |
| 4. | Unique Provider Identifier (required if Provider Type is not available on the claims record or if medical record review is anticipated) | |
| 5.R | Diagnosis Code (ICD-9) | |
| 6.R | Procedure Code (CPT-4) | |
| 7.R | Place of Service Code (e.g., hospital, doctor's office) | |
| Hospital (Inpatient/Emergency Room) Claims Data | | |
| 1.R | Unique Member Identifier | |
| 2.R | Admission Date | |
| 3. | Discharge Date | |
| 4.R | Provider Type Code (for in-patient claims this must indicate type of facility. e.g., hospital, emergency room, urgi-center) | |
| 5. | Unique Provider Identifier (required if Provider Type is not available on the claims record or if in-patient medical record review is anticipated) | |
| 6.R | Place of Service Code | |
| 7. | Unique Admission Identifier | |
| 8.R | Diagnosis Code (ICD-9) | |
| 9. | Revenue Code (i.e., from UB82 codes) | |
| Pharmaceutical Claims Data (not used for all conditions) | | |
| 1.R | Unique Member Identifier | |
| 2.R | Drug Codes | |
| 3. | Route of Administration | |
| 4. | Quantity of Drug | |
| 5.R | Filled Date | |

The minimum required fields for the present implementation of the invention are marked with an "R" in the above data definitions. "CPT-4" in the medical professional data refers to an edition of the Current Procedure Terminology code, published by the American Medical Association. In the medical professional data and the hospital data, "ICD-9" refers to an edition of the International Classification of Diseases; "UB82" refers to revenue codes published by Health Care Finance Administration; and Place of Service Codes are those promulgated by the American Medical Association. Alternative coding systems can be used, based on a code conversion table associating the preceding codes with the alternative coding system.

If the customer desires, provider-specific data is also extracted 16 from the customer data, permitting the later analysis to be broken down by the particular provider of services or products, which may be a particular doctor, clinic or hospital. (The provider data also can be used to identify the possible sources of medical records.) The provider data fields utilized are as follows:

| Provider Data (e.g. Physician Hospital, Urgi-Center) | |
|---|---|
| 1. | Unique Provider Identifier |
| 2. | Provider Type Code (if not in Claims Files) |
| 3.RM | Name |
| 4.RM | Street Address |
| 5.RM | City |
| 6.RM | State |
| 7.RM | Zip Code |
| 8.RM | Area Code |
| 9.RM | Phone Number |

Additional fields required if a medical record review is to be undertaken are marked with an "RM".

The resulting files are merged 19 to produce uncorrected master files 21. Because claims data are not totally "clean", it will typically be necessary to exclude duplicate claims 23 and claims that have been reversed through the claims adjudication process (coordination of benefits, subrogation, clerical errors). This produces a master file 25 of health care claims records. No adjustment is performed for claims lag. It is assumed that a customer will not forward data for analysis until the claims have been sufficiently processed for the period of study desired.

At this point the health care claims records are ready to be analyzed for indicators of quality. But this analysis requires two further preliminary steps: (1) defining at least one health care condition in terms of health care events reportable in health care claims records; and (2) defining health care quality criteria for each defined health care condition, also in terms of health care events reportable in health care claims records. This must be done in advance of the analysis of the master file 25 of health care claims records. The reason that it is necessary to define a health care condition is that quality measurements are specific to discrete health care conditions: what a provider should do obviously depends on the member's condition, the symptoms, diagnosis or the health care status (e.g., pregnancy). More important for this invention, individual health care claims data items accumulated in the normal course of business by a health care management entity may or may not include a direct and specific diagnosis of the particular health care condition suffered by an enrollee or the particular health care condition that is of interest from a quality measurement viewpoint. Even if a diagnosis is present in claims records, it is not necessarily valid to take it at face value. The claims data include one or more codes identifying specific treatment events or outcomes, such as, an office visit, a blood test, a CAT scan, a surgical procedure, a drug prescription, a hospital stay with charges for drugs, X-rays or specific therapeutic regimens, a hospital readmission or a death. It is a selection of such data items and their relationships that becomes the definition of a particular health care condition.

For purposes of the present invention "health care condition" is broadly defined to mean a condition in the nature of a disease or an organic dysfunction or a "condition" that might also be viewed as a status or an outcome. In its present implementation, the following conditions characterized as diseases or organic dysfunctions or outcomes are addressed: diabetes mellitus, pediatric asthma, hypertension, breast cancer, hospital readmissions and ambulatory surgical complications. The following conditions characterized as status-based are also addressed: pediatric immunizations, breast cancer screening, cervical cancer screening, caesarian section and prenatal care. The point of each condition is to provide a focus for analysis of quality of care, not for medical diagnosis. Given this orientation, the preceding conditions were selected for implementation, because each can be associated with a cluster of health care events that can be related to health care quality criteria as well as with data that can be used to identify a population having the condition. A proper course of testing and treatment is part of quality care to maximize the health of a person with diabetes mellitus. To protect the health of children with certain age status, a prescribed set of immunizations is agreed to be necessary. To protect the health of women in various age groups and/or meeting other status criteria, certain screening tests and examinations, at prescribed intervals, are agreed to be necessary. To protect the health of newborns and their mothers certain prenatal care is agreed to be advisable.

As will be seen below, defining some health care conditions for purposes of quality measurement is easier than defining others. The caesarian section condition is usually easy to define, because there will often be a specific claims code when the surgical procedure is performed. However, in some circumstances, there will not be a specific claims code and the condition will be deduced from the presence of a combination of claims codes, perhaps including amniocentesis, frequency of prenatal visits and specific anesthesia or surgery events. Pediatric asthma is an example of a more subtle condition, and, as will be shown, is defined in terms of a set of medical claims codes, hospital claims codes and pharmacy claims codes with specified Boolean (logical) relationships. Selecting the codes for such conditions can be difficult, because they are not always diagnosed the same way and may be diagnosed only after repeated visits to a health care provider or may not be diagnosed at all. The code selection definitional effort resembles the diagnostic process performed by a health care professional who studies the medical record of a new patient. That is, defining such a condition is a complex logical process requiring extensive clinical and claims data knowledge to implement the definition in a software algorithm.

For all of the conditions addressed by the present invention, it is necessary to define the health care condition of interest solely in terms of data elements reportable in health care claims records. This is a different task than if the entire medical record were available, with its greater range of terminology and information. As noted above, in the preferred embodiment the claims data include outpatient records, inpatient records and pharmacy records. Thus, data from all of the record sources can be used to make a health care condition definition. This is significant, because provider practice patterns and enrollee behaviors may cause a clear picture of the enrollee's health care status to emerge only when data from all of these sources is considered.

Once a specific definition is created for a health care condition of interest for quality screening, this definition is implemented as a series of logically linked compare operations in the software. Applying the definition of the health care condition to the claims records becomes a matter of performing the compare operations and executing the Boolean logic implicit in the definition (and explicit in the software) to identify those enrollees having claims records in the claims data base that meet the definition. The enrollees so identified are the subset of the universe of health care system enrollees that becomes the focus of the further analysis to determine whether this subset, identified as having the defined health care condition, received quality health care for that condition.

The second prerequisite for analysis of the claims master files 25 is defining health care quality criteria for each defined health care condition, also in terms of health care events reportable in health care claims records. Here, the health care system manager must rely on knowledge sources credible to practicing clinicians. Typically, study of the condition will reveal that quality of care is indicated by the absence of certain kinds of health care claims (e.g., an emergency room visit for a pediatric asthma patient, hospitalization for diabetes mellitus, reoccurrence of breast cancer or other adverse events) and the presence of other kinds of health care claims (e.g., annual inoculations, laboratory testing at specific intervals, visits to appropriate medical/surgical specialists, prescription of specific medications). Specific evaluation criteria are developed from clinical or health services literature and research, from standards developed by the professional societies and through private or public (federal government) task forces. As with the definition of the health care condition of interest, the health care quality criteria must be implemented in the software as a set of physician office claims codes, hospital claims codes and pharmacy codes with specified Boolean relationships.

Returning to FIG. 2B, step 29 involves the application of the definitions for the health care condition to identify the population having that condition, followed by an analysis of the claims records for that population (a subset of the master files 25) under the defined quality care criteria. The enrollment data 11 is accessed in this process, as well. In general, the invention is implemented to examine one year of claims data, which may begin on any date in a year. Analysis of an enrollee's claims records for the following conditions occurs only when the enrollee has been continuously enrolled for one year: diabetes mellitus, pediatric asthma, hypertension, breast cancer, and breast cancer screening. There is no one year continuous enrollment requirement when the following conditions are analyzed: cervical cancer screening, pediatric immunizations (ages birth to two and four to six), hospital readmission, ambulatory surgical complications and caesarian section. For the prenatal condition, the enrollment requirement is enrollment six months prior to delivery, but enrollment past the date of delivery is not required.

The result of the analysis in step 29 is a report that includes: charts and graphs 31 reporting statistically observed quality of care data in the population defined as having the health care condition of interest (e.g., a graph showing emergency room visits by patient age); a written analysis reporting, from a care quality viewpoint, statistical results considered worthy of highlighting 33, 35 (e.g., a report of use of a particular drug intervention and the occurrence of adverse events associated with the particular health care condition); and a report containing recommendations for actions to improve health care quality 37, 39 (e.g., a suggestion that physician guidelines be developed and promulgated stating that a specified laboratory test be performed annually).

Action recommendations to improve health care quality are produced for each condition studied. These recommendations are selected from a menu of nine quality management action categories developed based on a synthesis of the relevant research literature and management expertise. The nine categories are: (1) reporting the results of the quality analysis to physicians, (2) disseminating practice guidelines to physicians, (3) instituting condition-specific medical record flowsheets, (4) modifying reimbursement to physicians, (5) instituting provider discipline, (6) providing patient education and reminders, (7) establishing case management programs, (8) improving patient access to care, and (9) changing the benefit design. As can be seen, these actions are directed toward affecting the behavior not only of physicians, but also patients, purchasers or providers of benefits, and health care organizations. Each condition has a set of condition-specific action recommendations defined for it. The customer's report will include those recommendations from the set that are appropriate in view of the results of the analysis performed in step 29.

Analysis for multiple health care conditions takes place iteratively through the software at step 41, and the process just described, comprising steps 29, 31, 33, and 37 and producing charts and graphs 31 and reports 35, 39 is repeated, using the next health care condition definition to identify the population having that condition, followed by an analysis of the claims records for that population (a subset of the master files 25) under the defined quality care criteria for that next condition. After all the specified health care conditions have been processed in this manner, the reports for each condition are assembled 43 into a claims-based quality report 45 that is presented to the customer 47.

b. Detailed Analysis with Medical Records

Because it is recognized that a data base of health care claims, even if it includes data from medical professional services, hospital services and pharmacy services, may not have all the information available in other medical records maintained by the physician or other health care provider, the present invention provides as a supplement, additional methods to gather medical records and perform a more detailed analysis. In FIG. 2C at step 51, the system recognizes whether there is the need for detailed analysis. If no such need exists, no further data collection or analysis occurs. However, if a need for detailed analysis of any health care condition has been determined, then the population identified as having that condition is subjected to sampling 55 to determine for which enrollees additional medical records information will be collected. Both the master claims data files 27 and provider data 18 are used for this step. The determination of which members will have medical records collected for further analysis is based on varying criteria. For most health care conditions, medical records will be of interest for further study of the medical history if an enrollee has exhibited some unfavorable outcome or unexplained deviation from the quality of care criteria. Such enrollees are in greatest need of intervention and the quality of the care they have received or will receive is of greater significance. For instance, it may be desirable to focus detailed analysis on enrollees having more than a specified number of emergency room visits in a year or those for whom there is a deviation from the recommended drug regimen. To select these members, a further sampling definition is developed. It is implemented in software as a set of medical claims codes, hospital claims codes and pharmacy codes with specified Boolean relationships. If the member population remaining after application of these criteria is too large to be economic, it may be reduced in size by appropriate statistical sampling methods. The result of these steps is to define a subset of the population recognized as having the particular medical condition of interest to be subjected to further, more detailed study, based on the additional information available in medical records. Appendix A contains software used to set up the sample for which medical records data is collected and to identify the appropriate source for this data (i.e., provider location).

To initiate the gathering of medical records data, a request letter to a physician or other provider is generated. Selecting the appropriate provider to contact may be important, because there may be multiple sources of medical records, some of which will be inadequate for evaluation. The appropriate provider must be selected to receive the letter and be the unit for analysis. In some cases, a second source may also be selected. With the provider's consent, the medical records are abstracted 59 with a particular focus on events that relate to the particular health care condition under study, resulting in a completed medical records abstract form 61. This abstracted information is then entered into the system 63, via personal computer 150 to produce a medical record abstract data file 65. Additional and more highly clinically specific quality of care criteria are then used to analyze the medical record file, in a manner similar to the way the claims data was analyzed.

One difference is that the medical record may introduce additional data for medical, hospital or pharmacy activities that can be used to implement the quality care definition in the software. As can be seen, using the present invention means that only a relatively limited amount of medical records data need be assembled for health care quality analysis. Because a condition definition has been employed to identify an enrollee group of interest, only medical records for those enrollees having the condition under analysis are of interest. Moreover, those portions of the medical records relevant to the condition under analysis are abstracted. Thus, the volume of data to be analyzed is kept manageable and cost efficient.

Figure 2D:
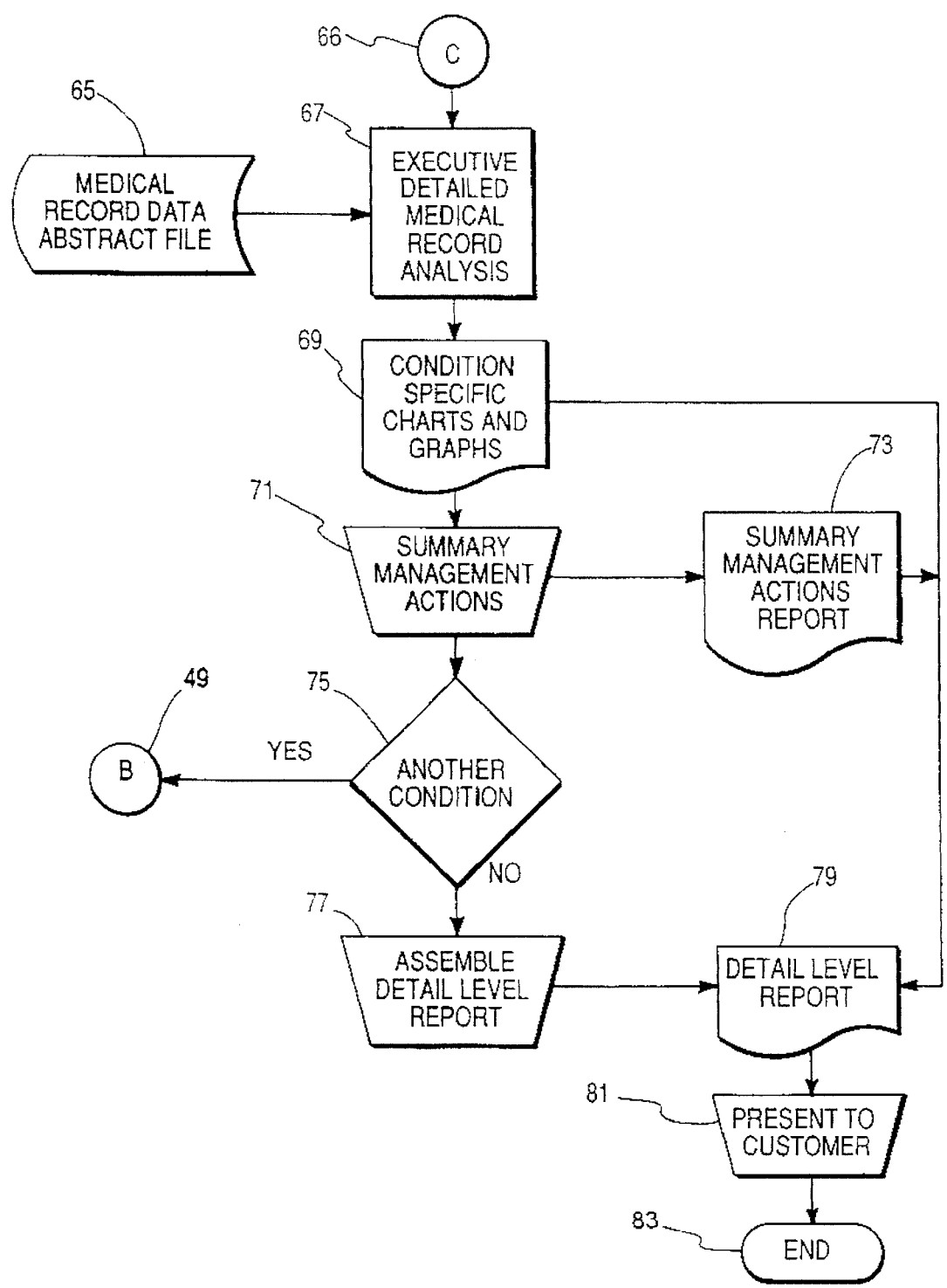

In FIG. 2D, it is shown that the result of the additional, detailed analysis is charts and graphs reporting statistically observed data in the population defined as having the health care condition of interest 69 and a report containing recommendations for actions to improve health care quality 71, 73. If detailed analysis of medical records is specified for multiple health care conditions, then the preceding steps are repeated until charts and graphs reporting statistically observed data 69 and a report containing recommendations for actions to improve health care quality 71, 73 are developed for each health care condition. (These are drawn from the same set of condition-specific quality management actions as discussed above in connection with steps 37, 39.) After all the specified health care conditions have been processed in this manner, the reports for each condition are assembled 77 into a detail level report 79 that is presented to the customer 81, and the process ends 83.

c. Examples for Particular Conditions

To further and more specifically explain the present invention, the data processing steps represented by steps 29 and 31 in FIG. 2B will be explained by way of two examples of specific health care conditions for which the present invention has been implemented.

EXAMPLE 1

Pediatric Asthma

To demonstrate further specifics about the present invention, reference is made to FIG. 3, which represents further details about the analysis and development of data for steps 29 and 31 in FIG. 2B when the defined health care condition to be studied is pediatric asthma. Still further details about the way in which pediatric asthma health care quality issues are analyzed in accordance with the present invention can be found in Appendix B, which is the SAS source code corresponding to steps 29 and 31 in FIGS. 2A–2D and to FIGS. 3A–3C.

The definition of the pediatric asthma condition used by the system is embodied in steps 303, 305, 307 and 309 of FIG. 3A, which determine the presence or absence of certain data in the claims data master file 25. If the claims data are coded in ICD-9 (International Code of Diseases, 9th Edition) form, the criteria may be expressed as follows. A member is defined as having pediatric asthma if he or she is under 19 years of age, is continuously enrolled for the year under study and meets one of the following criteria:

1. At least one hospitalization for asthma (IDC-9=493.xx); or
2. At least one emergency room visit for asthma (ICD-9=493.xx); or
3. Two or more doctor visits for asthma or asthma related conditions, provided that at least one of the visits is for asthma specifically, determined based on the following codes: asthma (493.xx), croup (464.4), acute bronchitis and bronchitis (466.xx), allergic rhinitis (477.xx), unspecified bronchitis (490.xx) and chronic bronchitis (491.xx); or
4. Two or more pharmacy claims for asthma related drugs, at least 45 days apart: beta-2 adrenic drugs; methyl xanthine drugs; and selected other bronchodilator related drugs (beclomethasone, cromolyn, flunsolide) (Criteria 1, 2 and 3 show the ICD-9 code that must be found in order for the criteria to be satisfied. The "xx" following these codes means that only the first three digits of these five digit codes are compared to determine a match.)

When the above pediatric asthma criteria are satisfied for any member, his or her name is added to the asthma member file list 313. The decision at step 311 ensures that the full claims data master file is searched for pediatric asthma cases. That is, the available records, which comprehensively cover claims records for medical professional services, claims records for hospital services and claims records for pharmaceutical prescriptions, are searched. It has been found that evidence of the asthma condition may appear in only one of these three categories of records. Yet a proper health care quality study of this condition must identify essentially all enrollees that have the condition, regardless of how the condition is reflected in the available claims records. For possible later analysis, a patient's record in the asthma member file list is flagged to indicate its inclusion in an adverse events and pharmaceuticals grouping. The asthma member file list 313 is then used in step 317 to build a new file that is a subset of the claims data master file and contains claims data only for members meeting the pediatric asthma definition. This asthma master file 319 is then used to calculate a variety of statistics on health care events and to develop charts and graphs to present the aggregated and calculated data. The calculations and the resulting reports and graphs are detailed at steps 321–351 in FIG. 3B.

As noted previously, the asthma member list file 313 is flagged to indicate an adverse events and pharmaceutical grouping. At step 353 of FIG. 3C the pharmaceutical asthma subset file is created and subjected to further processing at steps 355, 359, 363, 367. This processing results in the calculation of aggregate statistics of various kinds having to do with prescription drug use for the members identified as pediatric asthma patients. The calculations and the resulting charts are detailed at steps 353–371 of FIG. 3C.

Shown at Appendix C are examples of the kinds of reports and charts and graphs developed by the present invention when analyzing the pediatric asthma condition. These reports reflect an actual analysis from a health maintenance organization (the identity has been deleted) and include:

General explanation of the pediatric asthma quality review

Chart of demographics of children with asthma

Pie graph of age distribution of pediatric asthma patients

Bar graph of frequency of adverse events

Chart of frequency of emergency room visits

Chart of frequency of hospital admissions

Bar graph of percent of children having an annual office visit for asthma, differentiated by adverse event occurrence Bar graph of average number of office visits Chart of pulmonary function testing Bar graph of influenza immunization Chart of serum theophyline level monitoring Charts of use of beta-agonists, cromolyn, theophylline and barbituates Summary of key statistical findings Quality management actions recommendations, including proposed medical record flow sheet for pediatric asthma patients In the present instance, the management actions recommendations include all those that are part of the condition-specific set of action recommendations for pediatric asthma. In a report for another customer, only a subset of these might appear, because fewer corrective actions are necessary.

EXAMPLE 2

Caesarian Section

To demonstrate further specifics about the present invention, reference is made to FIGS. 4A–4B, which represents further details about the analysis and development of data for steps 29 and 31 in FIG. 2B when the defined health care condition to be studied is caesarian sections. Still further details about the way in which caesarian section health care quality issues are analyzed in accordance with the present invention can be found in Appendix D, which is the SAS source code corresponding to steps 29 and 31 and to FIGS. 4A–4B.

The definition of the caesarian section condition used by the system is embodied in steps 405–421, which test for certain data in the claims data master file 403. At steps 405 and 407 a subset of the master file is created that includes all enrollees who were pregnant and thus potential candidates for a caesarian section birth (C-section). From this subject enrollees having miscarriages are deleted 409, producing a smaller working C-section file 411. This file is divided 413 into a C-section births file 415 and a vaginal births file 417. These two files are then merged 419 to produce the births file 421.

Although there is no agreement on an ideal C-section birth rate that would provide a health care quality measure, there is agreement that a C-section birth rate above the national average could indicate that health care providers are performing inappropriate C-section procedures. Accordingly, the health care quality definition implemented at steps 425–447 of FIG. 4C involves calculation of overall C-section birth rates 425, charting that rate by comparison to the national norm 427 and then charting C-section birth rates by age group 429 and by hospital 431–445. Finally, a "trombone chart" 441 is produced that shows the C-section birth rate for individual hospitals, plotted against the average for all hospitals in the analysis and a curve showing the upper 95% confidence bound (based on statistical measures adjusting for sample size).

Shown at Appendix E are examples of the kinds of reports and charts and graphs developed by the present invention when analyzing the C-section condition. These reports reflect an actual analysis from a health maintenance organization (the identity has been deleted) and include:

General explanation of C-section quality review

Bar graph of C-section rate vs. national norm

Bar graph of C-section rates by age

"Trombone graph" of C-section rates

Chart of C-section rates by hospital

Summary of key statistical findings

Quality management action recommendations

C-section medical record abstraction form and instructions (for more detailed analysis)

To perform a detailed analysis beyond the level of claims-based quality evaluation, the medical record may be obtained. This would usually be performed in specific populations where the overall observed C-section rate was higher than expected. Therefore, the objective would be to determine whether there were specific indications of medical need for a C-section justifying that the procedure was performed. Appendix E contains the medical record abstraction form and instructions. This data obtained from the medical record would be entered and analyzed in the software of the present invention.

d. Summary

As can be seen from the preceding, the present invention involves a data processing system and analytic method that utilizes multiple sources of health care data to evaluate health care quality. The invention initially utilizes the health care claims data accumulated by a health care benefit organization as its enrollees utilize health care benefits. Specific health care conditions of interest are defined in terms of the claims data and these definitions are implemented in software logic to allow a subset of enrollees to be identified as having the health care condition of interest. The health care claims data for this subset are then analyzed in terms of health care quality criteria, developed from multiple expert clinical sources. These criteria are also defined in terms of the claims data and implemented in software that develops statistical measures of health care quality. If desired, additional medical record data can be collected for the specific portion of the subset of enrollees identified as having the condition of interest. These additional medical records data supplement the claims data and allow additional, more detailed health care quality criteria to be defined. These criteria are analyzed against the additional data. Further statistical measures of health care quality can then be developed. After analysis of the original claims data and after analysis of the additional medical record data, descriptive and evaluative reports and recommendations on improving health care quality are developed and provided.

The invention combines at least three primary advantages to improve over the prior art. First, it permits use to be made of the large claims data bases that are maintained by health care organizations, which in most cases are already in computerized form, permitting large scale health care quality analysis to be performed based on this claims data. Second, it limits the laborious and expensive task of assembling medical records data for quality analysis to a population that has been screened and selected as having specific potential need for quality improvement (and is thus smaller than the entire universe of enrollees). Third, by enabling evaluation of health care quality to be performed in a more standardized and efficient manner, through use of distinctly identified data elements in conjunction with discretely defined clinical algorithms, it permits quality assessment on a larger and more geographically distributed population base and the production of information sought by managers, purchasers, providers and regulators of health care.

Appendixes A–E contain the program source code that implement the embodiment described above.

LIST OF APPENDICES

APP. A - Software to set up sample for medical records collection

APP. B - Software for pediatric asthma screening

APP. C - Pediatric asthma report

APP. D - Software for C-section screening

APP. E - C-section report

```
LIBNAME SLC 'D:\SASDATA\SLC';

%LET MEMBIN=SLC.ASMVIS;             /* INPUT DATASET (MEMBER LIST) */
%LET MROUT='F:\SLCASTH.DIF';        /* OUTPUT ASCII FILE OF MEDICAL RECORDS TO BE ABSTRACTED
                                       ENCLOSE IN SINGLE QUOTES PATH FILENAME .DIF */
%LET DRCLM=SLC.SLCDR;               /* DATASET CONTAINING DR CLAIMS FOR INPUT DATASET MEMBERS */
%LET PROVTABL=SLC.PROVIDER;         /* DATASET CONTAINING PROVIER NAMES AND ADDRESSES */
%LET ENROLL=SLC.ENROLL;             /* DATASET CONTAINING MEMBER NAMES AND ENROLLMENT */
%LET UP_LMT=50;                     /* MAXIMUM NUMBER OF MEMBERS SELECTED */
%LET HMO=SLC;                       /* THREE LETTER PLAN IDENTIFIER */
%LET BEG='493';                     /* BEGINNING ICDCODE TO IDENTIFY DOCTOR PROVIDING CARE */
%LET END='4939';                    /* ENDING ICDCODE TO IDENTIFY DOCTOR PROVIDING CARE */
%LET DRCODE='01','02','04','12','39';
                                    /* PROVIDER TYPES TO IDENTIFY PRIMARY DOCTOR PROVIDING CARE
                                       MULTIPLE CODES NEED TO BE ENTERED IN SINGLE
                                       QUOTES SEPARATED BY COMMAS */
%LET HOSP=%STR('50' <= SUBSTR(PROVID,1,2) <= '55' AND SITECODE=4);
                                    /* LOGIC IDENTIFYING INPATIENT HOSPITAL */
%LET ERV=%STR('50' <= SUBSTR(PROVID,1,2) <= '55' AND
              (SITECODE=8 OR SITECODE=10) OR SUBSTR(PROVID,1,2)='67');
                                    /* LOGIC IDENTIFYING EMERGENCY ROOM VISIT */
%LET ICD3='466','477','490','491','493';
                                    /* ICDCODES TO IDENTIFY DX RELATED HOSPITALS
                                       MULTIPLE CODES NEED TO BE ENTERED IN SINGLE
                                       QUOTES SEPARATED BY COMMAS */
%LET ICD4='4644';                   /* ICDCODES TO IDENTIFY DX RELATED HOSPITALS
                                       MULTIPLE CODES NEED TO BE ENTERED IN SINGLE
                                       QUOTES SEPARATED BY COMMAS */

/* Selects eligible members for the random selection */
DATA ELGMEMB;
  SET KMEMBIN(KEEP=MEMBID HOSPCNT ERVCNT);
  IF HOSPCNT OR ERVCNT >= 2;
RUN;

/* Selects a random sample of members from the input dataset */
DATA RANDOM1(KEEP=READIT);
  SAMPSIZE=&UP_LMT;
  DO WHILE(SAMPSIZE>0);
    READIT+1;
    IF LASTOBS <= &UP_LMT THEN DO;
      SET ELGMEMB NOBS=LASTOBS;
      READIT=_N_;OUTPUT;
    END;
    ELSE DO;
      SAMPSIZE=&UP_LMT;
      DO WHILE(SAMPSIZE>0);
        IF UNIFORM(0)<SAMPSIZE/TOTOBS THEN
          DO;
            OUTPUT;
            SAMPSIZE=SAMPSIZE-1;
          END;
        TOTOBS=TOTOBS-1;
      END;
      STOP;
    END;
    SET ELGMEMB POINT=_N_ NOBS=TOTOBS;
RUN;
DATA MEMBOUT(KEEP=MEMBID);
  SET RANDOM1;
  SET ELGMEMB POINT=READIT;
RUN;
PROC DATASETS LIBRARY=WORK NOLIST;
  DELETE ELGMEMB RANDOM1;
```

APPENDIX A

```
RUN;

PROC SORT DATA=MEMBOUT;BY MEMBID;RUN;

/* Selects Dr claims only for members in random sample */
DATA DRCLMS(KEEP=MEMBID FROMDATE CPTDATE THRUDATE PROVID ICDCODE SITECODE CPTCODE);
   MERGE MEMBOUT(IN=A) &DRCLM;
   BY MEMBID;
   IF A;
RUN;

PROC SORT DATA=DRCLMS;BY MEMBID CPTDATE PROVID ICDCODE;RUN;

/* Eliminates duplicate diagnoses per patient per doctor per day */
DATA UNQORDX UNQDR;
   SET DRCLMS;
   BY MEMBID CPTDATE PROVID ICDCODE;
   IF FIRST.ICDCODE AND SUBSTR(PROVID,1,2) IN (&DRCODE)
      AND (SUBSTR(ICDCODE,1,3) IN (&ICD3) OR SUBSTR(ICDCODE,1,4) IN (&ICD4))
      THEN OUTPUT UNQORDX;
   IF FIRST.PROVID AND SUBSTR(PROVID,1,2) IN (&DRCODE) THEN OUTPUT UNQDR;
RUN;

PROC PRINT DATA=UNQORDRX(OBS=30);
   VAR MEMBID ICDCODE CPTCODE CPTDATE PROVID;
   TITLE "UNIQUE DIAGNOSES FOR EACH &HMO MEMBER";RUN;
PROC PRINT DATA=UNQDR(OBS=30);
   VAR MEMBID ICDCODE CPTCODE CPTDATE PROVID;
   TITLE "UNIQUE DOCTORS FOR EACH &HMO MEMBER";RUN;

*PROC DATASETS LIBRARY=WORK NOLIST;
* DELETE DRCLMS;*RUN;

/* Identifies the best location/doctor for medical record abstraction */

PROC FREQ DATA=UNQDR;
   TABLE PROVID / NOPRINT OUT=DRDXFRQ;
   BY MEMBID;
RUN;
PROC FREQ DATA=UNQDR;
   TABLE PROVID / NOPRINT OUT=DRFRQ;
   BY MEMBID;
RUN;
DATA UNQDR;
   SET DRFRQ(DROP=PERCENT);BY MEMBID;
   IF LAST.MEMBID;
RUN;
DATA UNQDRDX;
   SET DRDXFRQ(DROP=PERCENT);BY MEMBID;
   IF LAST.MEMBID;
RUN;
PROC SORT DATA=DRDXFRQ;BY MEMBID COUNT;RUN;
PROC SORT DATA=DRFRQ;BY MEMBID COUNT;RUN;

DATA SELECTOR UNSELMMB;
   MERGE MEMBOUT UNQDR UNQDRDX;
   BY MEMBID;
   IF PROVID=' ' THEN OUTPUT UNSELMMB;
   ELSE OUTPUT SELECTOR;
RUN;
```

```
/* Creates the provider number, address and phone from the SQL provider table*/
DATA PROV(KEEP=PROVID PHYSNAME PHYSADDR PHYSCITY PHYSZIP PHYSPHON)
    POBOX;
    SET &PROVTABL;
    PHYSNAME=NAME; PHYSCITY=CITY; PHYSZIP=ZIP;
    IF MAILING NE ' ' THEN DO;
        IF (LENGTH(MAILING) > 15
        OR (INDEX(MAILING, 'PO BOX ')>0 AND INDEX(MAILING, 'P.O. BOX ')=0))
        THEN PHYSADDR=MAILING;ELSE PHYSADDR=OFFICE;
        IF INDEX(MAILING,'BILLING') NE 0 AND OFFICE NE ' ' THEN
        IF INDEX(OFFICE,'BILLING')=0 THEN PHYSADDR=OFFICE;ELSE PHYSADDR=MAILING;
    END;
    ELSE DO;
        IF OFFICE NE ' ' THEN PHYSADDR=OFFICE;ELSE PHYSADDR=MAILING;
    OUTPUT POBOX;
    END;
    PHYSPHON='('|| PUT(AREACODE,3.)||')'||SUBSTR(PUT(PHONE,7.),1,3)
        ||'-'||SUBSTR(PUT(PHONE,7.),4,4);
    DROP CITY ZIP NAME AREACODE PHONE;
    LABEL PROVID='PROVIDER NUMBER';
    OUTPUT PROV;
RUN;

PROC SORT DATA=PROV;BY PROVID;RUN;
PROC SORT DATA=SELECTOR;BY PROVID;RUN;

DATA MROUT;
    MERGE SELECTOR(IN=A) PROV;
    BY PROVID;
    IF A;
RUN;

PROC SORT DATA=MROUT;BY MEMBID;RUN;

DATA MEMBMR;
    MERGE MROUT(IN=A) &ENROLL(KEEP=MEMBID MEMBNAME BIRTHDTE);
    BY MEMBID;
    IF A;
RUN;

/* Identifies hospital numbers for each member */
DATA MEMBHOSP;
    MERGE DRCLMS MEMBMR(IN=A RENAME=(PROVID=PHYSID));
    BY MEMBID;
    IF A;
    IF (2HOSP OR SERV);
    AND (SUBSTR(ICDCODE,1,3) IN (&ICD3) OR SUBSTR(ICDCODE,1,4) IN (&ICD4));
    HOSPID=PROVID;
    DROP SITECODE ICDCODE CPTCODE CPTDATE;
RUN;

PROC SORT DATA=MEMBHOSP;BY MEMBID HOSPID FROMDATE THRUDATE;RUN;
PROC PRINT DATA=MEMBHOSP(OBS=40);TITLE 'MEMBERS WITH MULITPLE HOSPITAL RECORDS';RUN;
/* Identifies range of hospitalizations or ER visits */
DATA MEMBMR(DROP=ADMT COUNT FROMDATE THRUDATE);
    DO UNTIL(LAST.HOSPID);
        SET MEMBHOSP;BY MEMBID HOSPID FROMDATE;RETAIN ADMT ADMIT1-ADMIT16;
        IF FIRST.HOSPID THEN DO;
            ADMT=FROMDATE;COUNT+1;ADMIT1=FROMDATE;
        END;
        IF FROMDATE > ADMT THEN DO;
            COUNT+1;
            SELECT (COUNT);
```

```
              WHEN (2) DO;ADMIT2=FROMDATE;ADMIT=FROMDATE;END;
              WHEN (3) DO;ADMIT3=FROMDATE;ADMT=FROMDATE;END;
              WHEN (4) DO;ADMIT4=FROMDATE;ADMIT=FROMDATE;END;
              WHEN (5) DO;ADMIT5=FROMDATE;ADMIT=FROMDATE;END;
              WHEN (6) DO;ADMIT6=FROMDATE;ADMIT=FROMDATE;END;
              OTHERWISE;
           END;
        END;
        IF LAST.HOSPID THEN DO;
           COUNT=0;
           FORMAT ADMIT1-ADMIT6 MMDDYY8.;OUTPUT;
           ADMIT1=.;ADMIT2=.;ADMIT3=.;ADMIT4=.;ADMIT5=.;ADMIT6=.;
        END;
     RUN;

PROC PRINT DATA=MEMBMR(OBS=40);TITLE 'MEMBERS WITH HOSPITALIZATION VISITS';RUN;

PROC SORT DATA=MEMBMR;BY HOSPID;RUN;

/* Identifies hospital names and addresses */
     DATA MEMBHOSP;
        MERGE MEMBMR(IN=A) PROV(RENAME=(PROVID=HOSPID PHYSNAME=HOSPNAME PHYSADDR=HOSPADDR
                                       PHYSCITY=HOSPCTY PHYSPHON=HOSPPHON PHYSZIP=HOSPZIP));
        BY HOSPID;
        IF A;
     RUN;

PROC SORT DATA=MEMBHOSP;
        BY PHYSZIP PHYSADDR PHYSNAME MEMBID;
     RUN;

DATA MRABST(KEEP=PHYSZIP PHYSADDR PHYSCTYZ MEMBERID MEMBNAME OBSNUM PHYSPHON PHYSNAME
                      MEMBDOB DR_NAME HOSPNAME HOSPADDR HOSPCTYZ HOSPPHON ADMIT1-ADMIT6);
        SET MEMBHOSP;

X=INDEXC(MEMBNAME,',');
     Y=INDEXC(PHYSNAME,',');
     Z=INDEXC(PHYSNAME,'.');
     Q=INDEXC(MEMBNAME,'.');
     R=INDEXC(PHYSNAME,'.');

IF Q>0 THEN NAME=TRANSLATE(MEMBNAME,' ','.');
     IF R>0 THEN PHYSNAME=TRANSLATE(PHYSNAME,' ','.');

OBSNUM="RHMO"||'/'||TRIM(PUT(_N_,4.));
     IF NAME=SUBSTR(PHYSNAME,1,(Y-1));
     V=INDEX(DR_NAME,'*RESIDENT');
     W=INDEX(PHYSNAME,'*RESIDENT');

IF (Z > 0) THEN
        PHYSNAME=SUBSTR(PHYSNAME,(Z+2),(LENGTH(PHYSNAME)-(Z+1)))||' '||SUBSTR(PHYSNAME,1,(Z-1));
     ELSE
        PUT OBSNUM PHYSNAME;

IF (V > 0) THEN
        DR_NAME=SUBSTR(DR_NAME,1,(V-1));

IF SUBSTR(LEFT(DR_NAME),1,2)='DE' THEN PUT OBSNUM PHYSNAME;
     IF SUBSTR(LEFT(DR_NAME),1,2)='LA' THEN PUT OBSNUM PHYSNAME;
     IF SUBSTR(LEFT(DR_NAME),1,2)='LE' THEN PUT OBSNUM PHYSNAME;
     IF SUBSTR(LEFT(DR_NAME),1,4)='VON ' THEN PUT OBSNUM PHYSNAME;
     IF SUBSTR(LEFT(DR_NAME),1,3)='VAN' THEN PUT OBSNUM PHYSNAME;

IF (W > 0) THEN
        PHYSNAME=SUBSTR(PHYSNAME,1,W-1)||SUBSTR(PHYSNAME,W+9,LENGTH(PHYSNAME)-W);
```

```
IF SUBSTR(LEFT(MEMBNAME),1,2)='DE' THEN PUT OBSNUM MEMBNAME;
IF SUBSTR(LEFT(MEMBNAME),1,2)='LA' THEN PUT OBSNUM MEMBNAME;
IF SUBSTR(LEFT(MEMBNAME),1,2)='LE' THEN PUT OBSNUM MEMBNAME;
IF SUBSTR(LEFT(MEMBNAME),1,4)='VON ' THEN PUT OBSNUM MEMBNAME;
IF SUBSTR(LEFT(MEMBNAME),1,3)='VAN' THEN PUT OBSNUM MEMBNAME;

PT_NAME=SUBSTR(MEMBNAME,(X+2),(LENGTH(MEMBNAME)-(X+1)))||', '||SUBSTR(MEMBNAME,1,(X-1));
MEMBNAME=PT_NAME;
MEMBERID=SUBSTR(MEMBID,1,5)||'-'||SUBSTR(MEMBID,6,9)||'-'||SUBSTR(MEMBID,15,2);
PHYSCTYZ=TRIM(PHYSCITY)||', '||PHYSZIP;
HOSPCTYZ=TRIM(HOSPCITY)||', '||HOSPZIP;
MEMBDOB=PUT(BIRTHDTE,MMDDYY8.);
RUN;

FILENAME BHMO &NROUT;
PROC DIF DIF=&HMO DATA=MRABST;
RUN;
```

```
%LET.DR=PVD.DOCTOR;
%LET RX=PVD.PHARM;
%LET AVIS=PVD.ASMVIS;
%LET YR=90;
%LET YR19=71;
%LET PLAN=PHYSICIANS HEALTH PLAN OF OCEAN STATE - 1990;

OPTIONS NONUMBER NODATE;

PROC FORMAT;
   VALUE AGEFMT
      0-35   ='0-2'
      36-83  ='3-6'
      84-143 ='7-12'
      144-239='13-19';
RUN;

DATA DR1(DROP=EFFECTDT EXPIREDT PROVID);
SET &DR(DROP=MEMBZIP AUDNBR AUDSUB THRUDATE FDDATE POSTDATE SEX
        PARCODE REFNBR AMTCLM AMTPAID AUTHSUB);
WHERE (BIRTHDTE>="01JAN&YR19"D)AND (EFFECTDT<="01JAN&YR"D) AND (EXPIREDT>="31DEC&YR"D);
PROV=INPUT(SUBSTR(PROVID,1,2),2.);
X=INTCK('MONTH',BIRTHDTE,MDY(6,30,&YR));
Y=PUT(X,AGEFMT.);
AGE=ROUND(X/12);
ICDCODE=COMPRESS(ICDCODE,'.');
ICD=SUBSTR(ICDCODE,1,3);
RUN;

DATA RX1(DROP=EFFECTDT EXPIREDT PROVID);
SET &RX(DROP=MEMBZIP AUDNBR PHARMID FDDATE PRESCDEA NDCCODE
        RXNBR NEWREFIL AMTCLM CALCCOST AMTPAID COPAY DISPFEE DAWCODE
        REASONCD DRUGNAME DRUGSTR);
WHERE (BIRTHDTE>="01JAN&YR19"D)AND (EFFECTDT<="01JAN&YR"D) AND (EXPIREDT>="31DEC&YR"D);
PROV=INPUT(SUBSTR(PROVID,1,2),2.);
X=INTCK('MONTH',BIRTHDTE,MDY(6,30,&YR));
Y=PUT(X,AGEFMT.);
AGE=ROUND(X/12);
RUN;

DATA HOSP1(KEEP=MEMBID HOSP MEMBSEX)
     DRAST1;
SET DR1;
HOSP=0;
IF ICD='493' THEN
   IF SITECODE IN (4,8) THEN DO;
      IF 50<=PROV<=55 THEN HOSP=1;
      IF PROV=39 THEN HOSP=1;
   END;
   IF PROV=67 THEN HOSP=1;
IF HOSP THEN OUTPUT HOSP1;
IF ICD IN ('493','466','477','490','491')OR SUBSTR(ICDCODE,1,4)='4644'THEN DO;
   IF PROV IN (1,2,4,10,12,48)THEN
      IF SITECODE=1 THEN
         IF ('90000'<=CPTCODE<='90080')OR ('90600'<=CPTCODE<='90643')THEN OUTPUT DRAST1;
      IF SITECODE=8 THEN
         IF 50<=PROV<=55 THEN OUTPUT DRAST1;
      IF PROV=67 THEN OUTPUT DRAST1;
      IF SITECODE IN (8,4) THEN
         IF PROV=39 THEN OUTPUT DRAST1;
```

APPENDIX B

```
END;
RUN;

PROC SORT DATA=HOSP1;
BY MEMBID;
RUN;

DATA HOSP1;
SET HOSP1;
BY MEMBID;
IF FIRST.MEMBID;
RUN;

PROC SORT DATA=DRAST1;
BY MEMBID ICD CPTDATE;
RUN;

DATA DRASTREL(DROP=FLAG1 FLAG2 CPTDT1);
RETAIN FLAG1 FLAG2 CPTDT1;
SET DRAST1;
BY MEMBID ICD;
IF FIRST.MEMBID THEN DO;
   FLAG1=0;
   FLAG2=0;
   CPTDT1=CPTDATE;
   END;
IF ICD='493' THEN FLAG2=1;
IF (ABS(INTCK('DAY',CPTDT1,CPTDATE)))>=30 THEN FLAG1=1;
IF LAST.MEMBID AND FLAG1 AND FLAG2 THEN DO;
   DRASTH=1;
   OUTPUT DRASTREL;
   END;
RUN;

PROC SORT DATA=RX1 OUT=RX;
WHERE THERCLS IN (151100,151200) OR GENCODE IN (775,2263,3523);
BY MEMBID FILLDATE;
RUN;

DATA RX1A(KEEP=MEMBID RX MEMBSEX);
RETAIN FLAG CPTDT1;
SET RX;
BY MEMBID;
IF FIRST.MEMBID THEN DO;
   FLAG=0;
   CPTDT1=FILLDATE;
   END;
IF (ABS(INTCK('DAY',CPTDT1,FILLDATE)))>=34 THEN FLAG=1;
IF LAST.MEMBID AND FLAG=1 THEN DO;
   RX=1;
   OUTPUT RX1A;
   END;
RUN;

DATA ASMAID(KEEP=MEMBID DRASTH HOSP RX MEMBSEX);
MERGE HOSP1(IN=A) DRASTREL(IN=B) RX1A(IN=C);
BY MEMBID;
IF A OR B OR C;
IF HOSP=. THEN HOSP=0;
IF DRASTH=. THEN DRASTH=0;
```

```
IF RX=. THEN RX=0;
IF FIRST.MEMBID THEN OUTPUT;
RUN;

PROC FREQ DATA=ASMAID;
TABLES HOSP DEASTH RX;
RUN;

DATA GROUP1;
MERGE ASMAID(IN=A) RX1(IN=B);
BY MEMBID;
IF A=B;
IF RX AND FIRST.MEMBID;
GROUPA=RX;
RUN;

DATA GROUP2;
MERGE ASMAID(IN=A) DR1(IN=B);
BY MEMBID;
IF A=B;
ICDCODE=COMPRESS(ICDCODE,'.');
GROUPB=1;
IF (ICD IN ('493','466','477','490','491') OR SUBSTR(ICDCODE,1,4)='4644') THEN DO;
   IF SITECODE=4 THEN
      IF 50<=PROV<=55 THEN OUTPUT;
   IF SITECODE IN (8,4) THEN
      IF PROV=39 THEN OUTPUT;
   IF SITECODE=8 THEN
      IF 50<=PROV<=55 THEN OUTPUT;
   IF PROV=67 THEN OUTPUT;
END;
ELSE
   IF ((SUBSTR(ICDCODE,1,4) IN ('9952','9620','9670','9757') OR
      ICDCODE IN ('E9320','E9370','E9457')) THEN OUTPUT;
RUN;

PROC SORT DATA=GROUP2;
BY MEMBID;
RUN;

DATA GROUP2;
SET GROUP2;
BY MEMBID;
IF FIRST.MEMBID THEN OUTPUT;
RUN;

DATA GROUPS(KEEP=MEMBID GROUPA GROUPB GROUPC);
MERGE GROUP1(IN=A) GROUP2(IN=B) ASMAID(IN=C);
BY MEMBID;
IF A OR B OR C;
IF GROUPA=. THEN GROUPA=0;
IF GROUPB=. THEN GROUPB=0;
IF GROUPA OR GROUPB THEN GROUPC=0;
ELSE GROUPC=1;
RUN;

PROC FREQ DATA=GROUPS;
TABLE GROUPA*GROUPB;
TABLE GROUPC;
RUN;
```

```
DATA ASMDR1 ASMADR2(KEEP=MEMBID MEMBSEX AGE Y ICDCODE PROV
     SITECODE GROUPA GROUPC GROUPB AUTHNBR FROMDATE);
MERGE GROUPS(IN=A) DR1(IN=B);
BY MEMBID;
IF A=B;
IF FIRST.MEMBID THEN OUTPUT ASMADR2;
OUTPUT ASMDR1;
RUN;

DATA ASMRX1 ASMARX2(KEEP=MEMBID MEMBSEX AGE Y PROV GROUPA GROUPC GROUPB);
MERGE GROUPS(IN=A) RX1(IN=B);
BY MEMBID;
IF A=B;
IF FIRST.MEMBID THEN OUTPUT ASMARX2;
OUTPUT ASMRX1;
RUN;

DATA GROUPS;
MERGE ASMADR2(IN=A) ASMARX2(IN=B);
BY MEMBID;
IF A OR B;
IF GROUPA=. THEN GROUPA=0;
IF GROUPB=. THEN GROUPB=0;
IF GROUPC=. THEN GROUPC=0;
RUN;

DATA _NULL_;
SET GROUPS END=LASTOBS;
IF GROUPB THEN ADV+1;
ELSE NADV+1;
IF LASTOBS THEN DO;
   CALL SYMPUT('ADVER',COMPRESS(PUT(ADV,5.),''));
   CALL SYMPUT('NADVER',COMPRESS(PUT(NADV,5.),''));
END;
RUN;

OPTIONS NONUMBER NODATE LS=79;

PROC FORMAT;
   VALUE VIS
          0='0 VISITS'
          1='1 VISIT'
          2='2 VISITS'
       3-HIGH='3+ VISITS';

VALUE CLM
          0='0 CLAIMS'
          1='1 CLAIM'
          2='2 CLAIMS'
          3='3 CLAIMS'
          4='4 CLAIMS'
          5='5 CLAIMS'
          6='6 CLAIMS'
          7='7 CLAIMS'
          8='8 CLAIMS'
          9='9 CLAIMS';

VALUE VISA
          0='0 VISITS'
          1='1 VISIT'
```

```
           2='2 VISITS'
           3='3 VISITS'
           4='4 VISITS'
           5='5 VISITS'
           6='6 VISITS'
           7='7 VISITS'
           8='8 VISITS'
           9='9 VISITS';

VALUE VISB
       0='0 VISITS'
       1-5='1-5 VISITS'
       6-10='6-10 VISITS'
       11-20='11-20 VISITS'
       20-HIGH='>20 VISITS';

VALUE VAC
       0='NOT VACCINATED'
       1='VACCINATED';

VALUE DOS
       13,25='INHALANT FORM'
       27='RECTAL FORM'
       14='INJECTABLE FORM'
       2-3,8-12,20-23,
       29-30,41='ORAL FORM';

RUN;

PROC SORT DATA=ASMDR1;
BY MEMBID CPTCODE CPTDATE;
RUN;

DATA ERV;
RETAIN ERV;
SET ASMDR1;
BY MEMBID CPTCODE CPTDATE;
IF FIRST.MEMBID THEN ERV=0;
ICD=SUBSTR(ICDCODE,1,3);
IF FIRST.CPTDATE THEN
    IF ICD IN ('493','466','477','490','491')OR SUBSTR(ICDCODE,1,4)='4644'THEN DO;
       IF SITECODE IN (8,4) THEN
          IF PROV=39 THEN ERV+1;
       IF PROV=67 THEN ERV+1;
       IF SITECODE=8 THEN
          IF 50<=PROV<=55 THEN ERV+1;
       END;
IF LAST.MEMBID THEN OUTPUT;
RUN;

DATA ERV;
MERGE GROUPS(IN=A) ERV(IN=B);
BY MEMBID;
IF A OR B;
IF ERV=. THEN ERV=0;
RUN;

PROC FREQ DATA=ERV;
TABLES ERV /OUT=ERVAFRQ;
LABEL ERV='NUMBER OF VISITS';
```

```
FORMAT ERV VIS.;
TITLE2 'EMERGENCY ROOM VISITS';
TITLE3 "TOTAL POPULATION";
RUN;

PROC SORT DATA=ASMDR1 OUT=TMP1;
WHERE ((50<=PROV<=55) AND SITECODE=4);
BY MEMBID AUTHNBR FROMDATE;
RUN;

DATA TMP1;
SET TMP1;
BY MEMBID AUTHNBR FROMDATE;
IF FIRST.FROMDATE;
RUN;

PROC SORT DATA=TMP1;
BY MEMBID FROMDATE AUTHNBR;
RUN;

DATA HOSP;
SET TMP1;
BY MEMBID FROMDATE AUTHNBR;
IF FIRST.FROMDATE;
RUN;

DATA HOSP(KEEP=MEMBID HOSP);
RETAIN HOSP;
SET HOSP;
BY MEMBID AUTHNBR FROMDATE;
IF FIRST.MEMBID THEN HOSP=0;
IF FIRST.FROMDATE THEN
    IF ICD IN ('493','466','477','490','491')OR SUBSTR(ICDCODE,1,4)='4644'THEN
        IF 50<=PROV<=55 THEN
            IF SITECODE=4 THEN HOSP+1;
IF LAST.MEMBID THEN OUTPUT;
RUN;

DATA HOSP;
MERGE GROUPS(IN=A) HOSP(IN=B);
BY MEMBID;
IF A OR B;
IF HOSP=. THEN HOSP=0;
RUN;

PROC FREQ DATA=HOSP;
TABLES HOSP /OUT=HOSPAFRQ;
LABEL HOSP='NUMBER OF VISITS';
FORMAT HOSP VIS.;
TITLE2 'HOSPITALIZATION VISITS';
TITLE3 "TOTAL POPULATION";
RUN;

DATA &AVIS(KEEP=MEMBID HOSPCNT ERVCNT);
MERGE HOSP(IN=A RENAME=(HOSP=HOSPCNT))ERV(IN=B RENAME=(ERV=ERVCNT));
BY MEMBID;
IF A=B;
RUN;

DATA OFFVIST(KEEP=MEMBID Y VISITS);
```

```
RETAIN VISITS;
SET ASMDR1;
BY MEMBID CPTCODE CPTDATE;
IF FIRST.MEMBID THEN VISITS=0;
IF FIRST.CPTDATE THEN
    IF SITECODE=1 THEN
        IF ('90000'<=CPTCODE<='90080')OR ('90600'<=CPTCODE<='90643')THEN VISITS+1;
IF LAST.MEMBID THEN OUTPUT;
RUN;

DATA OFFVIST;
MERGE GROUPS(IN=A) OFFVIST(IN=B);
BY MEMBID;
IF A OR B;
IF VISITS=. THEN VISITS=0;
RUN;

TITLE1 'AMBULATORY CARE MEASURES';

PROC FREQ DATA=OFFVIST;
TABLES VISITS /OUT=OFFV2FRQ;
WHERE GROUPB=1;
FORMAT VISITS VISA.;
LABEL VISITS='NUMBER OF VISITS';
TITLE2 'MD OFFICE VISITS';
TITLE3 'ALL OF GROUP 2';
RUN;

DATA PFT(KEEP=MEMBID Y CPTCODE CPTDATE SCPT PCPT);
SET ASMDR1;
RETAIN FLAG;
BY MEMBID CPTCODE CPTDATE;
IF FIRST.MEMBID THEN FLAG=0;
SCPT=('94010'<=CPTCODE<='94070');
PCPT=CPTCODE IN ('94150','94160','94375');
IF SCPT OR PCPT THEN FLAG=1;
IF PCPT AND FIRST.CPTDATE THEN OUTPUT;
IF SCPT AND FIRST.CPTDATE THEN OUTPUT;
IF LAST.MEMBID AND FLAG=0 THEN OUTPUT;
RUN;

DATA PFT;
SET PFT;
RETAIN VISITS 0;
BY MEMBID CPTCODE CPTDATE;
IF FIRST.MEMBID THEN VISITS=0;
IF FIRST.CPTDATE AND SCPT OR PCPT THEN VISITS+1;
IF LAST.MEMBID THEN OUTPUT;
RUN;

DATA PFT;
MERGE GROUPS(IN=A) PFT(IN=B);
BY MEMBID;
IF A OR B;
IF VISITS=. THEN VISITS=0;
RUN;

PROC FREQ DATA=PFT;
TABLES VISITS /OUT=PFT2FRQ;
WHERE GROUPB=1;
```

```
FORMAT VISITS VIS.;
LABEL VISITS='SPIROMETRY/PEAK FLOW VISIT';
TITLE2 'PULMONARY FUNCTION TESTS';
TITLE3 'ALL OF GROUP 2';
RUN;

DATA FLU(KEEP=MEMBID Y VACC);
RETAIN VACC;
SET ASMDR1;
BY MEMBID;
IF FIRST.MEMBID THEN VACC=0;
IF CPTCODE='90724' THEN VACC=1;
IF LAST.MEMBID THEN OUTPUT;
RUN;

DATA FLU;
MERGE GROUPS(IN=A) FLU(IN=B);
BY MEMBID;
IF A OR B;
IF VACC=. THEN VACC=0;
RUN;

PROC FREQ DATA=FLU;
TABLES VACC;
WHERE GROUPB=1;
LABEL VACC='VACCINATIONS';
FORMAT VACC VAC.;
TITLE2 'INFLUENZA VACCINATIONS';
TITLE3 'ALL OF GROUP 2';
RUN;

TITLE1 'ADVERSE OUTCOMES';

PROC FREQ DATA=ERV;
TABLES ERV /OUT=ERV2FRQ;
WHERE GROUPB=1;
LABEL ERV='NUMBER OF VISITS';
FORMAT ERV VIS.;
TITLE2 'EMERGENCY ROOM VISITS';
TITLE3 'ALL OF GROUP 2';
RUN;

PROC FREQ DATA=HOSP;
TABLES HOSP /OUT=HOSP2FRQ;
WHERE GROUPB=1;
LABEL HOSP='NUMBER OF VISITS';
FORMAT HOSP VIS.;
TITLE2 'HOSPITALIZATION VISITS';
TITLE3 'ALL OF GROUP 2';
RUN;

DATA DRUG(KEEP=MEMBID Y PROV SITECODE);
SET ASMDR1 END=LASTOBS;
RETAIN FLAG1 FLAG2 0;
FLAG2=0;
IF SUBSTR(ICDCODE,1,4) IN ('9952','9620','9670','9757') THEN FLAG2=1;
IF ICDCODE IN ('E9320','E9370','E9457') THEN FLAG2=1;
IF FLAG2 THEN DO;
   FLAG1=1;
   OUTPUT;
```

```
    END;
IF LASTOBS AND FLAG1=0 THEN DO;
  PROV=0;
  OUTPUT;
  END;
RUN;

DATA DRUG(KEEP=MEMBID Y PROVT);
SET DRUG;
PROVT=' ';
IF PROV=0 THEN PROVT='NONE';
IF 1<=PROV<=27 THEN PROVT='MD';
IF 29<=PROV<=33 THEN PROVT='MD';
IF 36<=PROV<=38 THEN PROVT='MD';
IF PROV=48 THEN PROVT='MD';
IF 50<=PROV<=55 THEN DO;
   IF SITECODE=4 THEN PROVT='HOSPITAL';
   IF SITECODE=8 THEN PROVT='ER';
END;
IF PROV=67 THEN PROVT='ER';
RUN;

DATA DRUG;
MERGE GROUPS(IN=A) DRUG(IN=B);
BY MEMBID;
IF A OR B;
IF PROVT=' ' THEN PROVT='NONE';
RUN;

PROC FREQ DATA=DRUG;
TABLES PROVT /OUT=DRG2FRQ;
WHERE GROUPB=2;
LABEL PROVT='TYPE OF PROVIDER';
TITLE2 'DRUG TOXICITY';
TITLE3 'ALL OF GROUP 2';
RUN;

DATA THEOC2B1(KEEP=QTY MEMBID Y QTYDRUG);
RETAIN QTY;
SET ASMRX1;
BY MEMBID;
WHERE THERCLS=151200;
IF FIRST.MEMBID THEN QTY=0;
QTY=QTYDRUG+QTY;
IF LAST.MEMBID THEN
   IF QTY>200 THEN OUTPUT;
RUN;

DATA THEOC2B2(KEEP=MEMBID CPTCODE CPTMOD CPTDATE);
MERGE THEOC2B1(IN=A) ASMDR1(IN=B);
BY MEMBID;
IF A;
RUN;

PROC SORT DATA=THEOC2B2;
BY MEMBID CPTCODE CPTDATE;
RUN;

DATA THEO2(KEEP=MEMBID Y VISITS);
RETAIN VISITS;
```

```
SET THEOC1B2;
BY MEMBID CPTCODE CPTDATE;
IF FIRST.MEMBID THEN VISITS=0;
IF FIRST.CPTDATE THEN FLAG=0;
IF CPTCODE IN ('84420','82137')THEN FLAG=1;
IF FLAG THEN
   IF LAST.CPTDATE THEN VISITS+1;
IF LAST.MEMBID THEN OUTPUT;
RUN;

DATA THEO2;
MERGE GROUPS(IN=A) THEO2(IN=B);
BY MEMBID;
IF A OR B;
IF VISITS=. THEN VISITS=0;
RUN;

PROC FREQ DATA=THEO2;
TABLES VISITS /OUT=THEO2FRQ;
WHERE GROUPB=1;
FORMAT VISITS VISA.;
TITLE2 'SERUM THEOPHYLLINE LEVEL MONITORING';
TITLE3 'ALL OF GROUP 2';
RUN;

DATA DR2GRP;
SET GROUPS;
BY MEMBID;
WHERE GROUPB=1;
RUN;

TITLE1 'ADVERSE OUTCOMES';

DATA BETA1(KEEP=MEMBID Y DOSAGE)
     THEO1(KEEP=MEMBID Y DOSAGE)
     CROM1(KEEP=MEMBID Y DOSAGE);
SET ASMRX1;
DOSAGE=DOSAGCDE;
IF THERCLS=151100 THEN OUTPUT BETA1;
IF THERCLS=151200 THEN OUTPUT THEO1;
IF GENCODE=2263 THEN OUTPUT CROM1;
RUN;

PROC SORT DATA=BETA1;
BY MEMBID;
RUN;

PROC SORT DATA=THEO1;
BY MEMBID;
RUN;

PROC SORT DATA=CROM1;
BY MEMBID;
RUN;

DATA _NULL_;
SET BETA1 END=LASTOBS;
BY MEMBID;
IF FIRST.MEMBID THEN COUNT+1;
IF LASTOBS THEN CALL SYMPUT('NUM',PUT(COUNT,5.));
```

```
RUN;

PROC FREQ DATA=BETA1;
TABLES DOSAGE;
FORMAT DOSAGE DOS.;
TITLE1 'PHARMACEUTICAL APPROPRIATENESS';
TITLE2 'BETA-ANTAGONISTS';
TITLE3 'NON-INHALANT FORM IS INAPPROPRIATE';
TITLE4 'ALL OF GROUP 1';
TITLE5 "# OF MEMBERS = &NUM";
RUN;

DATA _NULL_;
SET THEO1 END=LASTOBS;
BY MEMBID;
IF FIRST.MEMBID THEN COUNT+1;
IF LASTOBS THEN CALL SYMPUT('NUM',PUT(COUNT,5.));
RUN;

PROC FREQ DATA=THEO1;
TABLES DOSAGE;
FORMAT DOSAGE DOS.;
TITLE2 'THEOPHYLLINE';
TITLE3 'RECTAL OR INHALANT FORMS ARE INAPPROPRIATE';
TITLE4 'ALL OF GROUP 1';
TITLE5 "# OF MEMBERS = &NUM";
RUN;

DATA _NULL_;
SET CROM1 END=LASTOBS;
BY MEMBID;
IF FIRST.MEMBID THEN COUNT+1;
IF LASTOBS THEN CALL SYMPUT('NUM',PUT(COUNT,5.));
RUN;

PROC FREQ DATA=CROM1;
TABLES DOSAGE;
FORMAT DOSAGE DOS.;
TITLE2 'CROMOLYN';
TITLE3 'NON-INHALANT FORMS ARE INAPPROPRIATE';
TITLE4 'ALL OF GROUP 1';
TITLE5 "# OF MEMBERS = &NUM";
RUN;

TITLE5;

DATA THEOC4(KEEP=MEMBID Y CLAIM);
SET ASMRX1;
BY MEMBID;
WHERE THERCLS IN (52100,52200,52300,52400,54600);
IF FIRST.MEMBID THEN DO;
   CLAIM=1;
   OUTPUT;
   END;
RUN;

DATA THEOC42(KEEP=MEMBID Y CLAIM1);
MERGE THEOC4(IN=A) ASMDR1(IN=B);
RETAIN FLAG;
BY MEMBID;
```

```
IF A=B;
IF FIRST.MEMBID THEN FLAG=0;
IF (SUBSTR(ICDCODE,1,3))='345'THEN FLAG=1;
IF LAST.MEMBID AND FLAG THEN DO;
   CLAIM1=0;
   OUTPUT;
   END;
RUN;

DATA THEOC43(KEEP=MEMBID CLAIM Y CLAIM1);
MERGE THEOC4(IN=A) THEOC42(IN=B);
BY MEMBID;
IF A;
IF CLAIM=. THEN CLAIM=0;
IF CLAIM1=. THEN CLAIM1=0;
RUN;

DATA THEOC43(KEEP=MEMBID AGE);
RETAIN FLAG;
SET THEOC43(RENAME=(Y=AGE));
BY MEMBID;
IF FIRST.MEMBID THEN FLAG=1;
IF CLAIM THEN
   IF NOT(CLAIM1) THEN FLAG=0;
IF LAST.MEMBID THEN
   IF FLAG THEN OUTPUT;
RUN;

PROC CONTENTS DATA=THEOC43 OUT=TEMP NOPRINT;
RUN;

DATA BARB43(KEEP=MEMBID);
SET THEOC43 TEMP;
IF NOBS=0 THEN MEMBID='NO MEMBERS FOUND';
RUN;

PROC PRINT DATA=BARB43 NOOBS;
TITLE2 'BARBITURATES';
TITLE3 'ANY USAGE FOR SEDATION DURING ASTHMA ATTACK IS INAPPROPRIATE';
TITLE4 'ALL OF GROUP 1';
RUN;

TITLE1; TITLE2; TITLE3; TITLE4; TITLE5;
FOOTNOTE1; FOOTNOTE2; FOOTNOTE3; FOOTNOTE4;

PROC FORMAT;
   VALUE $SEXFMT
         'M'='MALE'
         'F'='FEMALE';
RUN;

PROC MEANS DATA=GROUPS;
VAR AGE;
CLASS MEMBSEX;
FORMAT MEMBSEX $SEXFMT.;
OUTPUT OUT=MEANS1;
RUN;

PROC FREQ DATA=GROUPS;
TABLES MEMBSEX /OUT=FREQ1;
```

```
FORMAT MEMBSEX $SEXFMT.;
RUN;

DATA T1;
RETAIN MN1 MN2 MND MM1 MM2 MMD MS1 MS2 MSD 0;
SET MEANS1 END=LASTOBS;
IF MEMBSEX='M' AND _STAT_='N' THEN MN1=_FREQ_;
IF MEMBSEX='F' AND _STAT_='N' THEN MN2=_FREQ_;
IF MEMBSEX=' ' AND _STAT_='N' THEN MND=_FREQ_;
IF MEMBSEX='M' AND _STAT_='MEAN' THEN MM1=AGE;
IF MEMBSEX='F' AND _STAT_='MEAN' THEN MM2=AGE;
IF MEMBSEX=' ' AND _STAT_='MEAN' THEN MMD=AGE;
IF MEMBSEX='M' AND _STAT_='STD' THEN MS1=AGE;
IF MEMBSEX='F' AND _STAT_='STD' THEN MS2=AGE;
IF MEMBSEX=' ' AND _STAT_='STD' THEN MSD=AGE;
IF LASTOBS;
RUN;

DATA T2;
RETAIN PER1 PER2 0 PERD 100;
SET FREQ1 END=LASTOBS;
IF MEMBSEX='M' THEN PER1=PERCENT;
IF MEMBSEX='F' THEN PER2=PERCENT;
PERD=100;
IF LASTOBS;
RUN;

DATA TEMP;
MERGE T2 T1;
RUN;

DATA _NULL_;
SET TEMP;
FILE 'ASMPOP.LST';
PUT ///;
PUT @90 'Standard';
PUT @45 'Number' @60 'Percent' @75 'Mean Age' @90 'Deviation';
PUT @45 '-----' @60 '-----' @75 '-----' @90 '-----';
PUT @10 'Children with Asthma';
PUT @10 '-----------';
PUT @15 'Male' @45 mn1 4. @60 per1 4.1 @75 mm1 6.2 @90 ms1 5.2 /;
PUT @15 'Female' @45 mn2 4. @60 per2 4.1 @75 mm2 6.2 @90 ms2 5.2 /;
PUT @15 'Total' @45 mnd 4. @59 perd 5.1 @75 mmd 6.2 @90 msd 5.2 ///;
RUN;

GOPTIONS RESET=(AXIS, LEGEND, PATTERN, SYMBOL, TITLE, FOOTNOTE)
    HTEXT= FTEXT= CTEXT= TARGET= GACCESS= HPOS= VPOS=;
GOPTIONS DEVICE=HPLJ300 FTEXT=NONE CTEXT=BLUE
    HTEXT=1 COLORS=(BLUE) NOBORDER ROTATE=LANDSCAPE;

FILENAME HSP 'ASMPOP.LST';

TITLE1 H=1.5 C=ORANGE F=CENTX J=C LS=2 'DEMOGRAPHICS OF CHILDREN WITH ASTHMA';
TITLE2 H=1 C=ORANGE F=CENTX J=C "&PLAN";
TITLE3 H=1 C=ORANGE F=CENTX J=L LS=2 'ASTHMA_1';

FOOTNOTE1 H=1 C=BLUE F=CENTX J=L
    'ASTHMA_1: presents the demographics for children with asthma.';

PROC GPRINT FILEREF=HSP;
```

```
RUN;
QUIT;

TITLE1; TITLE2; TITLE3; TITLE4; TITLE5;
FOOTNOTE1; FOOTNOTE2; FOOTNOTE3; FOOTNOTE4;

PROC FORMAT;
   VALUE $AGEA
        '0-2'='00-02 YEARS'
        '3-6'='03-06 YEARS'
        '7-12'='07-12 YEARS'
        '13-19'='13-19 YEARS';
RUN;

DATA _NULL_;
SET GROUPS END=LASTOBS;
IF LASTOBS THEN CALL SYMPUT('NUM',LEFT(PUT(_N_,5.)));
RUN;

GOPTIONS RESET=(AXIS, LEGEND, PATTERN, SYMBOL, TITLE, FOOTNOTE)
      HTEXT= FTEXT= CTEXT= TARGET= GACCESS=;
GOPTIONS DEVICE=HPLJ300 FTEXT=CENTX CTEXT=BLACK INTERPOL=JOIN
         HTEXT=1 ROTATE=LANDSCAPE;

PATTERN1 VALUE=PEMPTY;
PATTERN2 VALUE=PSOLID;
PATTERN3 VALUE=P2X45;
PATTERN4 VALUE=P2N25;

TITLE1 FONT=CENTX J=C H=1.5 LS=2 'AGE DISTRIBUTION';
TITLE2 FONT=CENTX J=C H=1 'CHILDREN WITH ASTHMA';
TITLE3 FONT=CENTX J=C H=1 "&PLAN";
TITLE4 FONT=CENTX J=L H=1 LS=2 'ASTHMA_2';

FOOTNOTE1 FONT=CENTX J=C HEIGHT=1 " N= &NUM ";
FOOTNOTE2 FONT=CENTX J=L HEIGHT=1 LS=2
   "ASTHMA_2: presents the age distribution of children with asthma.";

PROC GCHART DATA=GROUPS;
   PIE Y /
      NOHEADING
      DISCRETE
      PERCENT=OUTSIDE
      SLICE=OUTSIDE
      VALUE=OUTSIDE
      TYPE=FREQ
      ;
   FORMAT Y $AGEA.;
RUN;
QUIT;

TITLE1; TITLE2; TITLE3; TITLE4; TITLE5;
FOOTNOTE1; FOOTNOTE2; FOOTNOTE3; FOOTNOTE4;

DATA TEMP1(KEEP=D E H M N);
MERGE DRUG(IN=A) ERV(IN=B) HOSP(IN=C);
BY MEMBID;
IF A OR B OR C;
IF PROVT='NONE' THEN D=0;
ELSE D=1;
```

```
IF HOSP>0 THEN H=1;
ELSE H=0;
IF ERV>0 THEN E=1;
ELSE E=0;
IF (E AND H) OR (E AND D) OR (H AND D) THEN M=1;
ELSE M=0;
IF NOT(E OR H OR D) THEN N=1;
ELSE N=0;
RUN;

DATA TEMP(KEEP=TOTAL PERCENT VALUE);
RETAIN A1 A2 A3 A4 VALUE PERCENT TOTAL 0;
SET TEMP1 END=LASTOBS;
A0+N;
A1+H;
A2+E;
A3+D;
A4+M;
A5=_N_;
IF LASTOBS THEN DO;
   VALUE=1;
   TOTAL=A0;
   PERCENT=(A0/A5)*100;
   OUTPUT;
   VALUE=2;
   TOTAL=A2;
   PERCENT=(A2/A5)*100;
   OUTPUT;
   VALUE=3;
   TOTAL=A1;
   PERCENT=(A1/A5)*100;
   OUTPUT;
   VALUE=4;
   TOTAL=A3;
   PERCENT=(A3/A5)*100;
   OUTPUT;
   VALUE=5;
   TOTAL=A4;
   PERCENT=(A4/A5)*100;
   OUTPUT;
END;
RUN;

DATA NUMBER;
   LENGTH COLOR STYLE $8.;
   LENGTH FUNCTION TEXT $5.;
   LENGTH XSYS YSYS POSITION $1.;
   RETAIN POSITION '5';
   SET TEMP;

XSYS='2';
   YSYS='2';
   MIDPOINT=VALUE;
   FUNCTION='LABEL';
   STYLE='NONE';
   COLOR='BLUE';
   Y=PERCENT+6.8;
   TEXT=COMPRESS(PUT(PERCENT,F4.1))||'%';
   OUTPUT;
   FUNCTION='LABEL';
```

```
    STYLE='NONE';
    COLOR='RED';
    Y=PERCENT+2.5;
    TEXT='//||COMPRESS(PUT(TOTAL,F4.))||//';
    OUTPUT;
RUN;

GOPTIONS RESET=(AXIS, LEGEND, PATTERN, SYMBOL, TITLE, FOOTNOTE)
        HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
        HTEXT=1 COLORS=(BLUE) NOBORDER ROTATE=LANDSCAPE;

TITLE1 H=1.5 C=ORANGE F=CENTX J=C LS=2 'FREQUENCY OF ADVERSE EVENTS';
TITLE2 H=1 C=ORANGE F=CENTX J=C 'CHILDREN WITH ASTHMA';
TITLE3 H=1 C=ORANGE F=CENTX J=C "&PLAN";
TITLE4 H=1 C=ORANGE F=CENTX J=L LS=2 'ASTHMA_3';

FOOTNOTE1 H=1 C=BLUE F=CENTX J=L
  'ASTHMA_3: presents a frequency of asthma-related adverse events.';

PATTERN1 V=L1 C=BLUE;
PATTERN2 V=E  C=BLUE;
PATTERN3 V=E  C=BLUE;
PATTERN4 V=E  C=BLUE;
PATTERN5 V=E  C=BLUE;
PATTERN6 V=E  C=BLUE;

AXIS1 LABEL=NONE
    VALUE=(C=BLUE H=1 F=CENTX
        T=1 'None'
        T=2 'At least 1' J=C 'ER' J=C 'Visit'
        T=3 'At least 1' J=C 'Hospital' J=C 'Admission'
        T=4 'At least 1' J=C 'Drug' J=C 'Toxicity'
        T=5 'Multiple' J=C 'Event' J=C 'Types');
AXIS2 LABEL=(R=90 A=270 'PERCENT OF TOTAL')
    ORDER=0 TO 100 BY 10;

PROC GCHART DATA=TEMP;
    VBAR VALUE /
        DISCRETE
        SUMVAR=PERCENT
        WIDTH=10
        MAXIS=AXIS1
        RAXIS=AXIS2
        ANNOTATE=NUMBER
        PATTERNID=MIDPOINT;
RUN;
QUIT;

TITLE1; TITLE2; TITLE3; TITLE4; TITLE5;
FOOTNOTE1; FOOTNOTE2; FOOTNOTE3; FOOTNOTE4;

PROC FORMAT;
    VALUE VISA
        0='0 VISITS'
        1='1 VISIT'
        2-5='2-5 VISITS'
        6-10='6-10 VISITS'
        11-HIGH='>10 VISITS';
RUN;
```

```
DATA TEMP1;
  INPUT VISITS $12. AGE $;
  CARDS;
0 VISIT      0-2
0 VISIT      3-6
0 VISIT      7-12
0 VISIT      13-19
1 VISIT      0-2
1 VISIT      3-6
1 VISIT      7-12
1 VISIT      13-19
2-5 VISITS   0-2
2-5 VISITS   3-6
2-5 VISITS   7-12
2-5 VISITS   13-19
6-10 VISITS  0-2
6-10 VISITS  3-6
6-10 VISITS  7-12
6-10 VISITS  13-19
> 10 VISITS  0-2
> 10 VISITS  3-6
> 10 VISITS  7-12
> 10 VISITS  13-19
;

PROC SORT DATA=ERV;
BY Y;
RUN;

PROC FREQ DATA=ERV;
BY Y;
TABLES ERV / NOPRINT OUT=TEMP;
FORMAT ERV VISA.;
LABEL Y='AGE';
RUN;

DATA TEMP2;
SET TEMP(RENAME=(Y=AGE));
LENGTH VISITS $12.;
VISITS=PUT(ERV,VISA.);
RUN;

PROC SORT DATA=TEMP2;
BY VISITS AGE;
RUN;

PROC SORT DATA=TEMP1;
BY VISITS AGE;
RUN;

DATA TEMP1;
MERGE TEMP1(IN=A) TEMP2(IN=B);
BY VISITS AGE;
IF A OR B;
RUN;

DATA TEMP1(DROP=X Y);
SET TEMP1;
IF COUNT=. THEN COUNT=0;
IF PERCENT=. THEN PERCENT=0;
```

```
RUN;

PROC FREQ DATA=ERV;
TABLES ERV / NOPRINT OUT=TEMP;
FORMAT ERV VISA.;
RUN;

DATA TEMP2;
SET TEMP;
LENGTH VISITS $12.;
VISITS=PUT(ERV,VISA.);
RUN;

PROC SORT DATA=TEMP2;
BY VISITS;
RUN;

DATA TEMP2;
SET TEMP2;
IF COUNT=. THEN COUNT=0;
IF PERCENT=. THEN PERCENT=0;
RUN;

DATA TEMP;
RETAIN CNT1 CNT2 CNT3 CNT4 CNT5 CNT6 CNT7 CNT8 CNT9 CNT10 CNT31 CNT32 CNT33
       CNT11 CNT12 CNT13 CNT14 CNT15 CNT16 CNT34
       PER1 PER2 PER3 PER4 PER5 PER6 PER7 PER8 PER9 PER10 PER31 PER32 PER33
       PER11 PER12 PER13 PER14 PER15 PER16 PER34 0;
SET TEMP1 END=LASTOBS;
IF VISITS='0 VISITS' AND AGE='0-2' THEN DO;
   CNT31=COUNT;
   PER31=PERCENT;
   END;
IF VISITS='0 VISITS' AND AGE='3-6' THEN DO;
   CNT32=COUNT;
   PER32=PERCENT;
   END;
IF VISITS='0 VISITS' AND AGE='7-12' THEN DO;
   CNT33=COUNT;
   PER33=PERCENT;
   END;
IF VISITS='0 VISITS' AND AGE='13-19' THEN DO;
   CNT34=COUNT;
   PER34=PERCENT;
   END;
IF VISITS='1 VISIT' AND AGE='0-2' THEN DO;
   CNT1=COUNT;
   PER1=PERCENT;
   END;
IF VISITS='1 VISIT' AND AGE='3-6' THEN DO;
   CNT2=COUNT;
   PER2=PERCENT;
   END;
IF VISITS='1 VISIT' AND AGE='7-12' THEN DO;
   CNT3=COUNT;
   PER3=PERCENT;
   END;
IF VISITS='1 VISIT' AND AGE='13-19' THEN DO;
   CNT4=COUNT;
   PER4=PERCENT;
```

```
    END;
IF VISITS='2-5 VISITS' AND AGE='0-2' THEN DO;
    CNT5=COUNT;
    PER5=PERCENT;
    END;
IF VISITS='2-5 VISITS' AND AGE='3-6' THEN DO;
    CNT6=COUNT;
    PER6=PERCENT;
    END;
IF VISITS='2-5 VISITS' AND AGE='7-12' THEN DO;
    CNT7=COUNT;
    PER7=PERCENT;
    END;
IF VISITS='2-5 VISITS' AND AGE='13-19' THEN DO;
    CNT8=COUNT;
    PER8=PERCENT;
    END;
IF VISITS='6-10 VISITS' AND AGE='0-2' THEN DO;
    CNT9=COUNT;
    PER9=PERCENT;
    END;
IF VISITS='6-10 VISITS' AND AGE='3-6' THEN DO;
    CNT10=COUNT;
    PER10=PERCENT;
    END;
IF VISITS='6-10 VISITS' AND AGE='7-12' THEN DO;
    CNT11=COUNT;
    PER11=PERCENT;
    END;
IF VISITS='6-10 VISITS' AND AGE='13-19' THEN DO;
    CNT12=COUNT;
    PER12=PERCENT;
    END;
IF VISITS='> 10 VISITS' AND AGE='0-2' THEN DO;
    CNT13=COUNT;
    PER13=PERCENT;
    END;
IF VISITS='> 10 VISITS' AND AGE='3-6' THEN DO;
    CNT14=COUNT;
    PER14=PERCENT;
    END;
IF VISITS='> 10 VISITS' AND AGE='7-12' THEN DO;
    CNT15=COUNT;
    PER15=PERCENT;
    END;
IF VISITS='> 10 VISITS' AND AGE='13-19' THEN DO;
    CNT16=COUNT;
    PER16=PERCENT;
    END;
IF LASTOBS;
RUN;

DATA TOT1;
RETAIN CNT21 CNT22 CNT23 CNT24 PER21 PER22 PER23 PER24 CNT41 PER41 0;
SET TEMP2 END=LASTOBS;
IF VISITS='0 VISITS' THEN DO;
    CNT41=COUNT;
    PER41=PERCENT;
    END;
IF VISITS='1 VISIT' THEN DO;
```

```
    CNT21=COUNT;
    PER21=PERCENT;
    END;
IF VISITS='2-5 VISITS' THEN DO;
    CNT22=COUNT;
    PER22=PERCENT;
    END;
IF VISITS='6-10 VISITS' THEN DO;
    CNT23=COUNT;
    PER23=PERCENT;
    END;
IF VISITS=', 10 VISITS' THEN DO;
    CNT24=COUNT;
    PER24=PERCENT;
    END;
IF LASTOBS;
RUN;

DATA TEMP(DROP=AGE);
MERGE TOT1 TEMP;
RUN;

DATA _NULL_;
SET TEMP;
RETAIN TOT1 TOT2 TOT3 TOT4 TOT5 100;
FILE 'ASMERA.LST';
AGE='AGE GROUP';
N1=CNT31+CNT1+CNT5+CNT9+CNT13;
N2=CNT32+CNT2+CNT6+CNT10+CNT14;
N3=CNT33+CNT3+CNT7+CNT11+CNT15;
N4=CNT34+CNT4+CNT8+CNT12+CNT16;
N5=CNT41+CNT21+CNT22+CNT23+CNT24;
PUT // AGE $102.-C;
PUT #;
PUT @22 '0-2' @38 '3-6' @54 '7-12' @70 '13-19' @86 'TOTAL';
PUT @22 '—' @38 '—' @54 '—' @70 '—' @86 '—';
PUT;
PUT @5 '0 VISITS'  @21 PER31 5.1 '% (' CNT31 : 3. +(-1) ')'
                   @37 PER32 5.1 '% (' CNT32 : 3. +(-1) ')'
                   @53 PER33 5.1 '% (' CNT33 : 3. +(-1) ')'
                   @69 PER34 5.1 '% (' CNT34 : 3. +(-1) ')'
                   @85 PER41 5.1 '% (' CNT41 : 3. +(-1) ')';
PUT;
PUT @5 '1 VISIT'   @21 PER1 5.1 '% (' CNT1 : 3. +(-1) ')'
                   @37 PER2 5.1 '% (' CNT2 : 3. +(-1) ')'
                   @53 PER3 5.1 '% (' CNT3 : 3. +(-1) ')'
                   @69 PER4 5.1 '% (' CNT4 : 3. +(-1) ')'
                   @85 PER21 5.1 '% (' CNT21 : 3. +(-1) ')';
PUT;
PUT @5 '2-5 VISITS' @21 PER5 5.1 '% (' CNT5 : 3. +(-1) ')'
                   @37 PER6 5.1 '% (' CNT6 : 3. +(-1) ')'
                   @53 PER7 5.1 '% (' CNT7 : 3. +(-1) ')'
                   @69 PER8 5.1 '% (' CNT8 : 3. +(-1) ')'
                   @85 PER22 5.1 '% (' CNT22 : 3. +(-1) ')';
PUT;
PUT @5 '6-10 VISITS' @21 PER9 5.1 '% (' CNT9 : 3. +(-1) ')'
                   @37 PER10 5.1 '% (' CNT10 : 3. +(-1) ')'
                   @53 PER11 5.1 '% (' CNT11 : 3. +(-1) ')'
                   @69 PER12 5.1 '% (' CNT12 : 3. +(-1) ')'
                   @85 PER23 5.1 '% (' CNT23 : 3. +(-1) ')';
```

```
PUT;
PUT @5 '; 10 VISITS' @21 PER13 5.1 '%' (' CNT13 : 3. +(-1) ')'
         @37 PER14 5.1 '%' (' CNT14 : 3. +(-1) ')'
         @53 PER15 5.1 '%' (' CNT15 : 3. +(-1) ')'
         @69 PER16 5.1 '%' (' CNT16 : 3. +(-1) ')'
         @85 PER24 5.1 '%' (' CNT24 : 3. +(-1) ')';
PUT /;
PUT @5 'TOTALS'  @21 TOT1 5.1 '%' (' N1 : 3. +(-1) ')'
         @37 TOT2 5.1 '%' (' N2 : 3. +(-1) ')'
         @53 TOT3 5.1 '%' (' N3 : 3. +(-1) ')'
         @69 TOT4 5.1 '%' (' N4 : 3. +(-1) ')'
         @85 TOT5 5.1 '%' (' N5 : 3. +(-1) ')';
RUN;

GOPTIONS RESET=(AXIS, LEGEND, PATTERN, SYMBOL, TITLE, FOOTNOTE)
         HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
         HTEXT=1 COLORS=(BLUE) NOBORDER ROTATE=LANDSCAPE;

FILENAME HSP 'ASMERA.LST';

TITLE1 H=1.5 C=ORANGE F=CENTX J=C LS=2 'FREQUENCY OF EMERGENCY ROOM VISITS';
TITLE2 H=1 C=ORANGE F=CENTX J=C 'CHILDREN WITH ASTHMA';
TITLE3 H=1 C=ORANGE F=CENTX J=C "&PLAN";
TITLE4 H=1 C=ORANGE F=CENTX J=L LS=2 'ASTHMA_4';

FOOTNOTE1 H=1 C=BLUE F=CENTX J=L
 'ASTHMA_4: presents the frequency of asthma-related emergency room visits for children with asthma.';

PROC GPRINT FILEREF=HSP;
RUN;
QUIT;

TITLE1; TITLE2; TITLE3; TITLE4; TITLE5;
FOOTNOTE1; FOOTNOTE2; FOOTNOTE3; FOOTNOTE4;

DATA TEMP(KEEP=Y VISITS);
SET HOSP;
VISITS=HOSP;
RUN;

PROC FORMAT;
    VALUE VISA
        0='0 VISITS'
        1='1 VISIT '
        2='2 VISITS'
        3-HIGH='3+ VISITS';
RUN;

PROC SORT DATA=TEMP;
BY Y;
RUN;

PROC FREQ DATA=TEMP;
BY Y;
TABLES VISITS / NOPRINT OUT=HOSPAFRQ;
FORMAT VISITS VISA.;
LABEL Y='AGE';
RUN;
```

```
PUT;
PUT @5 '> 10 VISITS' @21 PER13 5.1 '%' (' CNT13 : 3. +(-1) ')'
          @37 PER14 5.1 '%' (' CNT14 : 3. +(-1) ')'
          @53 PER15 5.1 '%' (' CNT15 : 3. +(-1) ')'
          @69 PER16 5.1 '%' (' CNT16 : 3. +(-1) ')'
          @85 PER24 5.1 '%' (' CNT24 : 3. +(-1) ')';
PUT /;
PUT @5 'TOTALS'   @21 TOT1 5.1 '%' (' N1 : 3. +(-1) ')'
          @37 TOT2 5.1 '%' (' N2 : 3. +(-1) ')'
          @53 TOT3 5.1 '%' (' N3 : 3. +(-1) ')'
          @69 TOT4 5.1 '%' (' N4 : 3. +(-1) ')'
          @85 TOT5 5.1 '%' (' N5 : 3. +(-1) ')';
RUN;

GOPTIONS RESET=(AXIS, LEGEND, PATTERN, SYMBOL, TITLE, FOOTNOTE)
      HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
      HTEXT=1 COLORS=(BLUE) NOBORDER ROTATE=LANDSCAPE;

FILENAME HSP 'ASMERA.LST';

TITLE1 H=1.5 C=ORANGE F=CENTX J=C LS=2 'FREQUENCY OF EMERGENCY ROOM VISITS';
TITLE2 H=1 C=ORANGE F=CENTX J=C 'CHILDREN WITH ASTHMA';
TITLE3 H=1 C=ORANGE F=CENTX J=C "&PLAN";
TITLE4 H=1 C=ORANGE F=CENTX J=L LS=2 'ASTHMA_4';

FOOTNOTE1 H=1 C=BLUE F=CENTX J=L
   'ASTHMA_4: presents the frequency of asthma-related emergency room visits for children with asthma.';

PROC GPRINT FILEREF=HSP;
RUN;
QUIT;

TITLE1; TITLE2; TITLE3; TITLE4; TITLE5;
FOOTNOTE1; FOOTNOTE2; FOOTNOTE3; FOOTNOTE4;

DATA TEMP(KEEP=Y VISITS);
SET HOSP;
VISITS=HOSP;
RUN;

PROC FORMAT;
   VALUE VISA
         0='0 VISITS'
         1='1 VISIT'
         2='2 VISITS'
         3-HIGH='3+ VISITS';
RUN;

PROC SORT DATA=TEMP;
BY Y;
RUN;

PROC FREQ DATA=TEMP;
BY Y;
TABLES VISITS / NOPRINT OUT=HOSPAFRQ;
FORMAT VISITS VISA.;
LABEL Y='AGE';
RUN;
```

```
PROC FREQ DATA=TEMP;
TABLES VISITS / NOPRINT OUT=TEMPTOT;
FORMAT VISITS VISA.;
RUN;

DATA TEMP1;
  INPUT VISITS 1. Y $;
  CARDS;
0 0-2
0 3-6
0 7-12
0 13-19
1 0-2
1 3-6
1 7-12
1 13-19
2 0-2
2 3-6
2 7-12
2 13-19
3 0-2
3 3-6
3 7-12
3 13-19
;

PROC SORT DATA=HOSPAFRQ;
BY VISITS Y;
RUN;

PROC SORT DATA=TEMP1;
BY VISITS Y;
RUN;

DATA TEMP1;
MERGE TEMP1(IN=A) HOSPAFRQ(IN=B);
BY VISITS Y;
IF A OR B;
RUN;

DATA TEMP1;
SET TEMP1;
IF COUNT=. THEN COUNT=0;
IF PERCENT=. THEN PERCENT=0;
RUN;

DATA TEMP;
RETAIN CNT1 CNT2 CNT3 CNT4 CNT5 CNT6 CNT7 CNT8 CNT9 CNT10 CNT11 CNT12
    CNT31 CNT32 CNT33 CNT34
    PER1 PER2 PER3 PER4 PER5 PER6 PER7 PER8 PER9 PER10 PER11 PER12
    PER31 PER32 PER33 PER34 0;
SET TEMP1 END=LASTOBS;
IF VISITS=0 AND Y='0-2' THEN DO;
  CNT31=COUNT;
  PER31=PERCENT;
  END;
IF VISITS=0 AND Y='3-6' THEN DO;
  CNT32=COUNT;
  PER32=PERCENT;
  END;
```

```
IF VISITS=0 AND Y='7-12' THEN DO;
   CNT33=COUNT;
   PER33=PERCENT;
   END;
IF VISITS=0 AND Y='13-19' THEN DO;
   CNT34=COUNT;
   PER34=PERCENT;
   END;
IF VISITS=1 AND Y='0-2' THEN DO;
   CNT1=COUNT;
   PER1=PERCENT;
   END;
IF VISITS=1 AND Y='3-6' THEN DO;
   CNT2=COUNT;
   PER2=PERCENT;
   END;
IF VISITS=1 AND Y='7-12' THEN DO;
   CNT3=COUNT;
   PER3=PERCENT;
   END;
IF VISITS=1 AND Y='13-19' THEN DO;
   CNT4=COUNT;
   PER4=PERCENT;
   END;
IF VISITS=2 AND Y='0-2' THEN DO;
   CNT5=COUNT;
   PER5=PERCENT;
   END;
IF VISITS=2 AND Y='3-6' THEN DO;
   CNT6=COUNT;
   PER6=PERCENT;
   END;
IF VISITS=2 AND Y='7-12' THEN DO;
   CNT7=COUNT;
   PER7=PERCENT;
   END;
IF VISITS=2 AND Y='13-19' THEN DO;
   CNT8=COUNT;
   PER8=PERCENT;
   END;
IF VISITS>=3 AND Y='0-2' THEN DO;
   CNT9=COUNT;
   PER9=PERCENT;
   END;
IF VISITS>=3 AND Y='3-6' THEN DO;
   CNT10=COUNT;
   PER10=PERCENT;
   END;
IF VISITS>=3 AND Y='7-12' THEN DO;
   CNT11=COUNT;
   PER11=PERCENT;
   END;
IF VISITS>=3 AND Y='13-19' THEN DO;
   CNT12=COUNT;
   PER12=PERCENT;
   END;
IF LASTOBS;
RUN;

DATA TOT1;
```

```
RETAIN CNT21 CNT22 CNT23 PER21 PER22 PER23 CNT41 PER41 0;
SET TEMPTOT END=LASTOBS;
IF VISITS=0 THEN DO;
   CNT41=COUNT;
   PER41=PERCENT;
   END;
IF VISITS=1 THEN DO;
   CNT21=COUNT;
   PER21=PERCENT;
   END;
IF VISITS=2 THEN DO;
   CNT22=COUNT;
   PER22=PERCENT;
   END;
IF VISITS>=3 THEN DO;
   CNT23=COUNT;
   PER23=PERCENT;
   END;
IF LASTOBS;
RUN;

DATA TEMP;
MERGE TOT1 TEMP;
RUN;

DATA _NULL_;
SET TEMP;
RETAIN TOT1 TOT2 TOT3 TOT4 TOT5 100;
FILE 'ASMHSPA.LST';
AGE='AGE GROUP';
N1=CNT31+CNT1+CNT5+CNT9;
N2=CNT32+CNT2+CNT6+CNT10;
N3=CNT33+CNT3+CNT7+CNT11;
N4=CNT34+CNT4+CNT8+CNT12;
N5=CNT41+CNT21+CNT22+CNT23;
PUT //// AGE $102.-C;
PUT //;
PUT @22 '0-2' @38 '3-6' @54 '7-12' @70 '13-19' @86 'TOTAL';
PUT @22 '—' @38 '—' @54 '—' @70 '—' @86 '—';
PUT;
PUT @5 '0 ADMISSIONS' @21 PER31 5.1 '% (' CNT31 : 3. +(-1) ')'
              @37 PER32 5.1 '% (' CNT32 : 3. +(-1) ')'
              @53 PER33 5.1 '% (' CNT33 : 3. +(-1) ')'
              @69 PER34 5.1 '% (' CNT34 : 3. +(-1) ')'
              @85 PER41 5.1 '% (' CNT41 : 3. +(-1) ')';
PUT;
PUT @5 '1 ADMISSION' @21 PER1 5.1 '% (' CNT1 : 3. +(-1) ')'
              @37 PER2 5.1 '% (' CNT2 : 3. +(-1) ')'
              @53 PER3 5.1 '% (' CNT3 : 3. +(-1) ')'
              @69 PER4 5.1 '% (' CNT4 : 3. +(-1) ')'
              @85 PER21 5.1 '% (' CNT21 : 3. +(-1) ')';
PUT;
PUT @5 '2 ADMISSIONS' @21 PER5 5.1 '% (' CNT5 : 3. +(-1) ')'
              @37 PER6 5.1 '% (' CNT6 : 3. +(-1) ')'
              @53 PER7 5.1 '% (' CNT7 : 3. +(-1) ')'
              @69 PER8 5.1 '% (' CNT8 : 3. +(-1) ')'
              @85 PER22 5.1 '% (' CNT22 : 3. +(-1) ')';
PUT;
PUT @5 '3+ ADMISSIONS' @21 PER9 5.1 '% (' CNT9 : 3. +(-1) ')'
              @37 PER10 5.1 '% (' CNT10 : 3. +(-1) ')'
```

```
        @53 PER11 5.1 '%  (' CNT11 : 3. +(-1) ')'
        @69 PER12 5.1 '%  (' CNT12 : 3. +(-1) ')'
        @85 PER23 5.1 '%  (' CNT23 : 3. +(-1) ')';
PUT;
PUT /;
PUT @5 'TOTALS'   @21 TOT1 5.1 '% (' N1 : 3. +(-1) ')'
        @37 TOT2 5.1 '%  (' N2 : 3. +(-1) ')'
        @53 TOT3 5.1 '%  (' N3 : 3. +(-1) ')'
        @69 TOT4 5.1 '%  (' N4 : 3. +(-1) ')'
        @85 TOT5 5.1 '%  (' N5 : 3. +(-1) ')';
RUN;

GOPTIONS RESET=(AXIS, LEGEND, PATTERN, SYMBOL, TITLE, FOOTNOTE)
        HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
        HTEXT=1 COLORS=(BLUE) NOBORDER ROTATE=LANDSCAPE;

FILENAME HSP 'ASMHSPA.LST';

TITLE1 H=1.5 C=ORANGE F=CENTX J=C LS=2 'FREQUENCY OF HOSPITAL ADMISSIONS';
TITLE2 H=1 C=ORANGE F=CENTX J=C 'CHILDREN WITH ASTHMA';
TITLE3 H=1 C=ORANGE F=CENTX J=C "&PLAN";
TITLE4 H=1 C=ORANGE F=CENTX J=L LS=2 'ASTHMA_5';

FOOTNOTE1 H=1 C=BLUE F=CENTX J=L
'ASTHMA_5: presents the frequency of asthma-related hospital admissions for children with asthma.';

PROC GPRINT FILEREF=HSP;
RUN;
QUIT;

TITLE1; TITLE2; TITLE3; TITLE4; TITLE5;
FOOTNOTE1; FOOTNOTE2; FOOTNOTE3; FOOTNOTE4;

PROC FORMAT;
  VALUE VISA
        0=0
        1-HIGH=1;

VALUE $AGEFMT
    '  '=1
    '0-2'=2
    '3-6'=3
    '7-12'=4
    '13-19'=5;
  INVALUE AGEIFMT
    '  '=1
    '0-2'=2
    '3-6'=3
    '7-12'=4
    '13-19'=5;
RUN;

PROC SORT DATA=OFFVIST;
BY GROUPB Y;
RUN;

PROC FREQ DATA=OFFVIST;
BY GROUPB Y;
TABLES VISITS / NOPRINT OUT=TEMP1;
```

```
FORMAT Y $AGEFMT. VISITS VISA.;
LABEL Y='AGE';
RUN;

PROC FREQ DATA=OFFVIST;
BY GROUPB;
TABLES VISITS / NOPRINT OUT=TEMP;
FORMAT VISITS VISA.;
RUN;

DATA TEMP1(DROP=Y COUNT1);
RETAIN COUNT1 0;
SET TEMP1;
BY GROUPB Y;
IF FIRST.Y THEN COUNT1=0;
COUNT1+COUNT;
IF VISITS;
AGE=INPUT(Y,AGEFMT.);
COUNT=COUNT1;
RUN;

DATA TEMP;
SET TEMP;
BY GROUPB;
IF FIRST.GROUPB THEN COUNT1=0;
COUNT1+COUNT;
IF VISITS;
AGE=1;
COUNT=COUNT1;
RUN;

DATA TEMP;
SET TEMP TEMP1;
RUN;

PROC SORT DATA=TEMP;
BY AGE GROUPB;
RUN;

DATA NUMBER;
    LENGTH COLOR STYLE $8.;
    LENGTH FUNCTION TEXT $5.;
    LENGTH XSYS YSYS POSITION $1.;
    RETAIN POSITION '5';
    SET TEMP;
    SUBGROUP=GROUPB;
    GROUP=AGE;
    XSYS='2';
    YSYS='2';
    MIDPOINT=GROUPB;
    FUNCTION='LABEL';
    STYLE='NONE';
    COLOR='BLUE';
    Y=PERCENT+6.8;
    TEXT=COMPRESS(PUT(PERCENT,F5.1))||'%';
    OUTPUT;
    SUBGROUP=GROUPB;
    GROUP=AGE;
    MIDPOINT=GROUPB;
    FUNCTION='LABEL';
```

```
      STYLE='NONE';
      COLOR='RED';
      Y=PERCENT+2.5;
      TEXT=':'|| COMPRESS(PUT(COUNT,F4.))||':';
      OUTPUT;
RUN;

GOPTIONS RESET=(AXIS, LEGEND, PATTERN, SYMBOL, TITLE, FOOTNOTE)
      HTEXT= FTEXT= CTEXT= TARGET= GACCESS= HPOS= VPOS=;
GOPTIONS DEVICE=HPLJ300 FTEXT=NONE CTEXT=BLUE
      HTEXT=1 COLORS=(BLUE) NOBORDER ROTATE=LANDSCAPE;

TITLE1 H=1.5 C=ORANGE F=CENTX J=C LS=2 'PHYSICIAN OFFICE VISITS';
TITLE2 H=1 C=ORANGE F=CENTX J=C 'CHILDREN WITH ASTHMA';
TITLE3 H=1 C=ORANGE F=CENTX J=C "&PLAN";
TITLE4 H=1 C=ORANGE F=CENTX J=L LS=2 'ASTHMA_6';

FOOTNOTE1 H=1 C=BLUE F=CENTX J=L
   'ASTHMA_6: presents the percent of children who met the guideline of an annual office visit for asthma.';

LEGEND1 MODE=RESERVE
      LABEL=NONE
      VALUE=( COLOR=BLUE HEIGHT=1 FONT=CENTX
         T=1 J=C "No Adverse Events (&NADVER)"
         T=2 J=C "Adverse Events (&ADVER)")
      OFFSET=(0, 0.0625 IN);

PATTERN1 V=L1 C=BLUE;
PATTERN2 V=E C=BLUE;

AXIS1 LABEL=(F=CENTX 'AGE GROUP')
      VALUE=(C=ORANGE H=1 F=CENTX
         T=1 'Overall'
         T=2 '0-2'
         T=3 '3-6'
         T=4 '7-12'
         T=5 '13-19');

AXIS2 LABEL=(H=.85 R=90 A=270 'ANNUAL OFFICE VISIT RATE')
      ORDER=0 TO 110 BY 10;

AXIS3 LABEL=NONE VALUE=NONE;

PROC GCHART DATA=TEMP;
   VBAR GROUPB /
      DISCRETE
      SUMVAR=PERCENT
      WIDTH=5
      GSPACE=2
      MAXIS=AXIS3
      RAXIS=AXIS2
      GAXIS=AXIS1
      SUBGROUP=GROUPB
      GROUP=AGE
      LEGEND=LEGEND1
      ANNOTATE=NUMBER
      PATTERNID=SUBGROUP;
RUN;
QUIT;
```

```
TITLE1; TITLE2; TITLE3; TITLE4; TITLE5;
FOOTNOTE1; FOOTNOTE2; FOOTNOTE3; FOOTNOTE4;

PROC MEANS DATA=OFFVIST NOPRINT;
BY GROUPB;
VAR VISITS;
CLASS Y;
FORMAT Y $AGEFMT.;
OUTPUT OUT=TEMP(RENAME=(Y=AGE)) MEAN=MEANS1 N=COUNT;
RUN;

DATA NUMBER;
   LENGTH COLOR STYLE $8.;
   LENGTH FUNCTION TEXT $5.;
   LENGTH XSYS YSYS POSITION $1.;
   RETAIN POSITION '5';
   SET TEMP;
   SUBGROUP=GROUPB;
   GROUP=AGE;
   XSYS='2';
   YSYS='2';
   MIDPOINT=GROUPB;
   FUNCTION='LABEL';
   STYLE='NONE';
   COLOR='BLUE';
   Y=MEANS1+2;
   TEXT=COMPRESS(PUT(MEANS1,F4.1),'');
   OUTPUT;
   SUBGROUP=GROUPB;
   GROUP=AGE;
   MIDPOINT=GROUPB;
   FUNCTION='LABEL';
   STYLE='NONE';
   COLOR='RED';
   Y=MEANS1+1;
   TEXT='(' || COMPRESS(PUT(COUNT,F5.),'') || ')';
   OUTPUT;
RUN;

GOPTIONS RESET=(AXIS, LEGEND, PATTERN, SYMBOL, TITLE, FOOTNOTE)
      HTEXT= FTEXT= CTEXT= TARGET= GACCESS= HPOS= VPOS=;
GOPTIONS DEVICE=HPLJ300 FTEXT=NONE CTEXT=BLUE
      HTEXT=1 COLORS=(BLUE) NOBORDER ROTATE=LANDSCAPE;

TITLE1 C=CYAN J=C F=CENTX H=1.5 LS=2 'AVERAGE NUMBER OF PHYSICIAN OFFICE VISITS';
TITLE2 C=CYAN J=C F=CENTX H=1 'CHILDREN WITH ASTHMA';
TITLE3 C=CYAN J=C F=CENTX H=1 "&PLAN";
TITLE4 C=CYAN J=L F=CENTX H=1 LS=2 'ASTHMA_J';

FOOTNOTE1 C=GREEN F=CENTX J=LEFT H=1
'ASTHMA_J: presents the average number of asthma-related office visits for children with asthma.';

LEGEND1 MODE=RESERVE
    LABEL=NONE
    VALUE=(COLOR=BLUE HEIGHT=1 FONT=CENTX
        T=1 J=C "NO ADVERSE EVENTS (&NADVER)"
        T=2 J=C "ADVERSE EVENTS (&ADVER)")
        OFFSET=(0, 0.0625 IN);

PATTERN1 V=L1 C=BLUE;
```

```
PATTERN2 V=E C=BLUE;

AXIS1 LABEL=(F=CENTX 'AGE GROUP')
    VALUE=(C=ORANGEH=1 F=CENTX
        T=1 'Overall'
        T=2 '0-2'
        T=3 '3-6'
        T=4 '7-12'
        T=5 '13-19');

AXIS2 LABEL=(H=1 R=90 A=270 'NUMBER OF VISITS')
    ORDER=0 TO 20 BY 10;

AXIS3 LABEL=NONE VALUE=NONE;

PROC GCHART DATA=TEMP;
    VBAR GROUPB /
        DISCRETE
        SUMVAR=MEANS1
        WIDTH=5
        GSPACE=2
        MAXIS=AXIS3
        RAXIS=AXIS2
        GAXIS=AXIS1
        SUBGROUP=GROUPB
        GROUP=AGE
        LEGEND=LEGEND1
        ANNOTATE=NUMBER
        PATTERNID=SUBGROUP;
RUN;
QUIT;

TITLE1; TITLE2; TITLE3; TITLE4; TITLE5;
FOOTNOTE1; FOOTNOTE2; FOOTNOTE3; FOOTNOTE4;

PROC FORMAT;
    VALUE VISA
        0=0
        1-HIGH=1;
RUN;

DATA TEMP;
    INPUT GROUPB 2. VISITS 2. AGE 1.;
    CARDS;
0 1 2
0 1 3
0 1 4
0 1 5
1 1 2
1 1 3
1 1 4
1 1 5
;

RUN;

PROC SORT DATA=PFT;
BY GROUPB Y;
RUN;
```

```
PROC SORT DATA=TEMP;
BY GROUPB AGE;
RUN;

PROC FREQ DATA=PFT;
BY GROUPB Y;
TABLES VISITS / NOPRINT OUT=PFT2FRQ;
FORMAT VISITS VISA. Y $AGEFMT.;
RUN;

PROC FREQ DATA=PFT;
BY GROUPB;
TABLES VISITS / NOPRINT OUT=TEMPTOT;
FORMAT VISITS VISA.;
RUN;

DATA PFT2FRQ(DROP=Y);
RETAIN COUNT1 0;
SET PFT2FRQ;
BY GROUPB Y;
IF FIRST.Y THEN COUNT1=0;
COUNT1+COUNT;
IF VISITS=0 AND NOT(LAST.Y) THEN DELETE;
IF VISITS=0 THEN PERCENT=0;
AGE=INPUT(Y,AGEFMT.);
COUNT=COUNT1;
RUN;

PROC SORT DATA=PFT2FRQ;
BY GROUPB AGE;
RUN;

DATA PFT2FRQ;
MERGE PFT2FRQ(IN=A) TEMP(IN=B);
BY GROUPB AGE;
IF A OR B;
IF COUNT=. THEN COUNT=0;
IF PERCENT=. THEN PERCENT=0;
RUN;

DATA TEMPTOT(DROP=Y COUNT1);
RETAIN COUNT1 0;
SET TEMPTOT END=LASTOBS;
BY GROUPB;
IF FIRST.GROUPB THEN COUNT1=0;
COUNT1+COUNT;
IF VISITS=0 AND LASTOBS THEN PERCENT=0;
ELSE IF
   VISITS=0 THEN DELETE;
AGE=1;
COUNT=COUNT1;
RUN;

DATA TEMP;
SET TEMPTOT PFT2FRQ;
RUN;

PROC SORT DATA=TEMP;
BY AGE GROUPB;
RUN;
```

```
DATA NUMBER;
  LENGTH COLOR STYLE $8.;
  LENGTH FUNCTION TEXT $5.;
  LENGTH XSYS YSYS POSITION $1.;
  RETAIN POSITION '5';
  SET TEMP;
  SUBGROUP=GROUPB;
  GROUP=AGE;
  XSYS='2';
  YSYS='2';
  MIDPOINT=GROUPB;
  FUNCTION='LABEL';
  STYLE='NONE';
  COLOR='BLUE';
  Y=PERCENT+6.8;
  TEXT=COMPRESS(PUT(PERCENT,F5.1))||'%';
  OUTPUT;
  SUBGROUP=GROUPB;
  GROUP=AGE;
  MIDPOINT=GROUPB;
  FUNCTION='LABEL';
  STYLE='NONE';
  COLOR='RED';
  Y=PERCENT+2.5;
  TEXT='('||COMPRESS(PUT(COUNT,F4.))||')';
  OUTPUT;
RUN;

GOPTIONS RESET=(AXIS, LEGEND, PATTERN, SYMBOL, TITLE, FOOTNOTE)
         HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
         HTEXT=1 COLORS=(BLUE) NOBORDER ROTATE=LANDSCAPE;

TITLE1 H=1.5 C=ORANGE F=CENTX J=C LS=2 'PULMONARY FUNCTION TESTING';
TITLE2 H=1 C=ORANGE F=CENTX J=C 'CHILDREN WITH ADVERSE EVENTS';
TITLE3 H=1 C=ORANGE F=CENTX J=C "&PLAN";
TITLE4 H=1 C=ORANGE F=CENTX J=L LS=2 'ASTHMA_B';

FOOTNOTE1 H=1 C=BLUE F=CENTX J=L
'ASTHMA_B: presents the percent of children who had at least one pulmonary function test during the year.';
FOOTNOTE2 H=1 C=BLUE F=CENTX J=L
'The guideline states that children with asthma should be monitored regularly.';

PATTERN1 V=L1 C=BLUE;
PATTERN2 V=E  C=BLUE;

LEGEND1 MODE=RESERVE
        LABEL=NONE
        VALUE=(COLOR=BLUE HEIGHT=1 FONT=CENTX
            T=1 J=C "NO ADVERSE EVENTS (&NADVER)"
            T=2 J=C "ADVERSE EVENTS (&ADVER)")
            OFFSET=(0, 0.0625 IN);

AXIS1 LABEL=(F=CENTX 'AGE GROUP')
      VALUE=(C=ORANGE H=1 F=CENTX
         T=1 'Overall'
         T=2 '0-2'
         T=3 '3-6'
         T=4 '7-12'
         T=5 '13-19');
```

```
AXIS2 LABEL=(H=.75 R=90 A=270 'PULMONARY FUNCTION TESTING RATE')
    ORDER=0 TO 100 BY 10;

AXIS3 LABEL=NONE VALUE=NONE;

PROC GCHART DATA=TEMP;
    VBAR GROUPB /
        DISCRETE
        SUMVAR=PERCENT
        WIDTH=5
        SPACE=2
        MAXIS=AXIS3
        RAXIS=AXIS2
        GAXIS=AXIS1
        SUBGROUP=GROUPB
        GROUP=AGE
        LEGEND=LEGEND1
        ANNOTATE=NUMBER
        PATTERNID=SUBGROUP;
RUN;
QUIT;

TITLE1; TITLE2; TITLE3; TITLE4; TITLE5;
FOOTNOTE1; FOOTNOTE2; FOOTNOTE3; FOOTNOTE4;

PROC SORT DATA=FLU;
BY GROUPB Y;
RUN;

PROC FREQ DATA=FLU;
BY GROUPB;
TABLES VACC / NOPRINT OUT=FLUTOT;
RUN;

PROC FREQ DATA=FLU;
BY GROUPB Y;
TABLES VACC / NOPRINT OUT=FLU2FRQ;
FORMAT Y $AGEFMT.;
RUN;

DATA TEMP(DROP=COUNT1 Y);
RETAIN COUNT1;
SET FLU2FRQ;
BY GROUPB Y;
IF FIRST.Y THEN COUNT1=0;
COUNT1+COUNT;
IF VACC=0 AND NOT(LAST.Y) THEN DELETE;
IF VACC=0 THEN PERCENT=0;
AGE=INPUT(Y,AGEIFMT.);
COUNT=COUNT1;
RUN;

DATA TEMP1(DROP=COUNT1 Y);
RETAIN COUNT1 0;
SET FLUTOT END=LASTOBS;
BY GROUPB;
IF FIRST.GROUPB THEN COUNT1=0;
COUNT1+COUNT;
AGE=1;
IF VACC=0 AND LASTOBS THEN PERCENT=0;
```

```
ELSE IF
  VACC=0 THEN DELETE;
COUNT=COUNT1;
RUN;

PROC SORT DATA=TEMP;
BY GROUPB AGE;
RUN;

DATA TEMP(DROP=Y);
MERGE TEMP(IN=A) TEMP1(IN=B);
BY GROUPB AGE;
IF A OR B;
IF VACC=0 THEN PERCENT=0;
RUN;

DATA NUMBER;
  LENGTH FUNCTION COLOR STYLE $8.;
  LENGTH XSYS YSYS POSITION $1.;
  RETAIN POSITION '5';
  SET TEMP;
  SUBGROUP=GROUPB;
  GROUP=AGE;
  XSYS='2';
  YSYS='2';
  MIDPOINT=GROUPB;
  FUNCTION='LABEL';
  STYLE='NONE';
  COLOR='BLUE';
  Y=PERCENT+6.8;
  TEXT=COMPRESS(PUT(PERCENT,F5.1))||'%';
  OUTPUT;
  SUBGROUP=GROUPB;
  GROUP=AGE;
  MIDPOINT=GROUPB;
  FUNCTION='LABEL';
  STYLE='NONE';
  COLOR='RED';
  Y=PERCENT+2.5;
  TEXT='('||COMPRESS(PUT(COUNT,F4.))||')';
  OUTPUT;
RUN;

GOPTIONS RESET=(AXIS, LEGEND, PATTERN, SYMBOL, TITLE, FOOTNOTE)
    HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
    HTEXT=1 COLORS=(BLUE) NOBORDER ROTATE=LANDSCAPE;

TITLE1 C=CYAN J=C F=CENTX H=1.5 LS=2 'INFLUENZA IMMUNIZATION';
TITLE2 C=CYAN J=C F=CENTX H=1 'CHILDREN WITH ADVERSE EVENTS';
TITLE3 C=CYAN J=C F=CENTX H=1 "&PLAN";
TITLE4 C=CYAN J=L F=CENTX H=1 LS=2 'ASTHMA_9';

FOOTNOTE1 C=GREEN F=CENTX J=LEFT H=1
'ASTHMA_9: presents the annual flu immunization rate for children with adverse events. The guideline states that these';
FOOTNOTE2 C=GREEN F=CENTX J=L H=1
'children should have an annual immunization.';

PATTERN1 V=L1 C=BLUE;
PATTERN2 V=E C=BLUE;
```

```
LEGEND1 MODE=RESERVE
    LABEL=NONE
    VALUE=(COLOR=BLUE HEIGHT=1 FONT=CENTX
        T=1 J=C "NO ADVERSE EVENTS (&NADVER)"
        T=2 J=C "ADVERSE EVENTS (&ADVER)")
    OFFSET=(0, 0.0625 IN);

AXIS1 LABEL=(F=CENTX H=1 'AGE GROUP')
    VALUE=(C=ORANGE H=1 F=CENTX
        T=1 'Overall'
        T=2 '0-2'
        T=3 '3-6'
        T=4 '7-12'
        T=5 '13-19');

AXIS2 LABEL=(H=1 R=90 A=270 'IMMUNIZATION RATE')
    ORDER=0 TO 100 BY 10;

AXIS3 LABEL=NONE VALUE=NONE;

PROC GCHART DATA=TEMP;
    VBAR GROUPB /
        DISCRETE
        SUMVAR=PERCENT
        WIDTH=5
        SPACE=2
        MAXIS=AXIS3
        RAXIS=AXIS2
        GAXIS=AXIS1
        SUBGROUP=GROUPB
        GROUP=AGE
        LEGEND=LEGEND1
        ANNOTATE=NUMBER
        PATTERNID=SUBGROUP;
RUN;
QUIT;

TITLE1; TITLE2; TITLE3; TITLE4; TITLE5;
FOOTNOTE1; FOOTNOTE2; FOOTNOTE3; FOOTNOTE4;

PROC FORMAT;
    VALUE VISA
        0='0 VISITS'
        1='1 VISIT'
        2-HIGH='2+ VISITS';
RUN;

DATA TEMP1;
    INPUT VISITS $12. AGE $;
    CARDS;
0 VISITS    0-2
0 VISITS    3-6
0 VISITS    7-12
0 VISITS    13-19
1 VISIT     0-2
1 VISIT     3-6
1 VISIT     7-12
1 VISIT     13-19
2+ VISITS   0-2
2+ VISITS   3-6
```

```
2+ VISITS    7-12
2+ VISITS    13-19
;

PROC SORT DATA=THEO2;
BY Y;
RUN;

PROC FREQ DATA=THEO2;
BY Y;
TABLES VISITS / NOPRINT OUT=TEMP;
FORMAT VISITS VISA.;
LABEL Y='AGE';
RUN;

DATA TEMP2;
SET TEMP(RENAME=(VISITS=X Y=AGE));
VISITS=PUT(X,VISA.);
RUN;

PROC SORT DATA=TEMP2;
BY VISITS AGE;
RUN;

PROC SORT DATA=TEMP1;
BY VISITS AGE;
RUN;

DATA TEMP1;
MERGE TEMP1(IN=A) TEMP2(IN=B);
BY VISITS AGE;
IF A OR B;
RUN;

DATA TEMP1(DROP=X Y);
SET TEMP1;
IF COUNT=. THEN COUNT=0;
IF PERCENT=. THEN PERCENT=0;
RUN;

PROC FREQ DATA=THEO2;
TABLES VISITS / NOPRINT OUT=TEMP;
FORMAT VISITS VISA.;
RUN;

DATA TEMP2;
SET TEMP(RENAME=(VISITS=X));
VISITS=PUT(X,VISA.);
RUN;

PROC SORT DATA=TEMP2;
BY VISITS;
RUN;

DATA TEMP2;
SET TEMP2;
IF COUNT=. THEN COUNT=0;
IF PERCENT=. THEN PERCENT=0;
RUN;
```

```
DATA TEMP;
RETAIN CNT1 CNT2 CNT3 CNT4 CNT5 CNT6 CNT7 CNT8 CNT9 CNT10
       CNT11 CNT12
       PER1 PER2 PER3 PER4 PER5 PER6 PER7 PER8 PER9 PER10
       PER11 PER12 0;
SET TEMP1 END=LASTOBS;
IF VISITS='0 VISITS' AND AGE='0-2' THEN DO;
  CNT1=COUNT;
  PER1=PERCENT;
  END;
IF VISITS='0 VISITS' AND AGE='3-6' THEN DO;
  CNT2=COUNT;
  PER2=PERCENT;
  END;
IF VISITS='0 VISITS' AND AGE='7-12' THEN DO;
  CNT3=COUNT;
  PER3=PERCENT;
  END;
IF VISITS='0 VISITS' AND AGE='13-19' THEN DO;
  CNT4=COUNT;
  PER4=PERCENT;
  END;
IF VISITS='1 VISIT' AND AGE='0-2' THEN DO;
  CNT5=COUNT;
  PER5=PERCENT;
  END;
IF VISITS='1 VISIT' AND AGE='3-6' THEN DO;
  CNT6=COUNT;
  PER6=PERCENT;
  END;
IF VISITS='1 VISIT' AND AGE='7-12' THEN DO;
  CNT7=COUNT;
  PER7=PERCENT;
  END;
IF VISITS='1 VISIT' AND AGE='13-19' THEN DO;
  CNT8=COUNT;
  PER8=PERCENT;
  END;
IF VISITS='2+ VISITS' AND AGE='0-2' THEN DO;
  CNT9=COUNT;
  PER9=PERCENT;
  END;
IF VISITS='2+ VISITS' AND AGE='3-6' THEN DO;
  CNT10=COUNT;
  PER10=PERCENT;
  END;
IF VISITS='2+ VISITS' AND AGE='7-12' THEN DO;
  CNT11=COUNT;
  PER11=PERCENT;
  END;
IF VISITS='2+ VISITS' AND AGE='13-19' THEN DO;
  CNT12=COUNT;
  PER12=PERCENT;
  END;
IF LASTOBS;
RUN;

DATA TOT1;
RETAIN CNT21 CNT22 CNT23 PER21 PER22 PER23 0;
SET TEMP2 END=LASTOBS;
```

```
IF VISITS='0 VISITS' THEN DO;
   CNT21=COUNT;
   PER21=PERCENT;
END;
IF VISITS='1 VISIT' THEN DO;
   CNT22=COUNT;
   PER22=PERCENT;
END;
IF VISITS='2+ VISITS' THEN DO;
   CNT23=COUNT;
   PER23=PERCENT;
END;
IF LASTOBS;
RUN;

DATA TEMP(DROP=AGE);
MERGE TOT1 TEMP;
RUN;

DATA _NULL_;
SET TEMP;
RETAIN TOT1 TOT2 TOT3 TOT4 TOT5 100;
FILE 'ASMST.LST';
AGE='AGE GROUP';
N1=CNT1+CNT5+CNT9;
N2=CNT2+CNT6+CNT10;
N3=CNT3+CNT7+CNT11;
N4=CNT4+CNT8+CNT12;
N5=CNT21+CNT22+CNT23;
PUT // AGE $102.-C;
PUT //;
PUT @22 '0-2' @38 '3-6' @54 '7-12' @70 '13-19' @86 'TOTAL';
PUT @22 '—' @38 '—' @54 '—' @70 '—' @86 '—';
PUT;
PUT @5 '0 TESTS'  @21 PER1 5.1 '%' (' CNT1 : 3. +(-1) ')'
                  @37 PER2 5.1 '%' (' CNT2 : 3. +(-1) ')'
                  @53 PER3 5.1 '%' (' CNT3 : 3. +(-1) ')'
                  @69 PER4 5.1 '%' (' CNT4 : 3. +(-1) ')'
                  @85 PER21 5.1 '%' (' CNT21 : 3. +(-1) ')';
PUT;
PUT @5 '1 TEST'   @21 PER5 5.1 '%' (' CNT5 : 3. +(-1) ')'
                  @37 PER6 5.1 '%' (' CNT6 : 3. +(-1) ')'
                  @53 PER7 5.1 '%' (' CNT7 : 3. +(-1) ')'
                  @69 PER8 5.1 '%' (' CNT8 : 3. +(-1) ')'
                  @85 PER22 5.1 '%' (' CNT22 : 3. +(-1) ')';
PUT;
PUT @5 '2+ TESTS' @21 PER9 5.1 '%' (' CNT9 : 3. +(-1) ')'
                  @37 PER10 5.1 '%' (' CNT10 : 3. +(-1) ')'
                  @53 PER11 5.1 '%' (' CNT11 : 3. +(-1) ')'
                  @69 PER12 5.1 '%' (' CNT12 : 3. +(-1) ')'
                  @85 PER23 5.1 '%' (' CNT23 : 3. +(-1) ')';
PUT /;
PUT @5 'TOTALS'   @21 TOT1 5.1 '%' (' N1 : 3. +(-1) ')'
                  @37 TOT2 5.1 '%' (' N2 : 3. +(-1) ')'
                  @53 TOT3 5.1 '%' (' N3 : 3. +(-1) ')'
                  @69 TOT4 5.1 '%' (' N4 : 3. +(-1) ')'
                  @85 TOT5 5.1 '%' (' N5 : 3. +(-1) ')';
RUN;

GOPTIONS RESET=(AXIS, LEGEND, PATTERN, SYMBOL, TITLE, FOOTNOTE)
```

```
HTEXT= FTEXT= CTEXT= TARGET= GACCESS= HPOS=; VPOS=;
GOPTIONS DEVICE=HPLJ300 FTEXT=NONE CTEXT=BLUE INTERPOL=JOIN
        HTEXT=1 COLORS=(BLUE) NOBORDER ROTATE=LANDSCAPE;

FILENAME HSP 'ASMST.LST';

TITLE1 H=1.5 C=ORANGE F=CENTX J=C LS=2 'SERUM THEOPHYLLINE LEVEL MONITORING';
TITLE2 H=1 C=ORANGE F=CENTX J=C 'CHILDREN PRESCRIBED PHARMACEUTICALS';
TITLE3 H=1 C=ORANGE F=CENTX J=C "&PLAN";
TITLE4 H=1 C=ORANGE F=CENTX J=L LS=2 'ASTHMA_10';

FOOTNOTE1 H=1 C=BLUE F=CENTX J=L
  'ASTHMA_10: presents the frequency of visits with serum theophylline level monitoring for children who are prescribed';
FOOTNOTE2 H=1 C=BLUE F=CENTX J=L
  'theophylline regularly. The guideline for theophylline monitoring is at least twice per patient per year.';

PROC GPRINT FILEREF=HSP;
RUN;
QUIT;

TITLE1; TITLE2; TITLE3; TITLE4; TITLE5;
FOOTNOTE1; FOOTNOTE2; FOOTNOTE3; FOOTNOTE4;

DATA TEMP(KEEP=MEMBID AGE DOSAGE);
SET BETA1;
AGE=Y;
RUN;

PROC FORMAT;
  VALUE DOS
      13,25='INHALANTFORM'
        27='RECTAL FORM'
        14='INJECTABLE FORM'
2-3,8-12,20-23,
      29-30,41='ORAL FORM';
RUN;

PROC SORT DATA=TEMP;
BY AGE;
RUN;

PROC FREQ DATA=TEMP;
BY AGE;
TABLES DOSAGE / NOPRINT OUT=BETA1FRQ;
FORMAT DOSAGE DOS.;
RUN;

DATA TEMP1;
   INPUT DOSAGE $15. AGE $;
   CARDS;
INHALANTFORM    0-2
INHALANTFORM    3-6
INHALANTFORM    7-12
INHALANTFORM    13-19
INJECTABLE FORM 0-2
INJECTABLE FORM 3-6
INJECTABLE FORM 7-12
INJECTABLE FORM 13-19
ORAL FORM       0-2
ORAL FORM       3-6
```

```
ORAL FORM    7-12
ORAL FORM    13-19
;

DATA BETA1FRQ;
SET BETA1FRQ(RENAME=(DOSAGE=X));
DOSAGE=PUT(X,DOS.);
RUN;

PROC SORT DATA=BETA1FRQ;
BY DOSAGE AGE;
RUN;

PROC SORT DATA=TEMP1;
BY DOSAGE AGE;
RUN;

DATA TEMP1;
MERGE TEMP1(IN=A) BETA1FRQ(IN=B);
BY DOSAGE AGE;
IF A OR B;
RUN;
DATA TEMP1;
SET TEMP1;
IF COUNT=. THEN COUNT=0;
IF PERCENT=. THEN PERCENT=0;
RUN;

PROC SORT DATA=TEMP;
BY AGE MEMBID;
RUN;

DATA TOT1(KEEP=CNT21 CNT22 CNT23 CNT24 PRE21 PRE22 PRE23 PRE24);
RETAIN CNT21 CNT22 CNT23 CNT24 PRE21 PRE22 PRE23 PRE24 0;
SET TEMP END=LASTOBS;
BY AGE MEMBID;
IF FIRST.AGE AND AGE='0-2' THEN DO;
    CNT21=0;
    PRE21=0;
    END;
IF AGE='0-2' THEN PRE21=PRE21+1;
IF AGE='0-2' AND FIRST.MEMBID THEN CNT21=CNT21+1;
IF FIRST.AGE AND AGE='3-6' THEN DO;
    CNT22=0;
    PRE22=0;
    END;
IF AGE='3-6' THEN PRE22=PRE22+1;
IF AGE='3-6' AND FIRST.MEMBID THEN CNT22=CNT22+1;
IF FIRST.AGE AND AGE='7-12' THEN DO;
    CNT23=0;
    PRE23=0;
    END;
IF AGE='7-12' THEN PRE23=PRE23+1;
IF AGE='7-12' AND FIRST.MEMBID THEN CNT23=CNT23+1;
IF FIRST.AGE AND AGE='13-19' THEN DO;
    CNT24=0;
    PRE24=0;
    END;
IF AGE='13-19' THEN PRE24=PRE24+1;
IF AGE='13-19' AND FIRST.MEMBID THEN CNT24=CNT24+1;
```

```
IF LASTOBS;
RUN;

DATA TEMP;
RETAIN PER1 PER2 PER3 PER4 PER5 PER6 PER7 PER8 PER9 PER10
    PER11 PER12 0;
SET TEMP1 END=LASTOBS;
IF DOSAGE='INHALANTFORM' AND AGE='0-2' THEN PER1=PERCENT;
IF DOSAGE='INHALANTFORM' AND AGE='3-6' THEN PER2=PERCENT;
IF DOSAGE='INHALANTFORM' AND AGE='7-12' THEN PER3=PERCENT;
IF DOSAGE='INHALANTFORM' AND AGE='13-19' THEN PER4=PERCENT;
IF DOSAGE='ORALFORM' AND AGE='0-2' THEN PER5=PERCENT;
IF DOSAGE='ORALFORM' AND AGE='3-6' THEN PER6=PERCENT;
IF DOSAGE='ORALFORM' AND AGE='7-12' THEN PER7=PERCENT;
IF DOSAGE='ORALFORM' AND AGE='13-19' THEN PER8=PERCENT;
IF DOSAGE='INJECTABLEFORM' AND AGE='0-2' THEN PER9=PERCENT;
IF DOSAGE='INJECTABLEFORM' AND AGE='3-6' THEN PER10=PERCENT;
IF DOSAGE='INJECTABLEFORM' AND AGE='7-12' THEN PER11=PERCENT;
IF DOSAGE='INJECTABLEFORM' AND AGE='13-19' THEN PER12=PERCENT;
IF LASTOBS;
RUN;

DATA TEMP(DROP=AGE);
MERGE TOT1 TEMP;
RUN;

DATA _NULL_;
SET TEMP;
FILE 'ASMBETA.LST';
AGE='AGE GROUP';
PUT // AGE $102.-C;
PUT //;
PUT @38 '0-2' @54 '3-6' @70 '7-12' @86 '13-19';
PUT @38 '---' @54 '---' @70 '---' @86 '---';
PUT /;
PUT @5 'Inhalant Form'   @38 PER1 5.1 '%'
                         @54 PER2 5.1 '%'
                         @70 PER3 5.1 '%'
                         @86 PER4 5.1 '%'/;
PUT;
PUT @5 'Oral Form'       @38 PER5 5.1 '%'
                         @54 PER6 5.1 '%'
                         @70 PER7 5.1 '%'
                         @86 PER8 5.1 '%'/;
PUT;
PUT @5 'Injectable Form' @38 PER9 5.1 '%'
                         @54 PER10 5.1 '%'
                         @70 PER11 5.1 '%'
                         @86 PER12 5.1 '%'/;
PUT ///;
PUT @5 'Prescriptions Filled'  @35 PRE21 COMMA7.
                               @51 PRE22 COMMA7.
                               @67 PRE23 COMMA7.
                               @83 PRE24 COMMA7. /;
PUT @5 'Number of Children'    @35 CNT21 COMMA7.
                               @51 CNT22 COMMA7.
                               @67 CNT23 COMMA7.
                               @83 CNT24 COMMA7.;
RUN;
```

```
GOPTIONS RESET=(AXIS, LEGEND, PATTERN, SYMBOL, TITLE, FOOTNOTE)
        HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
        HTEXT=1 COLORS=(BLUE) NOBORDER ROTATE=LANDSCAPE;

FILENAME HSP 'ASMBETA.LST';

TITLE1 H=1.5 C=ORANGE F=CENTX J=C LS=2 'USE OF BETA-AGONISTS';
TITLE2 H=1 C=ORANGE F=CENTX J=C 'CHILDREN PRESCRIBED PHARMACEUTICALS';
TITLE3 H=1 C=ORANGE F=CENTX J=C "&PLAN";
TITLE4 H=1 C=ORANGE F=CENTX J=L LS=2 'ASTHMA_11';

FOOTNOTE1 H=1 C=BLUE F=CENTX J=L
'ASTHMA_11: presents the percent of prescriptions filled for different forms of beta-agonists. The guideline for';
FOOTNOTE2 H=1 C=BLUE F=CENTX J=L
'prescribing beta-agonists states that the inhalant form is preferred.';

PROC GPRINT FILEREF=HSP;
RUN;
QUIT;

TITLE1; TITLE2; TITLE3; TITLE4; TITLE5;
FOOTNOTE1; FOOTNOTE2; FOOTNOTE3; FOOTNOTE4;

DATA TEMP(KEEP=MEMBID AGE DOSAGE);
SET CROM1;
AGE=Y;
RUN;

PROC SORT DATA=TEMP;
BY AGE;
RUN;

PROC FREQ DATA=TEMP;
BY AGE;
TABLES DOSAGE/ NOPRINT OUT=CROM1FRQ;
FORMAT DOSAGE DOS.;
RUN;

DATA TEMP1;
    INPUT DOSAGE $15. AGE $;
    CARDS;
INHALANTFORM    0-2
INHALANTFORM    3-6
INHALANTFORM    7-12
INHALANTFORM    13-19
ORAL FORM       0-2
ORAL FORM       3-6
ORAL FORM       7-12
ORAL FORM       13-19
;

DATA CROM1FRQ;
SET CROM1FRQ(RENAME=(DOSAGE=X));
DOSAGE=PUT(X,DOS.);
RUN;

PROC SORT DATA=CROM1FRQ;
BY DOSAGE AGE;
RUN;
```

```
PROC SORT DATA=TEMP1;
BY DOSAGE AGE;
RUN;

DATA TEMP1;
MERGE TEMP1(IN=A) CROM1FRQ(IN=B);
BY DOSAGE AGE;
IF A OR B;
RUN;

DATA TEMP1;
SET TEMP1;
IF COUNT=. THEN COUNT=0;
IF PERCENT=. THEN PERCENT=0;
RUN;

PROC SORT DATA=TEMP;
BY AGE MEMBID;
RUN;

DATA TOT1(KEEP=CNT21 CNT22 CNT23 CNT24 PRE21 PRE22 PRE23 PRE24);
RETAIN CNT21 CNT22 CNT23 CNT24 PRE21 PRE22 PRE23 PRE24 0;
SET TEMP END=LASTOBS;
BY AGE MEMBID;
IF FIRST.AGE AND AGE='0-2' THEN DO;
   CNT21=0;
   PRE21=0;
   END;
IF AGE='0-2' THEN PRE21=PRE21+1;
IF AGE='0-2' AND FIRST.MEMBID THEN CNT21=CNT21+1;
IF FIRST.AGE AND AGE='3-6' THEN DO;
   CNT22=0;
   PRE22=0;
   END;
IF AGE='3-6' THEN PRE22=PRE22+1;
IF AGE='3-6' AND FIRST.MEMBID THEN CNT22=CNT22+1;
IF FIRST.AGE AND AGE='7-12' THEN DO;
   CNT23=0;
   PRE23=0;
   END;
IF AGE='7-12' THEN PRE23=PRE23+1;
IF AGE='7-12' AND FIRST.MEMBID THEN CNT23=CNT23+1;
IF FIRST.AGE AND AGE='13-19' THEN DO;
   CNT24=0;
   PRE24=0;
   END;
IF AGE='13-19' THEN PRE24=PRE24+1;
IF AGE='13-19' AND FIRST.MEMBID THEN CNT24=CNT24+1;
IF LASTOBS;
RUN;

DATA TEMP;
RETAIN PER1 PER2 PER3 PER4 PER5 PER6 PER7 PER8 0;
SET TEMP1 END=LASTOBS;
IF DOSAGE='INHALANTFORM' AND AGE='0-2' THEN PER1=PERCENT;
IF DOSAGE='INHALANTFORM' AND AGE='3-6' THEN PER2=PERCENT;
IF DOSAGE='INHALANTFORM' AND AGE='7-12' THEN PER3=PERCENT;
IF DOSAGE='INHALANTFORM' AND AGE='13-19' THEN PER4=PERCENT;
IF DOSAGE='ORALFORM' AND AGE='0-2' THEN PER5=PERCENT;
IF DOSAGE='ORALFORM' AND AGE='3-6' THEN PER6=PERCENT;
```

```
IF DOSAGE='ORALFORM' AND AGE='7-12' THEN PER7=PERCENT;
IF DOSAGE='ORALFORM' AND AGE='13-19' THEN PER8=PERCENT;
IF LASTOBS;
RUN;

DATA TEMP(DROP=AGE);
MERGE TOT1 TEMP;
RUN;

DATA _NULL_;
SET TEMP;
FILE 'ASMCROM.LST';
AGE='AGE GROUP';
PUT // AGE $102.-C;
PUT //;
PUT //;
PUT @38 '0-2' @54 '3-6' @70 '7-12' @86 '13-19';
PUT @38 '—' @54 '—' @70 '—' @86 '—';
PUT /;
PUT @5 'Inhalant Form'   @38 PER1 5.1 '%'
                         @54 PER2 5.1 '%'
                         @70 PER3 5.1 '%'
                         @86 PER4 5.1 '%'/;
PUT;
PUT @5 'Oral Form'       @38 PER5 5.1 '%'
                         @54 PER6 5.1 '%'
                         @70 PER7 5.1 '%'
                         @86 PER8 5.1 '%'/;
PUT ///;
PUT @5 'Prescriptions Filled' @35 PRE21 COMMA7.
                         @51 PRE22 COMMA7.
                         @67 PRE23 COMMA7.
                         @83 PRE24 COMMA7. /;
PUT @5 'Number of Children' @35 CNT21 COMMA7.
                         @51 CNT22 COMMA7.
                         @67 CNT23 COMMA7.
                         @83 CNT24 COMMA7.;
RUN;

GOPTIONS RESET=(AXIS, LEGEND, PATTERN, SYMBOL, TITLE, FOOTNOTE)
      HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
         HTEXT=1 COLORS=(BLUE) NOBORDER ROTATE=LANDSCAPE;

FILENAME HSP 'ASMCROM.LST';

TITLE1 H=1.5 C=ORANGE F=CENTX J=C LS=2 'USE OF CROMOLYN';
TITLE2 H=1 C=ORANGE F=CENTX J=C 'CHILDREN PRESCRIBED PHARMACEUTICALS';
TITLE3 H=1 C=ORANGE F=CENTX J=C '&PLAN';
TITLE4 H=1 C=ORANGE F=CENTX J=L LS=2 'ASTHMA_12';

FOOTNOTE1 H=1 C=BLUE F=CENTX J=L
'ASTHMA_12: presents the percent of prescriptions filled for different forms of cromolyn. The guideline for';
FOOTNOTE2 H=1 C=BLUE F=CENTX J=L
'prescribing cromolyn states that the inhalant form is preferred.';

PROC GPRINT FILEREF=HSP;
RUN;
QUIT;

TITLE1; TITLE2; TITLE3; TITLE4; TITLE5;
```

```
FOOTNOTE1; FOOTNOTE2; FOOTNOTE3; FOOTNOTE4;

DATA TEMP(KEEP=MEMBID AGE DOSAGE);
SET THEO1;
AGE=Y;
RUN;

PROC SORT DATA=TEMP;
BY AGE;
RUN;

PROC FREQ DATA=TEMP;
BY AGE;
TABLES DOSAGE / NOPRINT OUT=THEO1FRQ;
FORMAT DOSAGE DOS.;
RUN;

DATA TEMP1;
   INPUT DOSAGE $15. AGE $;
   CARDS;
INHALANT FORM    0-2
INHALANT FORM    3-6
INHALANT FORM    7-12
INHALANT FORM    13-19
ORAL FORM        0-2
ORAL FORM        3-6
ORAL FORM        7-12
ORAL FORM        13-19
RECTAL FORM      0-2
RECTAL FORM      3-6
RECTAL FORM      7-12
RECTAL FORM      13-19
;

DATA THEO1FRQ;
SET THEO1FRQ(RENAME=(DOSAGE=X));
DOSAGE=PUT(X,DOS.);
RUN;

PROC SORT DATA=THEO1FRQ;
BY DOSAGE AGE;
RUN;

PROC SORT DATA=TEMP1;
BY DOSAGE AGE;
RUN;

DATA TEMP1;
MERGE TEMP1(IN=A) THEO1FRQ(IN=B);
BY DOSAGE AGE;
IF A OR B;
RUN;

DATA TEMP1;
SET TEMP1;
IF COUNT=. THEN COUNT=0;
IF PERCENT=. THEN PERCENT=0;
RUN;

PROC SORT DATA=TEMP;
```

```
BY AGE MEMBID;
RUN;

DATA TOT1(KEEP=CNT21 CNT22 CNT23 CNT24 PRE21 PRE22 PRE23 PRE24);
RETAIN CNT21 CNT22 CNT23 CNT24 PRE21 PRE22 PRE23 PRE24 0;
SET TEMP END=LASTOBS;
BY AGE MEMBID;
IF FIRST.AGE AND AGE='0-2' THEN DO;
    CNT21=0;
    PRE21=0;
    END;
IF AGE='0-2' THEN PRE21=PRE21+1;
IF AGE='0-2' AND FIRST.MEMBID THEN CNT21=CNT21+1;
IF FIRST.AGE AND AGE='3-6' THEN DO;
    CNT22=0;
    PRE22=0;
    END;
IF AGE='3-6' THEN PRE22=PRE22+1;
IF AGE='3-6' AND FIRST.MEMBID THEN CNT22=CNT22+1;
IF FIRST.AGE AND AGE='7-12' THEN DO;
    CNT23=0;
    PRE23=0;
    END;
IF AGE='7-12' THEN PRE23=PRE23+1;
IF AGE='7-12' AND FIRST.MEMBID THEN CNT23=CNT23+1;
IF FIRST.AGE AND AGE='13-19' THEN DO;
    CNT24=0;
    PRE24=0;
    END;
IF AGE='13-19' THEN PRE24=PRE24+1;
IF AGE='13-19' AND FIRST.MEMBID THEN CNT24=CNT24+1;
IF LASTOBS;
RUN;

DATA TEMP;
RETAIN PER1 PER2 PER3 PER4 PER5 PER6 PER7 PER8
       PER13 PER14 PER15 PER16 0;
SET TEMP1 END=LASTOBS;
IF DOSAGE='INHALANTFORM' AND AGE='0-2' THEN PER1=PERCENT;
IF DOSAGE='INHALANTFORM' AND AGE='3-6' THEN PER2=PERCENT;
IF DOSAGE='INHALANTFORM' AND AGE='7-12' THEN PER3=PERCENT;
IF DOSAGE='INHALANTFORM' AND AGE='13-19' THEN PER4=PERCENT;
IF DOSAGE='ORAL FORM' AND AGE='0-2' THEN PER5=PERCENT;
IF DOSAGE='ORAL FORM' AND AGE='3-6' THEN PER6=PERCENT;
IF DOSAGE='ORAL FORM' AND AGE='7-12' THEN PER7=PERCENT;
IF DOSAGE='ORAL FORM' AND AGE='13-19' THEN PER8=PERCENT;
IF DOSAGE='RECTAL FORM' AND AGE='0-2' THEN PER13=PERCENT;
IF DOSAGE='RECTAL FORM' AND AGE='3-6' THEN PER14=PERCENT;
IF DOSAGE='RECTAL FORM' AND AGE='7-12' THEN PER15=PERCENT;
IF DOSAGE='RECTAL FORM' AND AGE='13-19' THEN PER16=PERCENT;
IF LASTOBS;
RUN;

DATA TEMP(DROP=AGE);
MERGE TOT1 TEMP;
RUN;

DATA _NULL_;
SET TEMP;
FILE 'ASMTHEO.LST';
```

```
AGE='AGE GROUP';
PUT // AGE $102.-C;
PUT //;
PUT @38 '0-2' @54 '3-6' @70 '7-12' @86 '13-19';
PUT @38 '—' @54 '—' @70 '—' @86 '—';
PUT /;
PUT @5 'Oral Form'    @38 PER5 5.1 '%'
                      @54 PER6 5.1 '%'
                      @70 PER7 5.1 '%'
                      @86 PER8 5.1 '%'/;
PUT;
PUT @5 'Inhalant Form' @38 PER1 5.1 '%'
                       @54 PER2 5.1 '%'
                       @70 PER3 5.1 '%'
                       @86 PER4 5.1 '%'/;
PUT;
PUT @5 'Rectal'       @38 PER13 5.1 '%'
                      @54 PER14 5.1 '%'
                      @70 PER15 5.1 '%'
                      @86 PER16 5.1 '%'/;
PUT ///;
PUT @5 'Prescriptions Filled' @35 PRE21 COMMA7.
                              @51 PRE22 COMMA7.
                              @67 PRE23 COMMA7.
                              @83 PRE24 COMMA7. /;
PUT @5 'Number of Children' @35 CNT21 COMMA7.
                            @51 CNT22 COMMA7.
                            @67 CNT23 COMMA7.
                            @83 CNT24 COMMA7.;
RUN;

GOPTIONS RESET=(AXIS, LEGEND, PATTERN, SYMBOL, TITLE, FOOTNOTE)
      HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
           HTEXT=1 COLORS=(BLUE) NOBORDER ROTATE=LANDSCAPE;

FILENAME HSP 'ASMTHEO.LST';

TITLE1 H=1.5 C=ORANGE F=CENTX J=C LS=2 'USE OF THEOPHYLLINE';
TITLE2 H=1 C=ORANGE F=CENTX J=C 'CHILDREN PRESCRIBED PHARMACEUTICALS';
TITLE3 H=1 C=ORANGE F=CENTX J=C "&PLAN";
TITLE4 H=1 C=ORANGE F=CENTX J=L 'ASTHMA_13';

FOOTNOTE1 H=1 C=BLUE F=CENTX J=L
 'ASTHMA_13: presents the percent of prescriptions filled for different forms of theophylline. The guideline for';
FOOTNOTE2 H=1 C=BLUE F=CENTX J=L
 'prescribing theophylline states that the inhalant and rectal forms are inappropriate.';

PROC GPRINT FILEREF=HSP;
RUN;
QUIT;

TITLE1; TITLE2; TITLE3; TITLE4; TITLE5;
FOOTNOTE1; FOOTNOTE2; FOOTNOTE3; FOOTNOTE4;

PROC SORT DATA=THEOC43;
BY MEMBID AGE;
RUN;

DATA TEMP;
```

```
SET THEOC43;
BY MEMBID AGE;
IF FIRST.MEMBID;
RUN;

PROC FREQ DATA=TEMP;
TABLES AGE / NOPRINT OUT=BARB1FRQ;
RUN;

DATA TEMP1;
   INPUT AGE $;
   CARDS;
0-2
3-6
7-12
13-19
;

PROC SORT DATA=BARB1FRQ;
BY AGE;
RUN;

PROC SORT DATA=TEMP1;
BY AGE;
RUN;

DATA TEMP1;
MERGE TEMP1(IN=A) BARB1FRQ(IN=B);
BY AGE;
IF A OR B;
RUN;

DATA TEMP1;
SET TEMP1;
IF COUNT=. THEN COUNT=0;
RUN;

DATA TEMP;
RETAIN CNT1 CNT2 CNT3 CNT4 0;
SET TEMP1 END=LASTOBS;
IF AGE='0-2' THEN CNT1=COUNT;
IF AGE='3-6' THEN CNT2=COUNT;
IF AGE='7-12' THEN CNT3=COUNT;
IF AGE='13-19' THEN CNT4=COUNT;
IF LASTOBS;
RUN;

DATA TEMP(DROP=AGE);
SET TEMP;
RUN;

DATA _NULL_;
SET TEMP;
FILE 'ASMBARB.LST';
AGE='AGE GROUP';
PUT //// AGE $102.-C;
PUT //;
PUT @38 '0-2' @54 '3-6' @70 '7-12' @86 '13-19';
PUT @38 '—' @54 '—' @70 '—' @86 '—';
PUT /;
```

```
PUT @5 'Barbituate Use'    @39 CNT1 : COMMA7.
                @55 CNT2 : COMMA7.
                @72 CNT3 : COMMA7.
                @88 CNT4 : COMMA7.;
PUT @5 '(Number of Children)';
RUN;

GOPTIONS RESET=(AXIS, LEGEND, PATTERN, SYMBOL, TITLE, FOOTNOTE)
        HTEXT= FTEXT= CTEXT= TARGET= GACCESS= HPOS= VPOS=;
GOPTIONS DEVICE=HPLJ300 FTEXT=NONE CTEXT=BLUE INTERPOL=JOIN
        HTEXT=1 COLORS=(BLUE) NOBORDER ROTATE=LANDSCAPE;

FILENAME HSP 'ASMBARB.LST';

TITLE1 H=1.5 C=ORANGE F=CENTX J=C LS=2 'FREQUENCY OF BARBITUATE USE FOR SEDATION';
TITLE2 H=1 C=ORANGE F=CENTX J=C 'CHILDREN PRESCRIBED PHARMACEUTICALS';
TITLE3 H=1 C=ORANGE F=CENTX J=C "&PLAN";
TITLE4 H=1 C=ORANGE F=CENTX J=L LS=2 'ASTHMA_14';

FOOTNOTE1 H=1 C=BLUE F=CENTX J=L
 'ASTHMA_14: presents the number of children with asthma who may have been prescribed a barbituate for use during an';
FOOTNOTE2 H=1 C=BLUE F=CENTX J=L
 'asthma attack. The use of barbituates for sedation during an asthma attack is considered inappropriate.';

PROC GPRINT FILEREF=HSP;
RUN;
QUIT;
```

QSM
Quality Screen -- Pediatric Asthma

1. CLAIMS ANALYSIS

A. Population to be Studied: members between ages 1-19 with claims showing evidence of treatment for asthma or asthma-related problems.

B. Quality Indicators:

1. Rationale for Selection: Emergency room visits, hospital admission, and occurrences of drug toxicity are considered important indicators of potential areas for quality improvement in the medical management of asthmatics. Experts agree that most of these events are preventable.[1,2] Key components of the medical care received by children with these adverse events are reported and compared with those of children who did not experience an adverse event.[3,4]

Appropriate pharmaceutical use is another important area for quality review in the treatment of asthma.[5,6] Key components of appropriateness of the pharmaceutical therapy received by these children are reported.

2. Claims Indicators: The following indicators are reported by the pediatric asthma claims data screen:

Children with Asthma:

Medical Visits:
      1 visit per year

Pulmonary Function Testing:
      Regular monitoring using spirometry or peak flow Flu Vaccination:
      Annual vaccination Children Prescribed Pharmaceutical Treatment for Asthma:

Use of Beta-agonists, Theophylline, Cromolyn:
      Appropriateness of route of administration Theophylline Level Monitoring (when applicable):
      Semi-annual monitoring

APPENDIX C

Use of Barbituates:
No barbituate use for asthma treatment unless using for seizure disorder

II. DETAILED ANALYSIS

A.    Population to be Studied: children with adverse events related to asthma.

B.    Rationale for Selection: A medical record analysis of the process of care for these groups can be conducted to determine if the number of adverse events can be reduced by improving the care of children with asthma.

---

1. Brock RH, Lohr KN, Berman DM, Applegate KH, Goldberg GA. Measurement of physiologic health for children: allergic conditions. Rand Corporation, 1983.
2. Canny GJ, Reisman J, Healy R. Acute asthma: observations regarding the management of a pediatric emergency room. Pediatrics 1989; 83: 507-12.
3. American Thoracic Society. Standards for the diagnosis and care of patients with chronic obstructive pulmonary disease (COPD) and asthma. American Lung Association, 1987.
4. Siegel SC, Rachelefsky GS. Asthma in infants and children: part I. The Journal of Allergy and Clinical Immunology 1985; 76: 1.14.
5. Barnes, PJ. A new approach to the treatment of asthma. New England Journal of Medicine 1989; 321:1517-27.
6. Rachelefsky GS, Siegel SC. Asthma in infants and children – treatment of childhood asthma: part II. The Journal of Allergy and Clinical Immunology 1985; 76: 409-25.

ASTHMA_1

DEMOGRAPHICS OF CHILDREN WITH ASTHMA

| Children with Asthma | Number | Percent | Mean Age | Standard Deviation |
|---|---|---|---|---|
| Male | 61 | 65.6 | 7.82 | 4.38 |
| Female | 32 | 34.4 | 8.34 | 5.37 |
| Total | 93 | 100.0 | 8.00 | 4.72 |

ASTHMA_1: presents the demographics for children with asthma.

ASTHMA_2
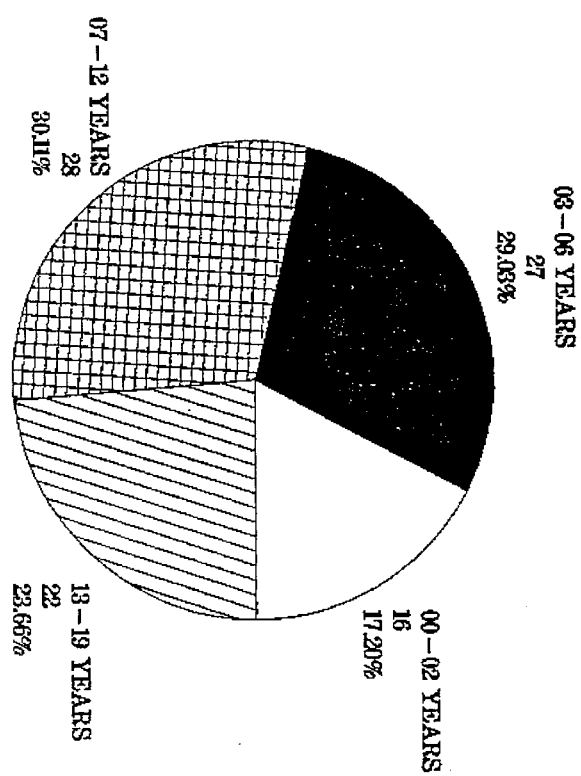
AGE DISTRIBUTION
CHILDREN WITH ASTHMA
03–06 YEARS
27
29.03%
07–12 YEARS
28
30.11%
13–19 YEARS
22
23.66%
00–02 YEARS
16
17.20%
N = 93
ASTHMA_2: presents the age distribution of children with asthma.

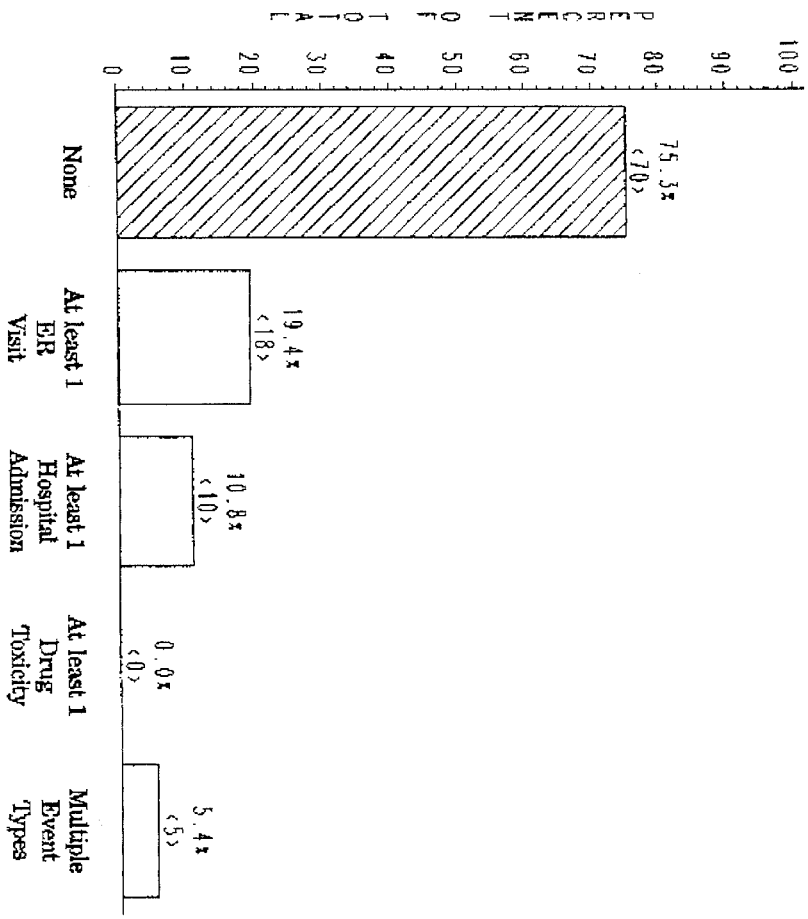
ASTHMA_3: presents a frequency of asthma-related adverse events.

FREQUENCY OF EMERGENCY ROOM VISITS
CHILDREN WITH ASTHMA

ASTHMA_4

| | \<br\>AGE GROUP | | | | |
|---|---|---|---|---|---|
| | 0-2 | 3-6 | 7-12 | 13-19 | TOTAL |
| 0 VISITS | 87.5% (14) | 74.1% (20) | 78.6% (22) | 86.4% (19) | 80.6% (75) |
| 1 VISIT | 0.0% (0) | 7.4% (2) | 7.1% (2) | 0.0% (0) | 4.3% (4) |
| 2-5 VISITS | 12.5% (2) | 18.5% (5) | 10.7% (3) | 13.6% (3) | 14.0% (13) |
| 6-10 VISITS | 0.0% (0) | 0.0% (0) | 3.6% (1) | 0.0% (0) | 1.1% (1) |
| > 10 VISITS | 0.0% (0) | 0.0% (0) | 0.0% (0) | 0.0% (0) | 0.0% (0) |
| TOTALS | 100.0% (16) | 100.0% (27) | 100.0% (28) | 100.0% (22) | 100.0% (93) |

ASTHMA_4: presents the frequency of asthma-related emergency room visits for children with asthma.

ASTHMA_5

FREQUENCY OF HOSPITAL ADMISSIONS
CHILDREN WITH ASTHMA

| | AGE GROUP | | | | |
|---|---|---|---|---|---|
| | 0-2 | 3-6 | 7-12 | 13-19 | TOTAL |
| 0 ADMISSIONS | 100.0% (16) | 85.2% (23) | 85.7% (24) | 90.9% (20) | 89.2% (83) |
| 1 ADMISSION | 0.0% (0) | 11.1% (3) | 14.3% (4) | 9.1% (2) | 9.7% (9) |
| 2 ADMISSIONS | 0.0% (0) | 3.7% (1) | 0.0% (0) | 0.0% (0) | 1.1% (1) |
| 3+ ADMISSIONS | 0.0% (0) | 0.0% (0) | 0.0% (0) | 0.0% (0) | 0.0% (0) |
| TOTALS | 100.0% (16) | 100.0% (27) | 100.0% (28) | 100.0% (22) | 100.0% (93) |

ASTHMA_5: presents the frequency of asthma-related hospital admissions for children with asthma.

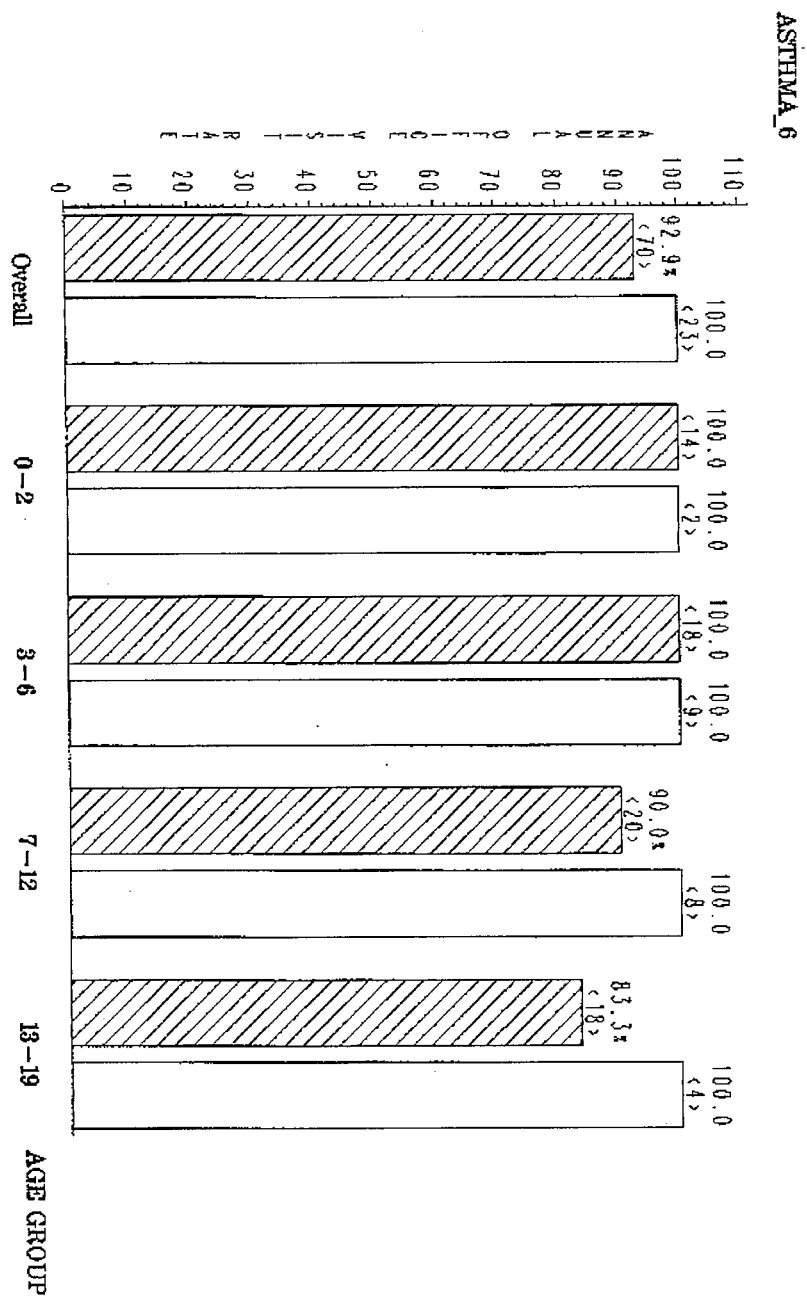
ASTHMA_6: presents the percent of children who met the guideline of an annual office visit for asthma.

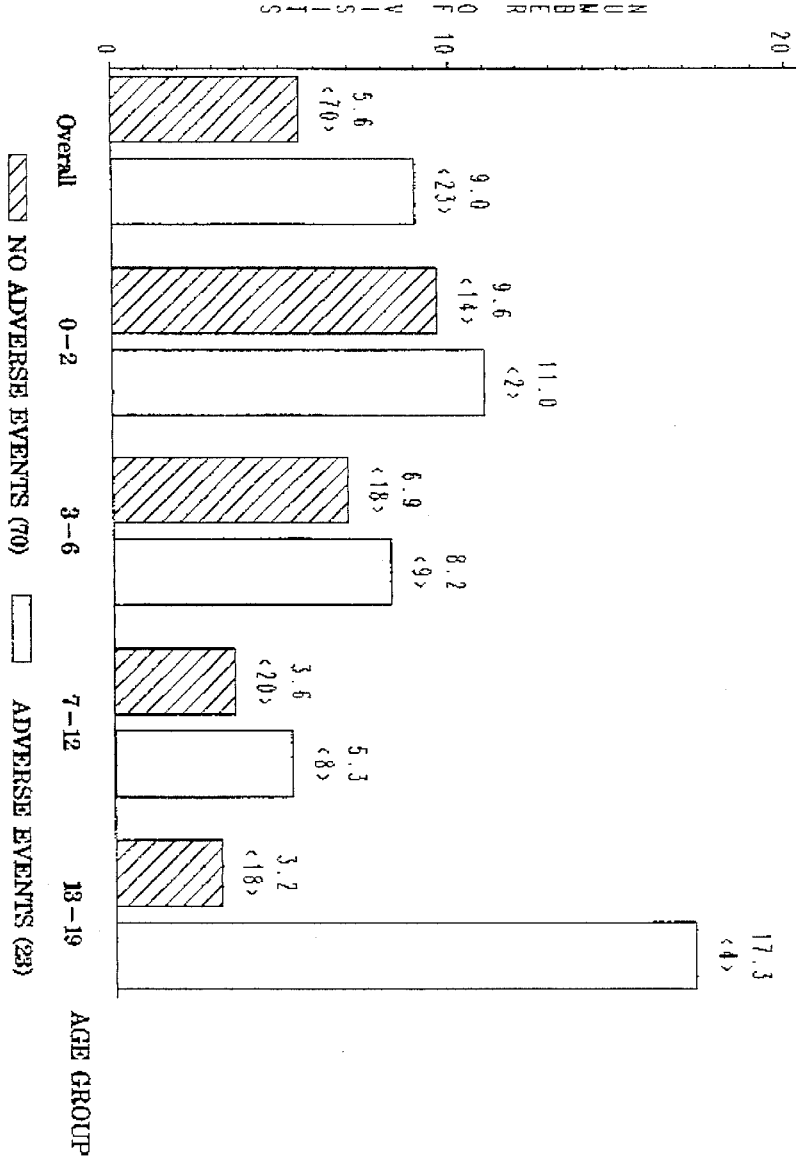
ASTHMA_7: presents the average number of asthma-related office visits for children with asthma.

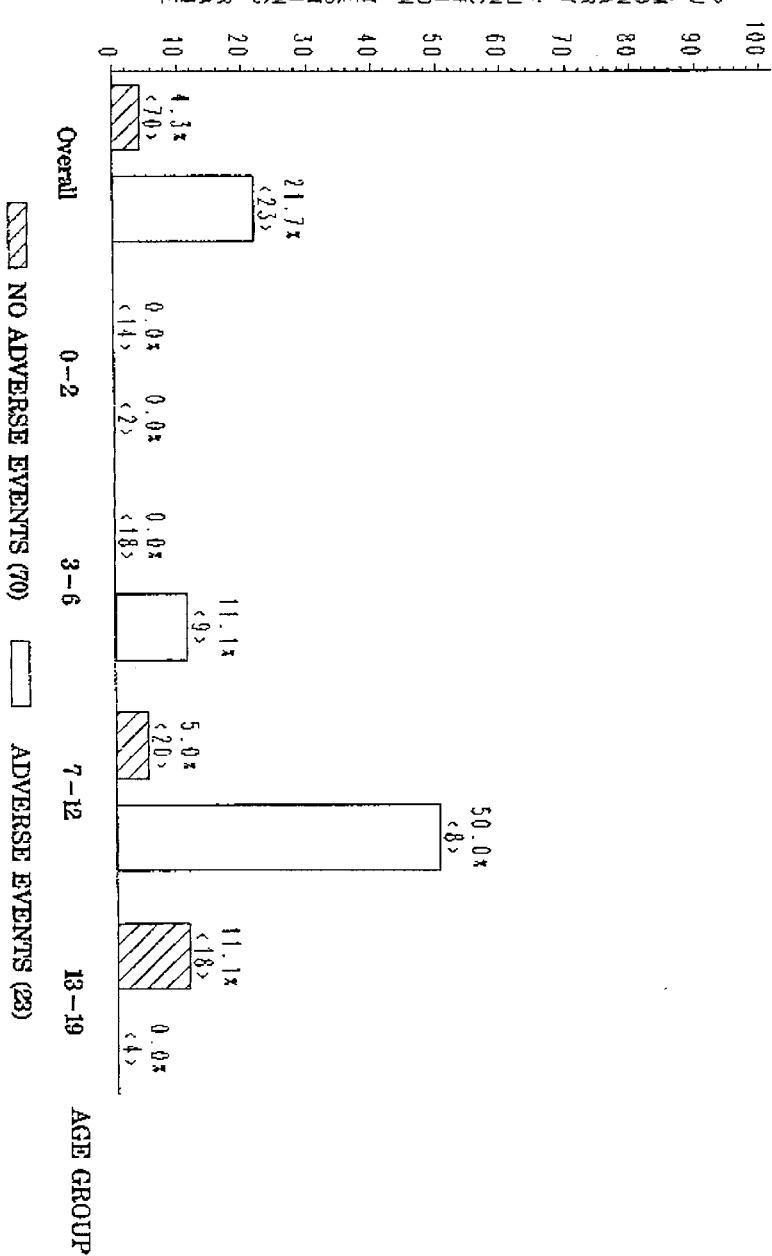
ASTHMA_8: presents the percent of children who had at least one pulmonary function test during the year. The guideline states that children with asthma should be monitored regularly.

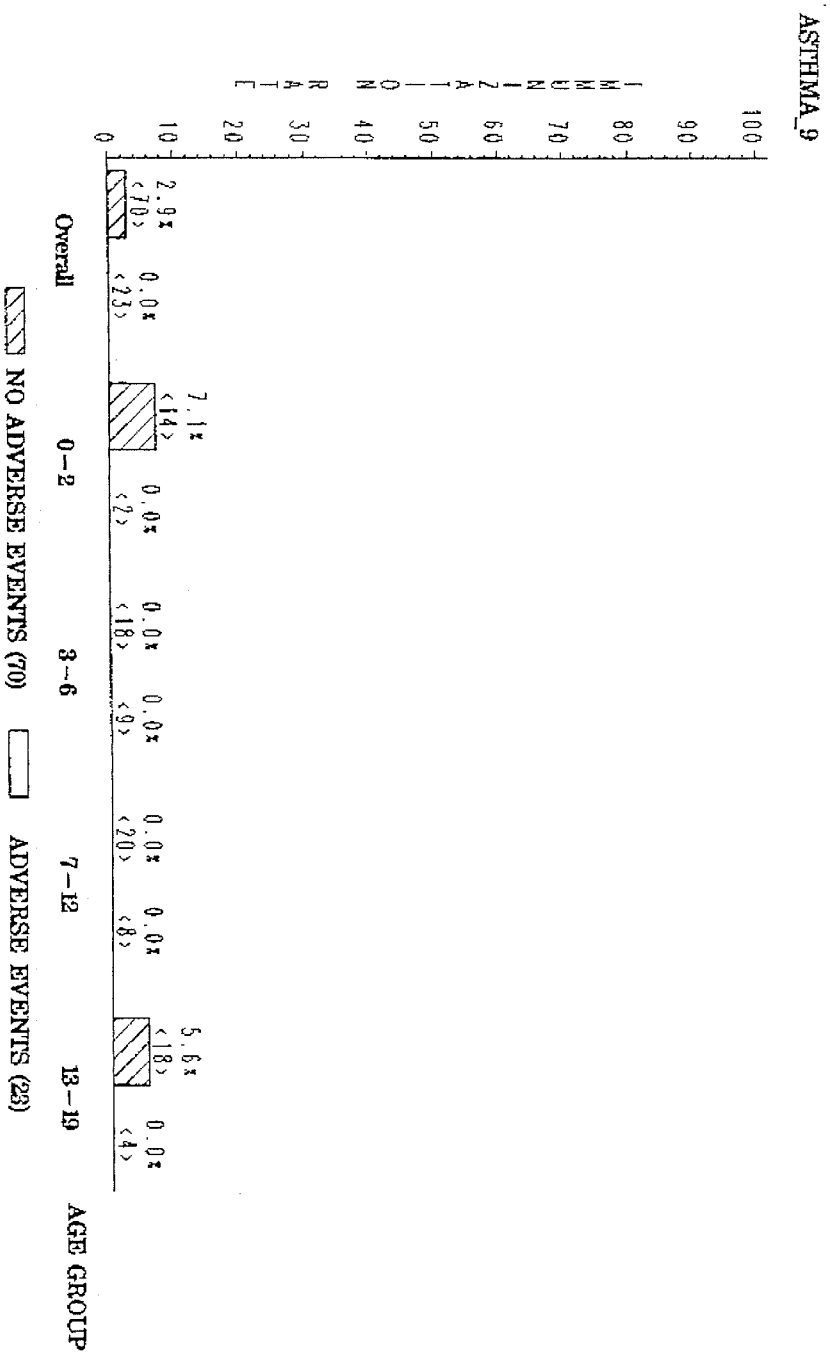
ASTHMA_9: presents the annual flu immunization rate for children with adverse events. The guideline states that these children should have an annual immunization.

SERUM THEOPHYLLINE LEVEL MONITORING
CHILDREN PRESCRIBED PHARMACEUTICALS

ASTHMA_10

| | AGE GROUP | | | | |
|---|---|---|---|---|---|
| | 0-2 | 3-6 | 7-12 | 13-19 | TOTAL |
| 0 TESTS | 100.0% (16) | 92.6% (25) | 89.3% (25) | 95.5% (21) | 93.5% (87) |
| 1 TEST | 0.0% (0) | 7.4% (2) | 7.1% (2) | 4.5% (1) | 5.4% (5) |
| 2+ TESTS | 0.0% (0) | 0.0% (0) | 3.6% (1) | 0.0% (0) | 1.1% (1) |
| TOTALS | 100.0% (16) | 100.0% (27) | 100.0% (28) | 100.0% (22) | 100.0% (93) |

ASTHMA_10: presents the frequency of visits with serum theophylline level monitoring for children who are prescribed theophylline regularly. The guideline for theophylline monitoring is at least twice per patient per year.

USE OF BETA-AGONISTS
CHILDREN PRESCRIBED PHARMACEUTICALS

ASTHMA_11

| | AGE GROUP | | | |
|---|---|---|---|---|
| | 0-2 | 3-6 | 7-12 | 13-19 |
| Inhalant Form | 0.0% | 9.8% | 27.3% | 61.8% |
| Oral Form | 100.0% | 90.2% | 72.7% | 38.2% |
| Injectable Form | 0.0% | 0.0% | 0.0% | 0.0% |
| Prescriptions Filled | 53 | 112 | 143 | 102 |
| Number of Children | 15 | 24 | 20 | 19 |

ASTHMA_11: presents the percent of prescriptions filled for different forms of beta-agonists. The guideline for prescribing beta-agonists states that the inhalant form is preferred.

USE OF CROMOLYN
CHILDREN PRESCRIBED PHARMACEUTICALS

ASTHMA_12

| | AGE GROUP | | | |
|---|---|---|---|---|
| | 0-2 | 3-6 | 7-12 | 13-19 |
| Inhalant Form | 25.0% | 100.0% | 52.6% | 90.9% |
| Oral Form | 75.0% | 0.0% | 47.4% | 9.1% |
| Prescriptions filled | 4 | 12 | 19 | 11 |
| Number of Children | 1 | 2 | 5 | 8 |

ASTHMA_12: presents the percent of prescriptions filled for different forms of cromolyn. The guideline for prescribing cromolyn states that the inhalant form is preferred.

USE OF THEOPHYLLINE
CHILDREN PRESCRIBED PHARMACEUTICALS

ASTHMA_13

| | AGE GROUP | | | | |
|---|---|---|---|---|---|
| | 0-2 | 3-6 | 7-12 | 13-19 |
| Oral Form | 100.0% | 100.0% | 100.0% | 100.0% |
| Inhalant Form | 0.0% | 0.0% | 0.0% | 0.0% |
| Rectal | 0.0% | 0.0% | 0.0% | 0.0% |
| Prescriptions Filled | 8 | 64 | 33 | 67 |
| Number of Children | 4 | 10 | 8 | 11 |

ASTHMA_13: presents the percent of prescriptions filled for different forms of theophylline. The guideline for prescribing theophylline states that the inhalant and rectal forms are inappropriate.

FREQUENCY OF BARBITUATE USE FOR SEDATION
CHILDREN PRESCRIBED PHARMACEUTICALS

ASTHMA_14

| | AGE GROUP | | | |
|---|---|---|---|---|
| | 0-2 | 3-6 | 7-12 | 13-19 |
| Barbituate Use (Number of Children) | 0 | 0 | 0 | 0 |

ASTHMA_14: presents the number of children with asthma who may have been prescribed a barbituate for use during an asthma attack. The use of barbituates for sedation during an asthma attack is considered inappropriate.

QSM Quality Screen:         Pediatric Asthma

Results:

Date:

Data Source:              Claims Data

The rates for emergency room visits and hospital admissions were as follows:

> 15.1% of children had at least two emergency room visits for an asthma-related condition. [Asthma_3]

> 10.8% of children had at least one hospital admission for an asthma-related condition. [Asthma_4]

In the care of children with asthma, children with asthma-related adverse events were compared to children without adverse events:

> All of the children with an adverse event and over 90.0% of children without an adverse event met the guideline of an annual office visit. [Asthma_6]

> Children with an adverse event consistently had a higher average number of office visits across age than those without an adverse event. [Asthma_7]

> Overall, a larger percentage of children had a pulmonary function test in the group with an adverse event (21.7%) compared to children who did not have an adverse event (4.3%). However, neither group performed very well against the guideline. [Asthma_8]

> A very small percentage of children in either group received an influenza immunization during the year. [Asthma_9]

In the analysis of drug treatment for asthma, the findings were:

> 64.7% of children prescribed theophylline regularly did not have their serum theophylline level monitored. [Asthma_10]

> Theophylline was administered orally in all cases. [Asthma_13]

> Prescriptions filled for beta-agonists were in the oral form 92.9% of the time for children under 6; 72.5% of the time for children age 7-12; and 38.6% of the time for children 13-19. [Asthma_11]

> Cromolyn in inhalant form was generally more prevalent when prescribed for children except in children under 3 years of age (75.0%). [Asthma_12]

> No children were prescribed barbiturates for their condition. [Asthma_15]

Quality Management Actions Matrix

| | Report QSM to MDs | Practice Guide-lines | Specific Medical Record Flowsheets | Reimburse MD | Provider Discipline | Patient Education & Reminder | Case Mgt. Programs | Patient's Access to Care | Change Benefit Design |
|---|---|---|---|---|---|---|---|---|---|
| DIABETES | ■ | ■ | ■ | | | ■ | ■ | | |
| *PEDIATRIC ASTHMA* | ■ | ■ | ■ | | | ■ | ■ | | |
| PRENATAL CARE | ■ | ■ | ■ | ■ | | ■ | ■ | | |
| C-SECTION | ■ | ■ | | ■ | | | | | |
| PED. IMMUNIZATION | ■ | ■ | ■ | | | ■ | ■ | | |
| CERVICAL CANCER | ■ | ■ | | | | ■ | | | |
| BREAST CANCER | ■ | | | | | ■ | ■ | | |
| READMISSION | | | | | | | | | ■ |

This matrix illustrates some of the appropriate actions to consider in effecting quality improvement. The shaded areas indicate those actions which are suggested to be the most feasible.

QSM

Quality Management Actions

ASTHMA

These quality management actions are presented as a menu of possible ways to improve quality. They can be used as illustrated or revised to meet specific community needs.

Report to Physicians

- Communicate results of QSM analysis to physicians.
- Discuss possible actions by specific clinic to impact the care of asthmatics.

Establish Guidelines

- Establish and implement guideline for annual flu vaccine and theophylline monitoring.

Medical Record Flow Sheet

- Design and implement a medical record form to record process issues, stress issues, acute episodic care and current medication regime. Physicians may use this as their visit note if signed or as a reminder as they write a narrative note.

Patient Education

- Drug information packet including information on side effects, possible drug interactions and correct administration techniques.
- Article in newsletter on benefits of flu vaccine for asthmatic children.
- Member news article on asthma; educating parents on process of decreasing medication, questions to ask, signs of impending crisis, how to communicate with physician and when to seek urgent services.

Asthma - Page 2

Case Management

- Assign asthmatics with 2 hospitalizations or ER visits in a year to case management program for education, intervention and support services coordination.
- Education of parents on the benefits of continuity of care with a primary care physician as opposed to frequent ER/urgent care episodes.

Access to Care

- Design and implement an intervention "hot line" for parents to call after routine hours before accessing ER services.

Benefit Design

- Review copays to ascertain whether they impede appropriate use of routine ambulatory care.

Patient's Name _____

| Asthma | Date | Date | Date | Date |
|---|---|---|---|---|
| 1. Administer annual flu vaccine | | | | |
| Due to illness, not given but discussed benefits and set future date | | | | |
| | | | | |
| 2. Completed a current medication review: | | | | |
| Weight recorded on chart | | | | |
| Allergies noted and updated | | | | |
| Discussed possible side effects | | | | |
| Reviewed possible drug interactions if prescribing theophylline | | | | |
| If steroids prescribed, documentation of frequency, dose and cycles in calendar year | | | | |
| If it applies, how to schedule doses of medication to be given during school hours | | | | |
| Proper use of inhaler | | | | |
| Update medication record | | | | |
| | | | | |
| 3. Discussion on current smoking habits in household | | | | |
| | | | | |
| 4. Documentation of breath sounds | | | | |
| Peak flow or spirometry values charted | | | | |
| Narrative noted describing breath sounds | | | | |
| | | | | |
| 5. Documentation of complaints: | | | | |
| Loss of appetite | | | | |
| Loss of sleep | | | | |
| Hyperactivity, jitters | | | | |
| Multiple vague complaints | | | | |
| Difficulty after a change in medication | | | | |

| Page 2 - Asthma | Date | Date | Date | Date |
|---|---|---|---|---|
| 6. Documentation of stress issues seen in chronic illness: | | | | |
| Frequent unscheduled office visits | | | | |
| Frequent phone calls from parent | | | | |
| ER/urgent care episodes (discuss appropriate use) | | | | |
| Inconsistent use of medications | | | | |
| | | | | |
| 7. Discussion of contributing socio-economic factors: | | | | |
| Change in home status | | | | |
| Change in school conditions | | | | |
| Inability to compete in organized sports | | | | |
| Other illness or surgery | | | | |
| | | | | |
| 8. Parent/child education by a medical professional: | | | | |
| Medication side effects & when to report them | | | | |
| How to communicate acute symptoms to physician | | | | |
| How to deal with a crisis situation | | | | |
| How to travel with an asthmatic child | | | | |
| Return demonstration on use of inhalant | | | | |
| | | | | |
| 9. Contributing illness history documented | | | | |
| Chronic ear infection | | | | |
| Pneumonia/bronchitis | | | | |
| Chronic rhinitis/pharyngitis | | | | |
| Frequent sore throat | | | | |
| Tonsillitis | | | | |
| | | | | |
| 10. Physician's signature/initials | | | | |

```
/*********************************************
*                                            *
* PROGRAM NAME:   CESAREAN/PRENATAL DATA  (CSECPREN.SAS) *
* PROGRAMMER:     LYNN M THOME/KEVIN DIVINE  *
* FILES USED:     CESAREAN.DATA              *
* FILES CREATED:                             *
* REQUESTER:      EILEEN PETERSON  SURVEILLANCE MODEL *
* DATE CREATED:                              *
* DATE MODIFIED:                             *
* OBJECTIVE:      To calculate the cesarean rate of *
*                 specific plans and print them into *
*                 charts.                    *
*                                            *
*********************************************/

/* MACRO NAMES TO BE CHANGED TO SPECIFIC PLAN DETAILS */

%LET DR=PVD.DOCTOR;
%LET RX=PVD.PHARM;
%LET PR=PVD.PROVIDER;
%LET DR2=PVD.DOCTOR2;
%LET DIAB=PVD.ALLDIAB;
%LET VISC=PVD.CSECVIS;
%LET VISP=PVD.PRENAMNI;
%LET DIABP=PVD.PRENDIAB;
%LET VISP1=PVD.PRENVIS;
%LET YR=90;
%LET PLAN=PHYSICIANS HEALTH PLAN OF OCEAN STATE - 1990;
FILENAME PRENRPT1 'PRENRPT1.LST';
FILENAME PRENRPT2 'PRENRPT2.LST';
FILENAME CSECRPT4 'CSECRPT4.LST';

PROC FORMAT;
   VALUE AGEFMT
       LOW-20='UNDER 20 YEARS'
       20-24='20-24 YEARS'
       25-29='25-29 YEARS'
       30-34='30-34 YEARS'
       35-39='35-39 YEARS'
       40-HIGH='40+ YEARS';

PICTURE PCTFMT
       LOW-HIGH = '00.0%';
RUN;

DATA BAD(KEEP=MEMBID AGE CPTCODE) CESAREAN(DROP=YEAR PROVTYPE FLAG);
   SET &DR;
   BY MEMBID;
   RETAIN FLAG 0;
   WHERE (MEMBSEX='F');
   FORMAT CPTDATE FROMDATE THRUDATE MMDDYY8.;
   AGE=INT(INTCK('MONTH',BIRTHDTE,CPTDATE)/12);
   IF AGE<13 THEN DELETE;
   IF FIRST.MEMBID THEN FLAG=0;
   PROVTYPE=INPUT(SUBSTR(PROVID,1,2),2.);
   MISCAR=('59800'<=CPTCODE<='59811');
   VAGINAL=('59400'<=CPTCODE<='59401');
   CSECT=('59500'<=CPTCODE<='59581');
   IF MISCAR THEN FLAG=1;
   IF (YEAR(CPTDATE)=(1900+&YR)) AND (VAGINAL OR CSECT)
       AND (PROVTYPE IN (1,7,17)) THEN OUTPUT CESAREAN;
```

APPENDIX D

```
IF LAST.MEMBID AND FLAG THEN OUTPUT BAD;
RUN;

PROC SORT DATA=CESAREAN;
BY MEMBID DESCENDING CPTDATE CPTCODE;
RUN;

DATA CESAREAN;
MERGE CESAREAN(IN=A) BAD(IN=B);
BY MEMBID;
IF A AND NOT(B);
RUN;

DATA TEMPV TEMPC;
SET CESAREAN;
RETAIN FLAGV FLAGC;
BY MEMBID DESCENDING CPTDATE CPTCODE;
IF FIRST.CPTDATE THEN DO;
   FLAGV=0;
   FLAGC=0;
END;
IF CPTCODE IN ('59400','59410') THEN FLAGV=1;
IF ('59500'=CPTCODE='59581') THEN FLAGC=1;
IF LAST.CPTDATE THEN DO;
   IF FLAGC THEN OUTPUT TEMPC;
   IF FLAGV AND NOT(FLAGC) THEN OUTPUT TEMPV;
   END;
RUN;

DATA V(DROP=X FLAG1);
RETAIN BABY1;
SET TEMPV;
BY MEMBID;
IF FIRST.MEMBID THEN DO;
   BABY1=CPTDATE;
   V=1;
   C=0;
   OUTPUT;
END;
X=ABS(INTCK('MONTH',CPTDATE,BABY1));
RUN;

DATA C(DROP=X FLAG1);
RETAIN BABY1;
SET TEMPC;
BY MEMBID;
IF FIRST.MEMBID THEN DO;
   BABY1=CPTDATE;
   V=0;
   C=1;
   OUTPUT;
END;
X=ABS(INTCK('MONTH',CPTDATE,BABY1));
RUN;

DATA CESAREAN;
SET C V;
FORMAT AGE AGEFMT.;
RUN;
```

```
DATA &VISC;
SET CESAREAN(KEEP=MEMBID PROVID CPTDATE);
RUN;

TITLE1; TITLE2; TITLE3; TITLE4;
FOOTNOTE1; FOOTNOTE2; FOOTNOTE3;

DATA OVERALL(KEEP=VALUE TOTAL CSECTOT PERCENT);
 SET CESAREAN END=LASTOBS;
  RETAIN VALUE 1;
  IF C=1 THEN CSECTOT+1;
  TOTAL+1;
  IF LASTOBS THEN DO;
    PERCENT=(CSECTOT/TOTAL)*100;
    CALL SYMPUT('RATE',PUT(PERCENT,5.1));
    OUTPUT;
  END;
RUN;

DATA NATNORM;
  INPUT VALUE TOTAL CSECTOT PERCENT;
  CARDS;
2 0 0 24.70
;
RUN;

PROC APPEND BASE=OVERALL DATA=NATNORM;
RUN;

PROC SORT DATA=OVERALL;
BY VALUE;
RUN;

DATA NUMBER;
  LENGTH FUNCTION COLOR STYLE $8.;
  LENGTH XSYS YSYS POSITION $1.;
  RETAIN POSITION '5';
  SET OVERALL;

XSYS='2';
  YSYS='2';
  FUNCTION='LABEL';
  STYLE='NONE';
  COLOR='BLUE';
  X=VALUE;
  Y=PERCENT+4.3;
  TEXT=COMPRESS(PUT(PERCENT,F5.1),' ')||'% ';
  OUTPUT;
  FUNCTION='LABEL';
  STYLE='NONE';
  COLOR='RED';
  X=VALUE;
  Y=PERCENT+2.5;
  IF CSECTOT NE 0 THEN TEXT='('||COMPRESS(PUT(TOTAL,F4.),' ')||')';
    ELSE TEXT='---';
  OUTPUT;
RUN;

GOPTIONS RESET=(AXIS, LEGEND, PATTERN, SYMBOL, TITLE, FOOTNOTE)
    HTEXT= FTEXT= CTEXT= TARGET= GACCESS= HPOS= VPOS=;
```

```
GOPTIONS DEVICE=HPLJ300 FTEXT=NONE CTEXT=BLUE
        HTEXT=1 COLORS=(BLUE) NOBORDER ROTATE=LANDSCAPE;

TITLE1 C=CYAN J=CENTER F=CENTX H=1.5 LS=2 'CESAREAN SECTION RATES';
TITLE2 C=CYAN J=CENTER F=CENTX H=1 "&PLAN";
TITLE3 C=CYAN J=LEFT F=CENTX H=1 LS=2 'CESAREAN_1';

FOOTNOTE1 C=GREEN F=CENTX J=LEFT H=1
'CESAREAN_1: presents the plans total Cesarean section rate compared to the national rate. The Cesarean section rate';
FOOTNOTE2 C=GREEN F=CENTX J=LEFT H=1
'is defined as the proportion of all deliveries represented by Cesarean sections (Cesarean sections/total deliveries).';

PATTERN1 V=E C=GREEN;
PATTERN2 V=E C=GREEN;
PATTERN3 V=E C=GREEN;

AXIS1 LABEL=NONE
      OFFSET=(2 CM)
      VALUE=(C=BLUE H=1
         T=1 'Total'
         T=2 'National'    J=C 'Rate');
AXIS2 LABEL=(A=270 R=90 H=1 'CESAREAN RATE')
      ORDER=0 TO 50 BY 10;

PROC GCHART DATA=OVERALL;
   VBAR VALUE / DISCRETE
         SUMVAR=PERCENT
         SPACE=6
         WIDTH=9
         MAXIS=AXIS1
         RAXIS=AXIS2
         ANNOTATE=NUMBER
         PATTERNID=MIDPOINT;
RUN;

TITLE1; TITLE2; TITLE3; TITLE4;
FOOTNOTE1; FOOTNOTE2; FOOTNOTE3; FOOTNOTE4;

DATA AGE1 AGE2 AGE3 AGE4 AGE5 AGE6;
SET CESAREAN;
SELECT;
   WHEN (AGE <= 19) OUTPUT AGE1;
   WHEN (20 <= AGE <= 24) OUTPUT AGE2;
   WHEN (25 <= AGE <= 29) OUTPUT AGE3;
   WHEN (30 <= AGE <= 34) OUTPUT AGE4;
   WHEN (35 <= AGE <= 39) OUTPUT AGE5;
   WHEN (40 <= AGE) OUTPUT AGE6;
   OTHERWISE;
END;
RUN;

DATA OVERALL(KEEP=CSECTOT TOTAL);
SET CESAREAN END=LASTOBS;
   IF C=1 THEN CSECTOT+1;
   TOTAL+1;
   IF LASTOBS;
RUN;

DATA OVERPCT;
SET OVERALL;
```

```
    AGEPCT=(CSECTOT/TOTAL)*100;
    FORMAT AGEPCT 5.1;
RUN;

DATA AGE1(KEEP=CSECTOT TOTAL);
SET AGE1 END=LASTOBS;
    IF C=1 THEN CSECTOT+1;
    TOTAL+1;
    IF LASTOBS;
RUN;

DATA AGE1PCT;
SET AGE1;
    AGEPCT=(CSECTOT/TOTAL)*100;
    FORMAT AGEPCT 5.1;
RUN;

DATA AGE2(KEEP=CSECTOT TOTAL);
SET AGE2 END=LASTOBS;
    IF C=1 THEN CSECTOT+1;
    TOTAL+1;
    IF LASTOBS;
RUN;

DATA AGE2PCT;
SET AGE2;
    AGEPCT=(CSECTOT/TOTAL)*100;
    FORMAT AGEPCT 5.1;
RUN;

DATA AGE3(KEEP=CSECTOT TOTAL);
SET AGE3 END=LASTOBS;
    IF C=1 THEN CSECTOT+1;
    TOTAL+1;
    IF LASTOBS;
RUN;

DATA AGE3PCT;
SET AGE3;
    AGEPCT=(CSECTOT/TOTAL)*100;
    FORMAT AGEPCT 5.1;
RUN;

DATA AGE4(KEEP=CSECTOT TOTAL);
SET AGE4 END=LASTOBS;
    IF C=1 THEN CSECTOT+1;
    TOTAL+1;
    IF LASTOBS;
RUN;

DATA AGE4PCT;
SET AGE4;
    AGEPCT=(CSECTOT/TOTAL)*100;
    FORMAT AGEPCT 5.1;
RUN;

DATA AGE5(KEEP=CSECTOT TOTAL);
SET AGE5 END=LASTOBS;
    IF C=1 THEN CSECTOT+1;
    TOTAL+1;
```

```
  IF LASTOBS;
RUN;

DATA AGE5PCT;
SET AGE5;
  AGEPCT=(CSECTOT/TOTAL)*100;
  FORMAT AGEPCT 5.1;
RUN;

DATA AGE6(KEEP=CSECTOT TOTAL);
SET AGE6 END=LASTOBS;
  IF C=1 THEN CSECTOT+1;
  TOTAL+1;
  IF LASTOBS;
RUN;

DATA AGE6PCT;
SET AGE6;
  AGEPCT=(CSECTOT/TOTAL)*100;
  FORMAT AGEPCT 5.1;
RUN;

DATA OVERPCT;
SET OVERPCT AGE1PCT AGE2PCT AGE3PCT AGE4PCT AGE5PCT AGE6PCT;
RUN;

DATA AGEPCT;
SET OVERPCT;
  COUNT+1;
  LABEL COUNT='AGE OF MEMBER'
        CSECTOT='CESAREAN COUNT'
        TOTAL='TOTAL BIRTHS'
        AGEPCT='PERCENT CESAREAN';
RUN;

DATA NUMBER;
  LENGTH FUNCTION COLOR STYLE $8.;
  LENGTH XSYS YSYS POSITION $1.;
  RETAIN POSITION '5';
  SET AGEPCT;

XSYS='2';
  YSYS='2';
  FUNCTION='LABEL';
  STYLE='NONE';
  COLOR='BLUE';
  X=COUNT;
  Y=AGEPCT+6.8;
  TEXT=COMPRESS(PUT(AGEPCT,F5.1),'')||'% ';
  OUTPUT;
  FUNCTION='LABEL';
  STYLE='NONE';
  COLOR='RED';
  X=COUNT;
  Y=AGEPCT+2.8;
  TEXT='/'||COMPRESS(PUT(TOTAL,F4.),'')||'/';
  OUTPUT;
RUN;

GOPTIONS RESET=(AXIS, LEGEND, PATTERN, SYMBOL, TITLE, FOOTNOTE)
```

```
        HTEXT= FTEXT= CTEXT= TARGET= GACCESS= HPOS= VPOS=;
GOPTIONS DEVICE=HPLJ300 FTEXT=NONE CTEXT=BLUE
        HTEXT=1 COLORS=(BLUE) NOBORDER ROTATE=LANDSCAPE;

TITLE1 C=CYAN J=C F=CENTX H=1.5 LS=2 'CESAREAN SECTION RATES BY AGE';
TITLE2 C=CYAN J=C F=CENTX H=1.5 'TOTAL';
TITLE3 C=CYAN J=C F=CENTX H=1 "&PLAN";
TITLE4 C=CYAN J=L F=CENTX H=1 LS=2 'CESAREAN_2';

FOOTNOTE1 C=GREEN F=CENTX J=LEFT H=1
   'CESAREAN_2: presents age-specific rates for Cesarean section.';

PATTERN1 V=L1 C=GREEN;
PATTERN2 V=E  C=GREEN;
PATTERN3 V=E  C=GREEN;
PATTERN4 V=E  C=GREEN;
PATTERN5 V=E  C=GREEN;
PATTERN6 V=E  C=GREEN;
PATTERN7 V=E  C=GREEN;

AXIS1 LABEL=('AGE GROUP')
      VALUE=(C=GREEN H=.75
          T=1 'Overall'
          T=2 'Less'    J=C 'than 20'
          T=3 '20-24'
          T=4 '25-29'
          T=5 '30-34'
          T=6 '35-39'
          T=7 'Greater' J=C 'than 39');
AXIS2 LABEL=('CESAREAN RATE')
      ORDER=0 TO 100 BY 10;

PROC GCHART DATA=AGEPCT;
   VBAR COUNT / DISCRETE
          SUMVAR=AGEPCT
          WIDTH=6
          MAXIS=AXIS1
          RAXIS=AXIS2
          ANNOTATE=NUMBER
          PATTERNID=MIDPOINT;
RUN;
QUIT;

PROC SORT DATA=CESAREAN;
BY MEMBID;
RUN;

DATA HOSPNBR1;
MERGE CESAREAN(IN=A RENAME=(CPTDATE=PROCDATE CPTCODE=PROC) DROP=FROMDATE THRUDATE)
      &DR(IN=B RENAME=(PROVID=HOSPNBR));
BY MEMBID;
WHERE (SITECODE=4);
HSP=INPUT(SUBSTR(HOSPNBR,1,2),2.);
IF A=B;
IF (50<=HSP<=55) AND (-8<=INTCK('DAY',PROCDATE,FROMDATE)<=8);
RUN;

PROC SORT DATA=HOSPNBR1;
BY MEMBID HOSPNBR;
RUN;
```

```
DATA HOSPNBR;
SET HOSPNBR1;
BY MEMBID HOSPNBR;
IF FIRST.HOSPNBR;
RUN;

PROC SORT DATA=HOSPNBR;
BY HOSPNBR;
RUN;

DATA HOSPCNT;
SET HOSPNBR END=LASTOBS;
BY HOSPNBR;
IF FIRST.HOSPNBR THEN DO;
   CSEC=0;
   DEL=0;
END;
IF FLAGC THEN CSEC+1;
DEL+1;
IF LAST.HOSPNBR THEN DO;
   CSECRATE=(CSEC/DEL)*100;
   TOTHOSP+1;
   PI=(CSEC/DEL)*100;
   OUTPUT;
END;
IF LASTOBS THEN CALL SYMPUT('HSP',PUT(TOTHOSP,3.));
RUN;

GOPTIONS RESET=(AXIS, LEGEND, PATTERN, SYMBOL, TITLE, FOOTNOTE)
        HTEXT= FTEXT= CTEXT= TARGET= GACCESS= HPOS= VPOS=;
GOPTIONS DEVICE=HPLJ300 FTEXT=NONE CTEXT=BLUE
        HTEXT=1 COLORS=(BLUE) NOBORDER ROTATE=LANDSCAPE;

PROC SORT DATA=HOSPCNT;
BY DESCENDING DEL;
RUN;

DATA HOSPCNT;
SET HOSPCNT;
IF (DEL >= 10) THEN DO;
   UPPER=(&RATE+(1.645*SQRT((&RATE*(100-&RATE))/DEL)));
   LOWER=(&RATE-(1.645*SQRT((&RATE*(100-&RATE))/DEL)));
END;
ELSE DO;
   UPPER=.;
   LOWER=.;
END;
P=&RATE;
LABEL PI='CESAREAN RATE'
      DEL='# OF PLAN DELIVERIES PER HOSPITAL';
RUN;

TITLE1 H=1.5 F=CENTX C=BLUE J=C LS=2 'HOSPITAL CESAREAN SECTION RATES';
TITLE2 H=1 F=CENTX C=BLUE  J=C    "&PLAN";
TITLE3 H=1  F=CENTX C=BLUE J=L LS=2 'CESAREAN_3';

FOOTNOTE1 H=1 C=RED F=CENTX J=L
  'CESAREAN_3: presents the Cesarean rate in each hospital plotted against the number of plan deliveries in that hospital. The upper';
FOOTNOTE2 H=1 C=RED F=CENTX J=L
  'and lower 95% confidence bound for the average hospital rate is shown. Those Cesarean section rates above the upper bound can be';
```

```
FOOTNOTE3 H=1 C=RED F=CENTX J=L
 'treated as significantly greater than the average hospital cesarean rate and may merit additional investigation.';

SYMBOL1 C=CYAN      V='+' ;
SYMBOL2 C=GREEN I=JOIN L= 1 V=NONE;
SYMBOL3 C=GREEN I=JOIN L= 1 V=NONE;
SYMBOL4 C=GOLD I=JOIN L= 4 V=NONE;

PROC GPLOT DATA=HOSPCNT;
   PLOT PI*(DEL) LOWER*(DEL) UPPER*(DEL) P*(DEL) / OVERLAY FRAME
;
RUN;
QUIT;

GOPTIONS RESET=(AXIS, LEGEND, PATTERN, SYMBOL, TITLE, FOOTNOTE)
         HTEXT= FTEXT= CTEXT= TARGET= GACCESS= HPOS= VPOS=;
GOPTIONS DEVICE=HPLJ300 FTEXT=NONE CTEXT=BLUE
         HTEXT=.9 COLORS=(BLUE) NOBORDER ROTATE=LANDSCAPE;

PROC SORT DATA=HOSPCNT;
BY HOSPNBR;
RUN;

DATA HOSP;
MERGE HOSPCNT(IN=A KEEP=HOSPNBR DEL CSEC PI UPPER) &PR(IN=B RENAME=(PROVID=HOSPNBR));
BY HOSPNBR;
IF A=B;
RUN;

PROC SORT DATA=HOSP;
BY DESCENDING DEL;
RUN;

DATA HOSP;
SET HOSP;
IF (DEL >= 10) AND (PI > UPPER) THEN MARK='* EXCEEDS UPPER BOUND';
ELSE MARK=' ';
IF DEL.10 THEN CSEC=.;
RUN;

DATA _NULL_;
SET HOSP;
FILE CSECRPT4;
IF _N_=1 THEN DO;
   PUT // @51 '# OF PLAN' @68 '# OF' @80 'CESAREAN';
   PUT @10 'HOSPITAL NAME' @50 'DELIVERIES' @65 'CESAREAN' @82 'RATE'//;
END;
PUT @10 NAME @53 DEL 4. @67 CSEC 4. @80 PI 8.4 @90 MARK;
RUN;

TITLE1 C=CYAN F=CENTX H=1.5 J=C LS=2 'CESAREAN SECTION RATE BY HOSPITAL';
TITLE2 C=CYAN F=CENTX H=1  J=C    "&PLAN";
TITLE3 C=CYAN F=CENTX H=1  J=L LS=2 'CESAREAN_4';

FOOTNOTE1 H=1 J=L F=CENTX C=GREEN
 'CESAREAN_4: presents the Cesarean section data for the plan by hospital. The Cesarean section rate and the 95%';
FOOTNOTE2 H=1 J=L C=GREEN F=CENTX
 'confidence bound for each hospital is shown. Hospitals exceeding the upper bound are presented in the last column.';

PROC GPRINT FILEREF=CSECRPT4;
```

RUN;
QUIT;

QSM
Quality Screen – Cesarean Section

I. CLAIMS ANALYSIS

A. Population to be Studied: all women who had a delivery.

B. Quality Indicators:

1.  Rationale for Selection: The continued rise in the Cesarean section rate has created general concern about the appropriateness of many of the Cesarean sections performed. Although there is no consensus on the ideal Cesarean section rate, there is agreement that Cesarean section rates above the national average could indicate the existence of a large number of inappropriate Cesarean sections. The claims data screen calculates the rate of Cesarean sections as a percent of all deliveries and compares it to the national rate determined by the National Center for Health Statistics.[1]

2.  Claims Indicators: The following indicators can be measured in the Cesarean section claims data screen:

Overall Cesarean Section Rate:

A comparison of the health plan's rate with the national average.

II. DETAILED ANALYSIS

A. Population to be Studied: women with a Cesarean delivery.

B. Rationale for Selection: An analysis of indications for Cesarean section may be conducted to determine appropriateness of care and the frequency of the indications compared with national averages.

---

[1] National Center for Health Statistics. *Health, United States, 1989.* Public Health Service. Washington, D.C. U.S. Government Printing Office, March 1989.

APPENDIX E

CESAREAN SECTION RATES
CESAREAN_1
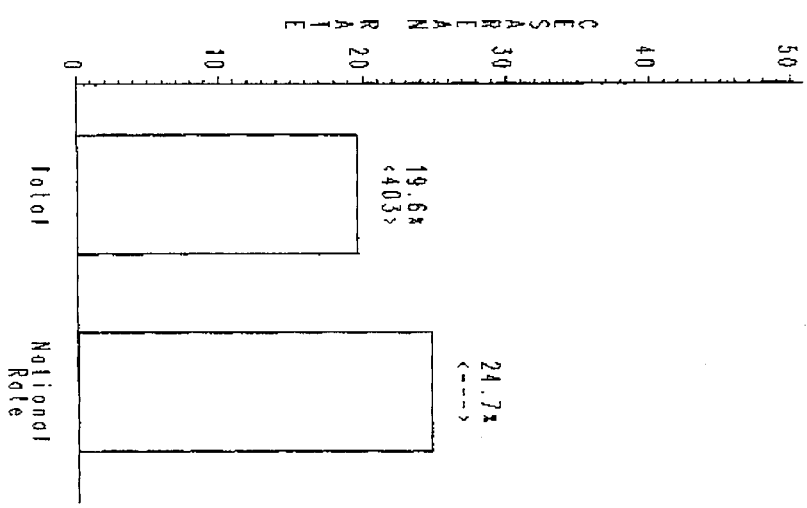
CESAREAN_1: presents the plans total Cesarean section rate compared to the national rate. The Cesarean section rate is defined as the proportion of all deliveries represented by Cesarean sections (Cesarean sections/total deliveries).

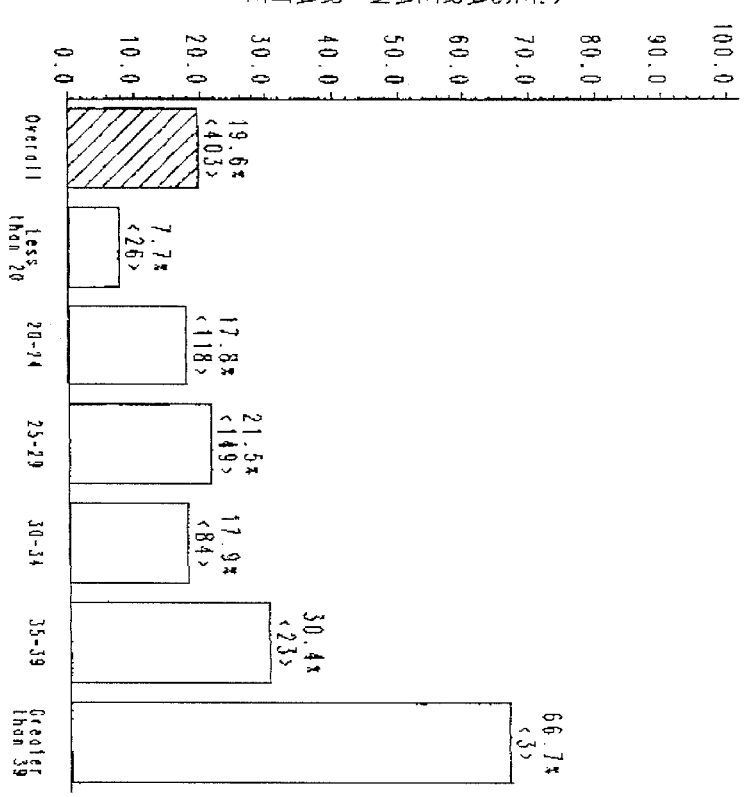
CESAREAN_2: presents age-specific rates for Cesarean section.

HOSPITAL CESAREAN SECTION RATES

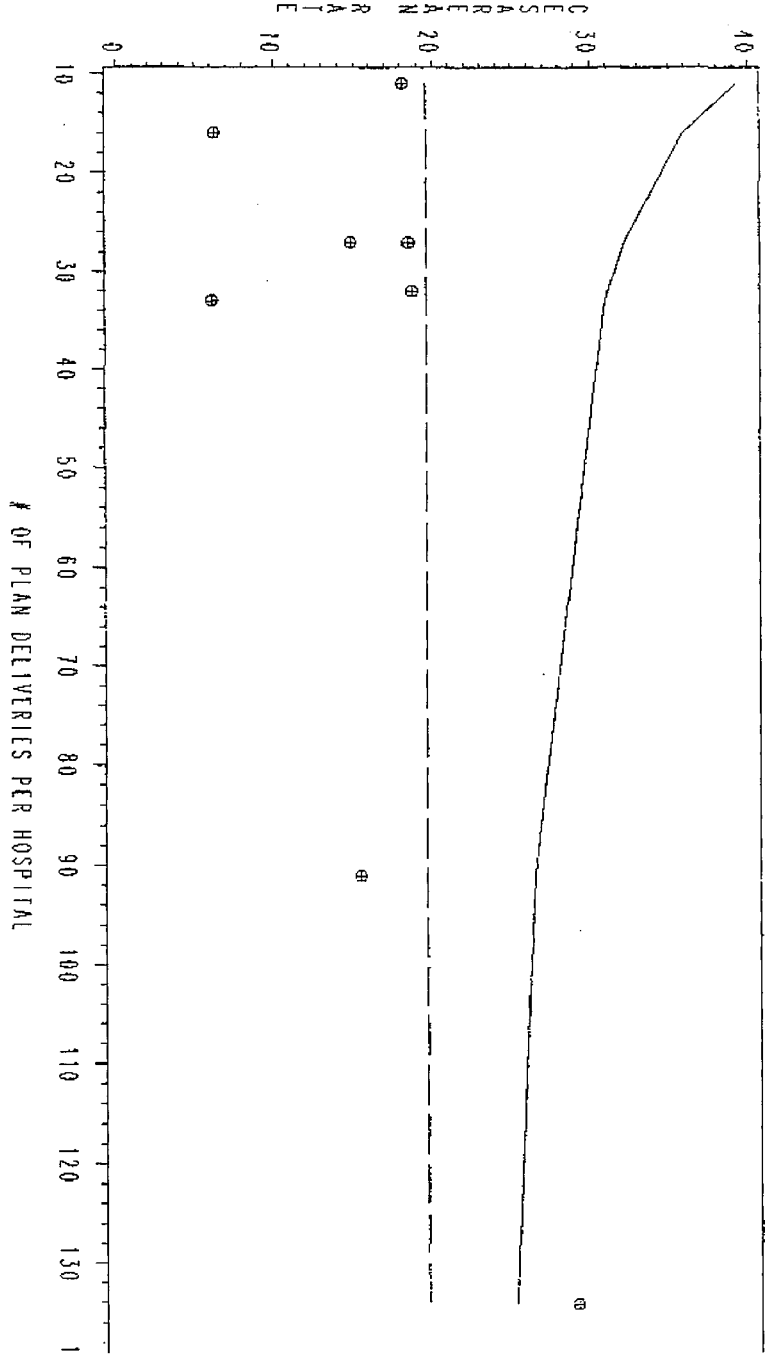

CESAREAN_3

CESAREAN_3: presents the Cesarean rate in each hospital plotted against the number of plan deliveries in that hospital. The upper 95% confidence bound for the average hospital rate is shown. Those Cesarean section rates above the upper bound can be treated as significantly greater than the average hospital cesarean rate and may merit additional investigation.

CESAREAN SECTION RATE BY HOSPITAL

CESAREAN_4

| HOSPITAL NAME | # OF PLAN DELIVERIES | # OF CESAREAN | CESAREAN RATE | |
|---|---|---|---|---|
| | 134 | 39 | 29.1045 | * EXCEEDS UPPER BOUND |
| | 91 | 14 | 15.3846 | |
| | 33 | 2 | 6.0606 | |
| | 32 | 6 | 18.7500 | |
| | 27 | 4 | 14.8148 | |
| | 27 | 5 | 18.5185 | |
| | 16 | 1 | 6.2500 | |
| | 11 | 2 | 18.1818 | |
| | 6 | . | 0.0000 | |
| | 5 | . | 0.0000 | |
| | 3 | 2 | 66.6667 | |
| | 2 | . | 0.0000 | |
| | 1 | 1 | 100.0000 | |
| | 1 | . | 0.0000 | |

CESAREAN_4: presents the Cesarean section data for the plan by hospital. The Cesarean section rate and the 95% confidence bound for each hospital is shown. Hospitals exceeding the upper bound are presented in the last column.

QSM Quality Screen:        Cesarean Section

Results:

Date:

Data Source:               Claims Data

The plan's Cesarean section rate is lower than the national rate.

Plan Cesarean section rate: 19.6% [Cesarean_1]

National rate: 24.7% [Cesarean_1]

The Cesarean section rate increases with age.

This pattern conforms to national norms.

Cesarean section rate for PHP members over 40 is the highest of any age group: 34.8%. [Cesarean_2]

One hospital had a significantly higher Cesarean section rate than the plan rate.

One hospital was identified in the network for possible further investigation: [Cesarean_4]

---

[1] This hospital had a Cesarean section rate which was higher than the average rate at a statistically significant level (95% confidence bound).

Quality Management Actions Matrix

| | Report QSM to MDs | Practice Guide-lines | Specific Medical Record Flowsheets | Reimburse MD | Provider Discipline | Patient Education & Reminder | Case Mgt. Programs | Patient's Access to Care | Change Benefit Design |
|---|---|---|---|---|---|---|---|---|---|
| DIABETES | ■ | ■ | ■ | ■ | | ■ | | | |
| PEDIATRIC ASTHMA | ■ | ■ | ■ | ■ | | ■ | | | |
| PRENATAL CARE | ■ | ■ | ■ | | | ■ | | | |
| "C-SECTION" | ■ | ■ | | | | | | | |
| PED. IMMUNIZATION | ■ | ■ | ■ | ■ | | ■ | | | |
| CERVICAL CANCER | ■ | ■ | ■ | | | ■ | | | |
| BREAST CANCER | ■ | | | | | ■ | ■ | | |
| READMISSION | | | | | | | | | ■ |

This matrix illustrates some of the appropriate actions to consider in effecting quality improvement. The shaded areas indicate those actions which are suggested to be the most feasible.

QSM

Quality Management Actions

CESAREAN SECTION

These quality management actions are presented as a menu of possible ways to improve quality. They can be used as illustrated or revised to meet specific community needs.

Report to Physicians

- Communicate results of QSM analysis to physicians.
- Discuss possible actions by specific clinic to impact the Cesarean section rate.

Establish Guidelines

- Establish medical necessity criteria for Cesarean section.

Medical Record Flow Sheet

- Design and implement a consent sheet that includes appropriateness indications for repeat section, physician-patient discussion and patient's signature of understanding.

Patient Education

- Member newsletter article describing rates and issues of appropriateness in Cesarean sections.
- Highlight VBAC program in member newsletter; benefit of this procedure, and hospitals and physicians that support the program.

Case Management

- Partnership between HMO and major OB clinic(s) to design and support a VBAC program with appropriateness criteria, education, fee review and patient follow up.

Cesarean section - Page 2

Physician Reimbursement

- Evaluate and adjust the fees to physicians who are willing to support the VBAC program.
- Design incentives to hospitals for support of program.

(NOTE: Before implementing, please call UHC Health Services for most current version of this abstracting tool.)

Abstract No. _____
Physician's Name: _____
Member Name: _____
Date of Birth: _____
Mem. No: _____
Abstractor Code: _____
Date of Abstraction: _____
Hospital: _____
Date of Service: _____

Cesarean Section

Medical Record Data Elements

1. Name      _____   _____   __
             (Last)           (First)  (MI)

2. Birth Date    __/__/__
                 MO DAY YEAR

3. Race    ___ White    ___ Black
           ___ Asian    ___ Hispanic
           ___ Other    ___ Not specified on chart 4. Was a Cesarean section performed during the admission noted on the label?

___ Yes

___ No STOP REVIEW

5. Please list the dates for:

Admission __ __/__ __/__ __

Cesarean section __ __/__ __/__ __

Discharge __ __/__ __/__ __

6. Is the admitting physician, specified on label, the same as the physician who performed the Cesarean section?

____ Yes

____ No

6a. If no, please specify the physician who performed the procedure:

_____
   (Last, First, MI)

7. Was the Cesarean section scheduled or unscheduled?

____ Scheduled

____ Unscheduled

8. Was this a primary (first time) Cesarean section?

___ Yes

___ No

9. Was this a repeat Cesarean section?

___ Yes

___ No

9a. If Yes, did the prenatal record indicate a discussion between patient/physician concerning a trial labor and possible vaginal delivery? (V-BAC)

___ Yes

___ No

___ Not applicable

9b. Does the medical record document the patient's refusal to attempt a trial of labor following a previous Cesarean section?

___ Yes

___ No

___ Not Applicable

10. Did indication for this Cesarean section include any of the following?

|  | YES | NO |
|---|---|---|
| Failure to progress | ___ | ___ |
| Prematurity without maternal or fetal distress | ___ | ___ |
| Eclampsia/Toxemia | ___ | ___ |
| Diabetes with uncontrolled hyperglycemia or fetal jeopardy by challenge test | ___ | ___ |
| Chronic renal disease with fetal jeopardy | ___ | ___ |
| Hypertensive cardiovascular disease | ___ | ___ |
| Malpresentation | ___ | ___ |
| Multifetal gestations | ___ | ___ |
| Abruptio placenta | ___ | ___ |
| Placenta previa | ___ | ___ |
| Chorioamnionitis | ___ | ___ |
| Fetal congenital anomalies | ___ | ___ |
| Post term pregnancy | ___ | ___ |
| Excessive fetal size | ___ | ___ |
| Fetal distress | ___ | ___ |
| Dystocia | ___ | ___ |

12. During hospitalization, did any of the following conditions occur:

|  | YES | NO |
|---|---|---|
| Post partum hemorrhage | ___ | ___ |
| Complications of the administration of anesthesia | ___ | ___ |
| Maternal hypotension syndrome | ___ | ___ |
| Major puerperal infection | ___ | ___ |
| Pulmonary embolism | ___ | ___ |

13. Following discharge after a Cesarean section, did the patient experience any of the following conditions:

|  | YES | NO |
|---|---|---|
| Delayed and secondary postpartum hemorrhage | ___ | ___ |
| Postpartum coagulation defects | ___ | ___ |
| Venous complications in pregnancy and the puerperium | ___ | ___ |
| Superficial thrombophlebitis | ___ | ___ |
| Deep phlebothromboses | ___ | ___ |

12. During hospitalization, did any of the following conditions occur:

|  | YES | NO |
|---|---|---|
| Post partum hemorrhage | ___ | ___ |
| Complications of the administration of anesthesia | ___ | ___ |
| Maternal hypotension syndrome | ___ | ___ |
| Major puerperal infection | ___ | ___ |
| Pulmonary embolism | ___ | ___ |

13. Following discharge after a Cesarean section, did the patient experience any of the following conditions:

|  | YES | NO |
|---|---|---|
| Delayed and secondary postpartum hemorrhage | ___ | ___ |
| Postpartum coagulation defects | ___ | ___ |
| Venous complications in pregnancy and the puerperium | ___ | ___ |
| Superficial thrombophlebitis | ___ | ___ |
| Deep phlebothromboses | ___ | ___ |

13a. If Yes, did readmission result:

_____ Yes  _____
                Admitting Diagnosis

_____
                Date of Service

_____ No

QSM

Cesarean section

Medical Record Abstraction

INSTRUCTIONS

You will be reviewing information in the chart primarily for visits and or services delivered between (date range). However, some questions may specify other time windows, or periods of time prior to (date range) for abstraction - please watch these carefully. No information beyond (date range) should be reviewed. Accuracy is very important.

Be sure to complete all questions on the abstraction form. A sample form is attached for reference.

Please use a black pen to complete the form. Print all information (for ease of data entry).

Below are instructions for completion of the form. Please enter information as shown.

Please remember to check and note if you are to abstract information from more than the physician's office (the hospital record, or ER record). Please keep the form intact until it is completed in its entirety.

To ensure that the correct medical record is being abstracted, please verify the following information on the form with the medical record:

Name
    Date of Birth
    PHP Member number (if available)

Write in your abstractor code number and date of abstraction:

Name, Abstractor number

1. NAME
   Fill in the name as it appears on chart in Last name, First name, Middle Initial order. For example Doe   John   P.

2. BIRTH DATE
   Enter the birth date provided on the medical record in month, day, year format. For example, Sept. 9, 1944 will be written as 09/09/44.

3. RACE

Check appropriate blank. If not specified on chart, check NOT SPECIFIED.

There is no need to specify the race if "Other" is checked.

4. Cesarean section PERFORMED

Review entire chart to determine if a Cesarean section has been performed.

If it is listed, check YES and complete the abstract form.

If a Cesarean section was not performed, check NO and STOP THE REVIEW.

5. DATES
   Review the chart for the following information regarding the Cesarean section that was performed:

- Admission
   - Cesarean section
   - Discharge

Enter the dates on the spaces provided.

6. PHYSICIAN
   Review the medical record to determine the name of the admitting physician.

If the admitting physician (specified on the label) and the physician who performed the Cesarean section are the same, check YES.

If the admitting physician and the physician who performed the Cesarean section are different, check NO and answer question 6a.

6a. Enter the name of the physician who performed the Cesarean section.
    Enter the last name first.

SCHEDULED Cesarean section
7. Review the medical record to determine if the Cesarean section was scheduled.
   If it was, check YES.

If the Cesarean section was unscheduled, check UNSCHEDULED.

8. PRIMARY Cesarean section
   Review the chart to determine if this was a primary (first time) Cesarean section.
   Check YES, if this was the first performed on the patient.

If this is a second or other Cesarean section, check NO.

9. REPEAT Cesarean section
   Review the information in the chart to determine if this Cesarean section was a repeat. If so, check YES and answer questions 9a and 9b.

If this is a not a repeat Cesarean section, check NO.

9a. If this is a repeat Cesarean section, review the record to determine if a discussion had taken place between physician and patient concerning a trial labor and vaginal delivery. If the record indicates this discussion took place, check YES.

If there is record of no such a discussion, check NO.

If there is not documentation in the record either way, check NOT APPLICABLE.

9b. Review the medical record to determine if the patient has refused to attempt a trial labor following a previous Cesarean section.

If the record indicates the patient has refused a trial labor, check YES.

If the record indicates the patient did not refuse a trial labor, check NO.

If the record has no indication of refusal of a trial labor, check NOT APPLICABLE.

10. Review the medical record to determine if any of the following were reasons for the Cesarean section being performed. Check YES where applicable. Check all that apply.
    Failure to progress
    Prematurity without maternal or fetal distress
    Eclampsia/toxemia
    Diabetes with uncontrolled hyperglycemia or fetal jeopardy by challenge test
    Chronic renal disease with fetal jeopardy
    Hypertensive cardiovascular disease
    Malpresentation
    Multifetal gestations
    Abruptio placenta
    Placenta previa
    Chorioamnionitis
    Fetal congenital anomalies
    Post term pregnancy
    Excessive fetal size
    Fetal distress
    Dystocia
    Herpes simplex
    Patient's request
    Previous Cesarean section If the reason is for other than those listed above, check OTHER and indicate on the line the reason for the Cesarean section.

11. Review the medical record to determine if any of the following were experienced by the mother at the time of surgery. Check YES where applicable. Check all that apply.

> Injury to pelvic organs
> Pelvic hematoma
> Maternal distress
> Shock during or following delivery
> Acute renal failure following delivery 12. Review the medical record to determine if any of the following conditions occurred during hospitalization. Check YES where applicable. Check all that apply.

> Post hemorrhage
> Complications of the administration of anesthesia
> Maternal hypotension syndrome
> Major puerperal infection
> Pulmonary embolism 13. Review the medical record to determine if any of the following conditions occurred after discharge. Check YES where applicable. Check all that apply.

> Delayed and secondary postpartum hemorrhage
> Postpartum coagulation defects
> Venous complications in pregnancy and the puerperium
> Superficial thrombophlebitis
> Deep phlebothromboses 13a. If you answered YES to question 13, review the chart to determine if a readmission occurred. If so, check YES and enter the admitting diagnoses on the line provided and the date of service.

If no readmission, check NO.

What is claimed is:

1. In a medical information system comprising a processing unit, at least one memory unit and means for entering information into said medical information system and for providing commands to said medical information system, a method of analyzing health care claims records for an enrolled population to assess quality of care received by enrollees having a specified health care condition and formulate action recommendations to improve care comprising:

(a) providing to said processing unit of said medical information system health care claims records for a selected enrollee population;

(b) defining in the medical information system at least one health care condition in terms of a specified logical relationship among a plurality of health care events relevant to diagnosis and reported in the health care claims records;

(c) identifying in the health care claims records those enrollees meeting the definition for said at least one health care condition;

(d) defining in the medical information system health care quality criteria for said at least one health care condition in terms of a plurality of health care events reported or reportable in the health care claims records, including at least one intervention based on practice guidelines and related to care for the at least one health care condition;

(e) comparing the health care quality criteria for said at least one health care condition to the health care claims records for at least a portion of those enrollees meeting the definition for said at least one health care condition; and (f) developing and outputting from said medical information system a health care quality report based on the comparison of step (e) and including action recommendations for improving health care quality.

2. The method of claim 1 wherein the step of providing health care claims records comprises providing records from a group consisting of: claims records for medical professional services, claims records for hospital services and claims records for pharmaceutical prescriptions.

3. The method of claim 1 wherein multiple health care conditions and corresponding health care quality criteria for said multiple health care conditions are defined.

4. The method of claim I further comprising the steps of:

(g) providing to said processing unit of said medical information system medical records for a selected enrollee population that is a subset of the enrollee population identified as meeting the definition for said at least one health care condition;

(h) defining health care quality criteria for said at least one health care condition also in terms of health care events reported or reportable in the medical records;

(i) comparing the health care quality criteria for said at least one health care condition to the medical records for at least some of those enrollees meeting the definition for said at least one health care condition; and (j) developing and outputting from said medical information system a report based on the comparison of step (i) as well as step (e) and including action recommendations for improving health care quality as defined by said health care quality criteria.

5. The method of claim 1 wherein the step of defining at least one health care condition in terms of health care events relevant to diagnosis and reported in the health care claims records comprises defining a specific health care condition in the nature of a disease or organic dysfunction.

6. The method of claim 5 wherein the at least one health care condition is selected from a group consisting of: pediatric asthma, diabetes mellitus, hypertension, and breast cancer.

7. The method of claim 1 wherein the step of defining at least one health care condition in terms of health care events relevant to diagnosis and reported in the health care claims records further comprises defining a specific health care condition not in the nature of a disease or organic dysfunction.

8. The method of claim 7 wherein the at least one health care condition is selected from a group consisting of: prenatal care, caesarian section, breast cancer screening, cervical cancer screening and pediatric immunizations for a specified age group.

9. The method of claim 1 wherein step (f) comprises developing and outputting from said medical information system a health care quality report that reports statistics on at least one adverse event as an indicator of a health care quality problem.

10. The method of claim 1 wherein step (f) comprises developing and outputting from said medical information system a health care quality report that reports a frequency of occurrence of at least one health care quality criterion.

11. In a medical information system comprising a processing unit, at least one memory unit and means for entering information into said medical information system and for providing commands to said medical information system, a method of analyzing health care claims records for an enrolled population to assess quality of care received by enrollees having a specified health care condition and formulate action recommendations to improve care comprising:

(a) providing to said processing unit of said medical information system health care claims records for a selected enrollee population, said claims records comprising claims records for medical professional services, claims records for hospital services and claims records for pharmaceutical prescriptions;

(b) defining in the medical information system at least one health care condition in terms of a specified logical relationship among a plurality of health care events relevant to diagnosis and reported in the health care claims records;

(c) identifying in the health care claims records those enrollees meeting the definition for said at least one health care condition;

(d) defining in the medical information system health care quality criteria for said at least one health care condition in terms of a plurality of health care events reported or reportable in the health care claims records, including at least one intervention based on practice guidelines and related to care for the at least one health care condition;

(e) comparing the health care quality criteria for said at least one health care condition to the health care claims records for at least a portion of those enrollees meeting the definition for said at least one health care condition; and (f) developing and outputting from said medical information system a health care quality report based on the comparison of step (e) and including action recommendations for improving health care quality as defined by said health care quality criteria.

12. The method of claim 11 wherein multiple health care conditions and corresponding health care quality criteria for said multiple health care conditions are defined.

13. The method of claim 11 further comprising the steps of:
   (g) providing to said processing unit of said medical information system medical records for a selected enrollee population that is a subset of the enrollee population identified as meeting the definition for said at least one health care condition;
   (h) defining health care quality criteria for said at least one health care condition also in terms of health care events reported in the medical records;
   (i) comparing the health care quality criteria for said at least one health care condition to the medical records for at least some of those enrollees meeting the definition for said at least one health care condition; and
   (j) developing and outputting from said medical information system a report based on the comparison of step (i) as well as step (e) and including action recommendations for improving health care quality as defined by said health care quality criteria.

14. A medical information system for analyzing health care claims records for a health care benefit plan to assess quality of care received by plan members having a specified health care condition and formulate action recommendations to improve care comprising:
   (a) a central processing unit;
   (b) at least one memory unit connected to said central processing unit;
   (c) means for providing to said processing unit health care claims records for a selected enrollee population;
   (d) means for defining at least one health care condition in terms of a specified logical relationship among a plurality of health care events relevant to diagnosis and reported in the health care claims records;
   (e) means for identifying in the health care claims records those enrollees meeting the definition for said at least one health care condition;
   (f) means for defining health care quality criteria for said at least one health care condition in terms of a plurality of health care events reported or reportable in health care claims records, including at least one intervention based on practice guidelines related to care for the at least one health care condition;
   (g) means for comparing the health care quality criteria for said at least one health care condition to the health care claims records for at least a portion of those enrollees meeting the definition for said at least one health care condition; and
   (h) means for developing and outputting from said medical information system a health care quality report based on the comparison performed by means (g) and including action recommendations for improving health care quality as defined by said health care quality criteria.

15. The system of claim 14 wherein the means for providing health care claims records comprises means for providing records from a group consisting of: claims records for medical professional services, claims records for hospital services and claims records for pharmaceutical prescriptions.

16. The system of claim 14 further comprising:
   (i) means for providing to said processing unit of said medical information system medical records for a selected enrollee population that is a subset of the enrollee population identified as meeting the definition for said at least one health care condition;
   (j) means for defining health care quality criteria for said at least one health care condition also in terms of health care events reported or reportable in the medical records;
   (k) means for comparing the health care quality criteria for said at least one health care condition to the medical records for at least some of those enrollees meeting the definition for said at least one health care condition; and
   (l) means for developing and outputting from said medical information system a report based on the comparison performed by means (k) as well as means (g) and including action recommendations for improving health care quality as defined by said health care quality criteria.

17. A medical information system for analyzing records for a health care benefit plan, wherein said medical information system assesses quality of care received by plan members having a specified health care condition and formulates action recommendations to improve care, said medical information system comprising:
   (a) a processor;
   (b) a database, accessible by said processor, wherein said database includes information from health care claim records for a selected enrollee population that is a subset of the enrollee population identified as meeting said definition for said at least one health care condition;
   (c) a data storage medium accessible by the processor, wherein the data storage medium has a program stored on it, and wherein the program is configured to cause the processor to:
   define at least one health care condition in terms of a specified logical relationship among a plurality of health care events relevant to diagnosis and reported or reportable in said health care claims records,
   define health care quality criteria in terms of a plurality of health care events reported or reportable in said health care claims records, including at least one intervention based on practice guidelines and related to care for said at least one health care condition,
   identify enrollees meeting said definition for said at least one health care condition,
   compare health care quality criteria for said at least one health care condition to said information from said health care claims records for at least a portion of those enrollees meeting said definition for said at least one health care condition, and
   formulate action recommendations for improving health care quality as defined by said health care quality criteria; and
   (d) an output device, connected to the processor, for outputting from said medical information system a health care quality report.

18. A medical information system as claimed in claim 17, wherein said output device is a printer.

19. A medical information system as claimed in claim 17, wherein said output device is a computer display.

20. A medical information system as claimed in claim 17, wherein said claims database includes
   information from said health care claims records for medical professional services;

information from said health care claims records for hospital services; and information from said health care claims records for pharmaceutical prescriptions.

21. The system of claim 17, wherein said data medium includes at least one random access memory device.

22. The system of claim 17, wherein said data medium includes at least one magnetic media disk.

23. A data storage medium for use with a processor that accesses a database of information from health care claim records for an enrolled population, wherein the data storage medium has a program stored on it that causes the processor to:

(a) define at least one health care condition in terms of a specified logical relationship among a plurality of health care events relevant to diagnosis and reported or reportable in said health care claims records;

(b) define health care quality criteria in terms of a plurality of health care events reported or reportable in said health care claims records, including at least one intervention based on practice guidelines and related to care for said at least one health care condition;

(c) identify enrollees meeting said definition for said at least one health care condition;

(d) compare health care quality criteria for said at least one health care condition to said information from said health care claims records for at least a portion of those enrollees meeting said definition for said at least one health care condition; and (e) formulate action recommendations for improving health care quality as defined by said health care quality criteria.

* * * * *